(12) United States Patent
Giguere et al.

(10) Patent No.: US 9,499,557 B2
(45) Date of Patent: Nov. 22, 2016

(54) TRANSITION METAL-CATALYZED PROCESSES FOR THE PREPARATION OF N-ALLYL COMPOUNDS AND USE THEREOF

(71) Applicant: Rhodes Technologies, Coventry, RI (US)

(72) Inventors: Joshua Robert Giguere, Sharon, MA (US); Keith Edward McCarthy, Old Lyme, CT (US); Helge Alfred Reisch, Westerly, RI (US); Sergio Sandoval, West Warwick, RI (US); Jake Larry Stymiest, Foster, RI (US)

(73) Assignee: Rhodes Technologies, Coventry, RI (US)

( * ) Notice: Subject to any disclaimer, the term of this patent is extended or adjusted under 35 U.S.C. 154(b) by 0 days.

(21) Appl. No.: 14/827,132

(22) Filed: Aug. 14, 2015

(65) Prior Publication Data

US 2015/0353569 A1  Dec. 10, 2015

Related U.S. Application Data

(60) Division of application No. 13/711,520, filed on Dec. 11, 2012, now Pat. No. 9,127,014, which is a continuation of application No. PCT/IB2011/001330, filed on Jun. 10, 2011.

(60) Provisional application No. 61/354,036, filed on Jun. 11, 2010.

(51) Int. Cl.
| | | |
|---|---|---|
| *C07D 489/00* | (2006.01) |
| *C07D 489/08* | (2006.01) |
| *B01J 31/24* | (2006.01) |
| *B01J 31/18* | (2006.01) |
| *B01J 31/22* | (2006.01) |
| *B01J 31/20* | (2006.01) |
| *B01J 23/42* | (2006.01) |
| *B01J 23/44* | (2006.01) |
| *C07D 295/03* | (2006.01) |
| *C07D 295/205* | (2006.01) |
| *C07C 209/00* | (2006.01) |
| *C07C 269/04* | (2006.01) |
| *C07D 265/30* | (2006.01) |
| *C07C 209/44* | (2006.01) |

(52) U.S. Cl.
CPC .............. *C07D 489/08* (2013.01); *B01J 23/42* (2013.01); *B01J 23/44* (2013.01); *B01J 31/1855* (2013.01); *B01J 31/20* (2013.01); *B01J 31/2295* (2013.01); *B01J 31/2414* (2013.01); *C07C 209/00* (2013.01); *C07C 209/44* (2013.01); *C07C 269/04* (2013.01); *C07D 265/30* (2013.01); *C07D 295/03* (2013.01); *C07D 295/205* (2013.01); *B01J 2231/40* (2013.01); *B01J 2531/64* (2013.01); *B01J 2531/821* (2013.01); *B01J 2531/824* (2013.01); *B01J 2531/828* (2013.01); *B01J 2531/847* (2013.01); *Y02P 20/55* (2015.11)

(58) Field of Classification Search
CPC ..................................................... C07D 489/08
USPC ........................................................... 546/45
See application file for complete search history.

(56) References Cited

U.S. PATENT DOCUMENTS

| | | | |
|---|---|---|---|
| 1,468,805 A | 9/1923 | Freund et al. |
| 1,485,673 A | 3/1924 | Freund et al. |
| 2,191,786 A | 2/1940 | Aronow |
| 2,583,420 A | 1/1952 | Garber et al. |
| 2,772,270 A | 11/1956 | Weiss |
| 2,806,033 A | 9/1957 | Mozes et al. |
| 3,254,088 A | 5/1966 | Lewenstein et al. |
| 3,332,950 A | 7/1967 | Blumberg et al. |
| 3,342,824 A | 9/1967 | Pohland et al. |
| 3,355,486 A | 11/1967 | Berkowitz et al. |
| 3,433,791 A | 3/1969 | Bentley et al. |
| 3,749,646 A | 7/1973 | Pirt |
| 3,812,132 A | 5/1974 | Robertson |
| 3,872,127 A | 3/1975 | Mertz et al. |
| 3,905,981 A | 9/1975 | Olofson et al. |
| 3,923,987 A | 12/1975 | Mertz et al. |
| 3,931,187 A | 1/1976 | Langbein |
| 4,003,903 A | 1/1977 | Schwartz |
| 4,045,440 A | 8/1977 | Rapoport |
| 4,141,897 A | 2/1979 | Olofson et al. |
| 4,161,597 A * | 7/1979 | Olofson ............... C07D 489/08 546/15 |

(Continued)

FOREIGN PATENT DOCUMENTS

| | | |
|---|---|---|
| CA | 1244825 | 11/1988 |
| CA | 2567213 C | 8/2012 |

(Continued)

OTHER PUBLICATIONS

Dorwald F. A. Side Reactions in Organic Synthesis, 2005, Wiley: VCH, Weinheim p. IX of Preface p. 1-15.*

(Continued)

*Primary Examiner* — Nizal Chandrakumar
(74) *Attorney, Agent, or Firm* — Dechert LLP

(57) ABSTRACT

The present disclosure provides processes for the N-dealkylation of tertiary amines and the use of transition metal catalysts to prepare tertiary N-allyl amine derivatives and secondary amine derivatives thereof. The tertiary amines can be alkaloids and, more particularly, the tertiary amines can be opioids. In specific embodiments, the present disclosure provides methods for use in processes for the synthesis of naloxone and naltrexone from oripavine.

29 Claims, No Drawings

(56) References Cited

U.S. PATENT DOCUMENTS

| | | |
|---|---|---|
| 4,217,287 A | 8/1980 | Bozik et al. |
| 4,217,787 A | 8/1980 | Liebing et al. |
| 4,472,253 A | 9/1984 | Schwartz |
| 4,535,157 A | 8/1985 | Meltzer et al. |
| 4,639,520 A | 1/1987 | Kavka |
| 4,667,037 A | 5/1987 | Bryant |
| 4,795,813 A | 1/1989 | Schwartz |
| 5,112,975 A | 5/1992 | Wallace |
| 5,518,988 A | 5/1996 | Sisler et al. |
| 5,587,474 A | 12/1996 | Kondo et al. |
| 5,668,285 A | 9/1997 | Rice et al. |
| 5,847,142 A | 12/1998 | Mudryk et al. |
| 5,869,669 A | 2/1999 | Huang et al. |
| 5,922,876 A | 7/1999 | Huang et al. |
| 5,952,495 A | 9/1999 | Huang et al. |
| 5,994,327 A | 11/1999 | Schmidhammer et al. |
| 5,994,372 A | 11/1999 | Yaksh |
| 6,017,849 A | 1/2000 | Daly et al. |
| 6,067,749 A | 5/2000 | Fist et al. |
| 6,177,567 B1 | 1/2001 | Chiu et al. |
| 6,262,266 B1 | 7/2001 | Chiu et al. |
| 6,277,859 B1 | 8/2001 | Nagase et al. |
| 6,291,675 B1 | 9/2001 | Coop et al. |
| 6,335,459 B1 | 1/2002 | Lopez-Tapia et al. |
| 6,365,742 B1 | 4/2002 | Mudryk et al. |
| 6,376,211 B1 | 4/2002 | Little et al. |
| 6,395,900 B1 | 5/2002 | Coop et al. |
| 6,403,798 B2 | 6/2002 | Chiu et al. |
| 6,405,301 B1 | 6/2002 | Duranton |
| 6,486,692 B1 | 11/2002 | Chen |
| 6,569,170 B1 | 5/2003 | Kellogg |
| 6,723,894 B2 | 4/2004 | Fist et al. |
| 6,790,959 B1 | 9/2004 | Lin et al. |
| 6,864,370 B1 | 3/2005 | Lin et al. |
| 6,927,294 B1 | 8/2005 | Petasis et al. |
| 6,949,645 B1 | 9/2005 | Francis |
| 6,972,332 B1 | 12/2005 | Francis |
| 6,994,827 B2 | 2/2006 | Safir et al. |
| 7,071,336 B2 | 7/2006 | Francis et al. |
| 7,129,248 B2 | 10/2006 | Chapman et al. |
| 7,217,822 B2 | 5/2007 | Comin et al. |
| 7,285,665 B2 | 10/2007 | Cantrell et al. |
| 7,405,301 B2 | 7/2008 | Scammells et al. |
| 7,435,817 B2 | 10/2008 | Linders et al. |
| 7,501,433 B2 | 3/2009 | Wu et al. |
| 7,671,204 B2 | 3/2010 | Wang et al. |
| 7,875,718 B2 | 1/2011 | Smith et al. |
| 8,134,002 B2 | 3/2012 | Huang |
| 8,217,175 B2 | 7/2012 | Wang et al. |
| 8,252,808 B2 | 8/2012 | Wang et al. |
| 8,278,344 B2 | 10/2012 | Cuny et al. |
| 8,309,727 B2 | 11/2012 | Wang et al. |
| 8,357,802 B2 | 1/2013 | Huang |
| 8,546,572 B2 | 10/2013 | Patel et al. |
| 8,598,352 B2 | 12/2013 | De Faveri et al. |
| 8,669,366 B2 | 3/2014 | Wang et al. |
| 8,921,556 B2 | 12/2014 | Giguere et al. |
| 9,127,014 B2 | 9/2015 | Giguere et al. |
| 9,309,258 B2 | 4/2016 | Giguere et al. |
| 2005/0065033 A1 | 3/2005 | Jacobson et al. |
| 2006/0005112 A1 | 1/2006 | Lilly et al. |
| 2006/0009479 A1 | 1/2006 | Bailey et al. |
| 2006/0009497 A1 | 1/2006 | Bezencon et al. |
| 2006/0195934 A1 | 8/2006 | Apuya et al. |
| 2006/0236421 A1 | 10/2006 | Pennell et al. |
| 2007/0142634 A1 | 6/2007 | Barrow et al. |
| 2007/0199090 A1 | 8/2007 | Apuya et al. |
| 2008/0045558 A1 | 2/2008 | Gant et al. |
| 2008/0125592 A1 | 5/2008 | Huang |
| 2008/0146601 A1 | 6/2008 | Dung et al. |
| 2008/0207906 A1 | 8/2008 | Wang et al. |
| 2008/0234306 A1 | 9/2008 | Perez et al. |
| 2008/0262231 A1 | 10/2008 | Wang et al. |
| 2008/0275240 A1 | 11/2008 | Wang et al. |
| 2008/0312441 A1 | 12/2008 | Mannino et al. |
| 2009/0005564 A1 | 1/2009 | Carroll et al. |
| 2009/0005565 A1 | 1/2009 | Carroll et al. |
| 2009/0047279 A1 | 2/2009 | Perez |
| 2009/0075822 A1 | 3/2009 | Cotterill |
| 2009/0156815 A1 | 6/2009 | Wang et al. |
| 2009/0156819 A1 | 6/2009 | Wang et al. |
| 2009/0221766 A1 | 9/2009 | Cheng et al. |
| 2009/0270624 A1 | 10/2009 | Weigl et al. |
| 2010/0022774 A1 | 1/2010 | Kvernenes et al. |
| 2010/0036128 A1 | 2/2010 | Rezaie et al. |
| 2010/0081817 A1 | 4/2010 | Hudson et al. |
| 2013/0102784 A1 | 4/2013 | Reisch et al. |
| 2013/0237559 A1 | 9/2013 | Ortiz et al. |
| 2015/0336972 A1 | 11/2015 | Giguere et al. |
| 2015/0353567 A1 | 12/2015 | Giguere et al. |
| 2015/0353568 A1 | 12/2015 | Giguere et al. |

FOREIGN PATENT DOCUMENTS

| | | |
|---|---|---|
| EP | 0009227 A1 | 4/1980 |
| EP | 0158476 | 10/1985 |
| EP | 0632041 | 1/1995 |
| EP | 1555266 | 7/2005 |
| GB | 939287 | 10/1963 |
| GB | 1260699 | 1/1972 |
| GB | 2000137 | 1/1979 |
| JP | S60-252481 | 12/1985 |
| JP | 2004-512263 | 4/2004 |
| JP | 2004-516295 | 6/2004 |
| JP | 2010-518128 | 5/2010 |
| WO | WO 98/02033 A1 | 1/1998 |
| WO | WO 01/98267 | 12/2001 |
| WO | WO 02/50070 | 6/2002 |
| WO | WO 2005/097801 AI | 10/2005 |
| WO | WO 2006/094672 A1 | 9/2006 |
| WO | WO 2008/098368 | 8/2008 |
| WO | WO 2008/137672 A1 | 11/2008 |

OTHER PUBLICATIONS

Acosta et al., "Oxidative Demethylation of 4-Substituted N,N-Dimethylanilines with Iodine and Calcium Oxide in the Presence of Methanol," (1994) *J. Chem. Soc., Chem. Commun.* 17(7):1985-1986.

Aggarwal et al., "Highly Diastereoselective Simmons-Smith Cyclopropanation of Allylic Amines," (2003) *Org. Lett.* 5(23):4417-4420.

Andre et al. (1992) *Synthetic Comm.* 22(16):2313-2327.

Balas et al., "Total Synthesis of Photoactivatable or Fluorescent Anandamide Probes: Novel Bioactive Compounds with Angiogenic Activity," (2009) *J. Med. Chem.* 52:1005-1017.

Barber et al. (1975) *J. Med. Chem.* 18(11):1074-1077.

Bellingham et al. (2004) *Org. Process Res. Devel.* 8:279-282.

Beugelmans et al., "Reductive Deprotection of Aryl Allyl Ethers with Pd(Ph$_3$)$_4$/NaBH$_4$," (1994) *Tetrahedron Lett.* 35:4349-4350.

Bhatt et al., "Silicon Tetrachloride/Sodium Iodide as a Convenient and Highly Regioselective Ether Cleaving Reagent," (1982) *Synthesis* 12:1048-1050.

Bois-Choussey et al., "Synthesis of Modified Carboxyl Binding Pockets of Vancomycin and Teicoplanin," (1996) *J. Org. Chem.* 61:9309-9322.

Boss et al., "Bridgehead Cations of Tricycl0[5.2.1.0$^{4,10}$]deca-2,5,8-triene (Triquinacene)," (1976) *Angew. Chem., Int. Ed. Engl.* 15:557-558.

Bruce et al., "Cleavage of Allyl Phenyl Ethers by Bis(benzonitrile)palladium(II) Chloride," (1981) *J. Chem. Res. Synop.* 7:193.

Cacchi et al., "Palladium-catalyzed synthesis of 2-amino ketones from propargylic carbonates and secondary amines," (2012) *Org. Biomol. Chem.* 10:4699-4703.

Chiappe et al. An efficient stereoselective synthesis of enantiomerically pure aziridine derivatives of allyl β-D-glucopyranosides asymmetrically induced by a glucide moiety (1998) *Asymmetry* 9:4079-4088.

(56) References Cited

OTHER PUBLICATIONS

Cooley et al., "Amine Dealkylations with Acyl Chlorides," (Jan. 1989) *Synthesis* pp. 1-7.
Coop et al. (1998) *J. Org. Chem.* 63:4392-4396.
Denis et al., "Novel N-demethylation of ketolide: application to the solution phase parallel synthesis of N-desosaminyl-substituted ketolides using ion exchange resins," (2002) *Tetrahedron Lett.* 43:4171-4174.
Dessolin et al., "New Allyl Group Acceptors for Palladium Catalyzed Removal of Allylic Protections and Transacylation of Allyl Carbamates," (1995) *Tetrahedron Lett.* 36:5741-5744.
Dorwald, "Side Reactions in Organic Synthesis" (2005) Wiley-VCH, Weinheim, Germany, p. IX of Preface and pp. 1-16, 40, 41, 278-309.
Dulayymi et al.,"1,2,2-Tribromocyciopropanecarboxylic Acid and Derivatives—Valuable Intermediates for Four Carbon Cyclopropane and Cyclopropene Synthons," (1996) *Tetrahedron* 52(10)3409-3424.
Fahrenholtz, "The Synthesis of Two Metabolites of (−)-$\Delta^8$-Tetrahydxocannabinol," *J. Org. Chem.* 37(13):2204-2207.
Four et al., "Palladium-Catalyzed Conjugate Reduction of A, B-Unsaturated Carbonyl Compound with Tributyltin Hydride. The Promoting Influence of the Presence of Protonic or Lewis Acids.," (1982) *Tetrahedron Lett.* 23:1825-1828.
Freund et al. (1916) *J. Prakt. Chem.* 94;:135-178.
Garro-Helion et al., "Mild and Selective Palladium (0)-Catalyzed Deallylation of Allylic Amines. Allylamine and Diallylamine as Very Convenient Ammonia Equivalents for the Synthesis of Primary Amines," (1993) *J. Org. Chem.* 58:6109-6113.
Gerszberg et al. (1973) *Tetrahedron Lett.* 14(15):1269-1272.
Gesson et al., "Preparation of N-Demethyl and N-Alkyl Analogs of L-Rhodosamine," (Nov. 1990) *Synlett* pp. 669-670.
Greiner et al. (2004) *J. Med. Chem.* 46(9):1758-1763.
Guthikonda et al., "A Unique and Highly Efficient Method for Catalytic Olefin Aziridination," (2002) *J. Am. Chem. Soc.* 124:13672-13673.
Hey et al., "Removal of Allyl groups by Formic Acid Catalyzed by (Triphenyl phosphane)palladium," (1973) *Angew. Chem., Int. Ed. Engl.* 12:928-929.
Hosztafi et al. (1992) *Monatshefte für Chemie* 123:435-441.
Iijima et al. (1977) *Helvetica Chimica Acta* 60:2135-2137.
International Preliminary Report on Patentability dated Dec. 14, 2012 for International Application No. PCT/IB2011/001330.
International Search Report for International Application No. PCT/IB2011/001330 dated Jul. 3, 2012.
Kametani et al., "A Novel Cleavage of Aryl Benzyl Ethers and Allyl Aryl Ethers by Sodium Bis( 2-methoxyethoxy)aluminum Hydride. An Alternative Synthesis of Pentazocine," (1976) *J. Org. Chem.* 41:2545-2548.
Kariyone et al., "Oxidative Cleavage of (βY-Unsaturated Ether," (1970) *Tetrahedron Lett.* 11(33):2885-2888.
Kim et al., "A New Class of $S_N2$ Reactions Catalyzed by Protic Solvents: Facile Fluorination for Isotopic Labeling of Diagnostic Molecules," (2006) *J. Am. Chem. Soc.* 128:16394-16397.
Kim et al., "Facile nucleophilic fluorination by synergistic effect between polymer-supported ionic liquid catalyst and *tert*-alcohol reaction media system," (2004) *Tetrahedron* 64:4209-4214.
Koreeda et al. (1984) *J. Org. Chem.* 49:2081-2082.
Krassnig et al. (1998) *Heterocycles* 47:1029-1032.
Krassnig et al., "Optimization of the Synthesis of Oxycodone and 5-Methyloxycodone," (1996) *Arch. Pharm. Med. Chem.* 329:325-326.
Mann et al., "761. The Dealkylation of Alkyl Aryl Ethers and Sulphides by Diaryl-phosphide and -arsenide Ions," (1965) *J. Chem. Soc.* pp. 4120-4127.
Martin et al., "Enantio- and Diastereoselectivity in the Intramolecular Cyclopropanation of Secondary Allylic Diazoacetates," (1994) *J. Am. Chem. Soc.* 116:4493-4494.

Martin et al., "General Methods for Alkaloid Synthesis. Total Synthesis of Racem ic L ycoramine," (1982) *J. Org. Chem.* 47:1513-1518.
McCamley et al., "Efficient N-Demethylation of Opiate Alkaloids Using a Modified Nonclassicelect Polonovski Reaction," (2003) *J. Org. Chem. Soc.* 68:9847-9850.
Mellegaard-Waetzig et al., "Allylic Amination via Decarboxylative C-N Bond Formation," (2005) *Synlett* 18:2759-2762.
Menchaca et al., "Synthesis of Natural Ecteinascidins (ET-729, ET-745, ET-759B, ET-736, ET-637, ET-594) from Cyanosafracin B," (2003) *J. Org. Chem.* 68:8859-8866.
Murahashi et al., "Aerobic Ruthenium-Catalyzed Oxidative Cyanation of Tertiary Amines with Sodium Cyanide," (2003) *J. Am. Chem. Soc.* 125:15312-15313.
Murahashi et al., "Ruthenium-Catalyzed Cytochrome P-450 Type Oxidation of Tertiary Amines with Alkyl Hydroperoxides," (1988) *J. Am. Chem. Soc.* 110:8256-8258.
Murahashi et al., "Ruthenium-Catalyzed Oxidation of Tertiary Amines with Hydrogen Peroxide in the Presence of Methanol." (1992) *Tetrahedron Lett.* 33:6991-6994.
Murahashi, "Synthetic Aspects of Metal-Catalyzed Oxidations of Amines and Related Reactions," (1995) *Angew. Chem., Int. Ed. Engl.* 34:2443-2465.
Ninan et al. (1992) *Tetrahedron* 48(32):6709-6716.
Notice of Reasons for Rejection for JP Application No. 2013-513776 dated Mar. 25, 2014.
Novak et al. (2000) *Current Org. Chem.* 4:343-362, at 343-344.
Olah et al., "Baeyer-Villiger Oxidation of Ketones to Esters with Sodium Perearbonatenirifluoroacetic Acid," (1991) *Synthesis*, pp. 739-740.
Olofson et al., "A New Reagent for the Selective, High-Yield N-Dealkylation of Tertiary Amines: Improved Syntheses of Naltrexone and Nalbuphine," (1984) *J. Org. Chem.* 49(11):2081-2083.
Opatz (2004) *Eur. J. Org. Chem.* 20:4113-4118.
Periasmy et al., "Aryltitanium Species through the Reaction of N,N-Dialkylarylamines with $TiCl_4$: Oxidative Coupling, N-Dealkylation, and Reaction with Electrophiles," (2000) *J. Org. Chem.* 65:3548-3550.
Polniaszek et al., "Stereospecific Total Syntheses of Decahydroquinoline Alkaloids (±)-195A and (±)-2-epi-19," (1992) *J. Org. Chem.* 57:4103-4110.
Rao (1982) *J. Org. Chem.* 47:369-371.
Rice et al., "An Improved Procedure for the N-Demethylation of 6,7-Benzomorphans, Morphine, and Codeine," (1975) *J. Org. Chem.* 40(12):1850-1851.
Rosenau et al., "A General, Selective, High-Yield N-Demethylation Procedure for Tertiary Amines by Solid Reagents in a Convenient Column Chromatography-like Setup," (2004) *Org. Lett.* 6:541-544.
Rubin et al. (2007) *Chem. Rev.* 107:3117-3179.
Saaby et al., "Formation of Optically Active Aromatic alpha-Amino Acids by Catalytic Enantioselective Addition of Imines to Aromatic Compounds," (2000) *Angew. Chem., Int. Ed. Engl.* 39:4114-4116.
Sakuma et al., "Facile preparation of cyclopropanes from 2-iodoethyl-substituted olefins and 1,3-dihalopropanes with zinc powder," (2005) *Tetrahedron* 61:10138-10145.
Santamaria et al., "Electron-Transfer Activation. Photochemical N-Demethylation of Tertiary Amines," (1989) *Tetrahedron Lett.* 30:2927-2928.
Santamaria et al., "Electron-Transfer Activation. Photocyanation of Tertiary Amines," (1990) *Tetrahedron Lett.* 31:4735-4738.
Schmidhammer et al. (1989) *Helvetica Chimica Acta, Verlag Helvetical Chimica Acta* 72(6):1233-1240.
Schwartz et al., "Efficient Synthesis of 14-Hydroxymorphinans from Codeine," (1981) *J. Med. Chem.* 24:1525-1528.
Small (1938) *J. Org. Chem.* 3:204-232.
Stattely et al., "Design and Stereoselective Preparation of a New Class of Chiral Olefin Metathesis Catalysts and Application to Enantioselective Synthesis of Quebrachamine: Catalyst Development Inspired by Natural Product Synthesis," (2009) *J. Am. Chem. Soc.* 131:943-953.
Taiwan IPO Search Report for Taiwan Patent Application No. 100120387 dated Jun. 4, 2014.

(56) References Cited

OTHER PUBLICATIONS

Takai et al., "Stereoselective Iodocyclopropanation of Terminal Alkenes with Iodoform, Chromium(II) Chloride, and N,N,N',N'-Tetraethylethylenediamine," (2003) *J. Am. Chem. Soc.* 125:12990-12991.

Thomas et al., "A Novel, Mild and Facile Reductive Cleavage of Allyl ethers by $NaBH_4/I_2$ System," (1997), *Tetrahedron Lett.* 38(26):4721-4724.

Torque et al., "Substrate-Selective Aqueous Organometallic Catalysis. How Small Water-Soluble Organic Molecules Enhance the Supramolecular Discrimination," (2005) *Tetrahedron* 61:4811-4817.

Villani et al., "N-Substituted 11-(4-Piperidylene)-5,6-dihydro-11H-benzo-[5,6]cyclohepta[1,2-b]pyridines," (1986) *Arzneim-Forsch./Drug. Res.* 36(9):1311-1314.

Written Opinion dated Jul. 3, 2012 for International Application No. PCT/IB2011/001330.

Xu et al., "Aziridination of Aliphatic Alkenes Catalyzed by N-Heterocyclic Carbene Copper Complexes," (2008) *Org. Lett.* 10(7):1497-1500.

Yeti et al. (2006) *Bioorg. Med. Chem. Lett.* 16:5408-5413.

Zhang et al., "Synthesis of 2-Fluoro-11-hydroxy-N-propylnoraporphine: A Potential Dopamine D2 Agonist," (2005) *Org. Lett.* 7:3239-3242.

Abdel-Rahman et al., "Synthesis and Pharmacology of 6-Methylenedihydrodesoxymorphine," (1966) *J. Med. Chem.* 9(1):1-6.

Ege et al., Organic Chemistry pp. Inside front cover (3$^{rd}$ ed., D.C. Heath and Co., Lexington, MA, 1994).

Extended European Search Report dated Dec. 4, 2015 for European Patent Application No. EP15186900.5.

Gates et al., "Some Potent Morphine Antagonists Possessing High Analgesic Activity," (1964) *J. Med. Chem.* 7:127-131 and Annex 1 (Yield calculation for Gates) thereto.

Genet J. P. et al., "A General and Simple Removal of the Allyloxycarbonyl Protecting Group by Palladium-Catalyzed Reactions Using Nitrogen and Sulfur Nucleophiles," Synlett, 1993, pp. 680-682.

Japanese Office Action dated Dec. 8, 2015 for Japanese Patent Application No. 2014-262237 (English Translation attached).

Krassnig et al., "A New and Efficient Synthesis of the μ-Selective Opioid Antagonist Cyprodime," (1994) *Heterocycles* 38(4):877-881.

Krassnig et al., "A Novel Method for the Introduction of a 5β-Methyl Group into 4,5α-Epoxymorphinan-6-ones via the Enol Ether," (2000) *Helvetica Chimica Acta* 83:380-383.

Leisch et al., "Studies on Regioselective Hydrogenation of Thebaine and its Conversion to Hydrocodone," (2007) *Tetrahedron Lett.* 48(23):3979-3981.

Lide et al., "Dissociation Constants of Organic Acids and Bases," *CRC Handbook of Chemistry and Physics* pp. 8-42 through 8-51 (90$^{th}$ ed., CRC Press, Boca Raton, FL, 2009).

\* cited by examiner

US 9,499,557 B2

TRANSITION METAL-CATALYZED PROCESSES FOR THE PREPARATION OF N-ALLYL COMPOUNDS AND USE THEREOF

This application is a divisional of application Ser. No. 13/711,520, filed Dec. 11, 2012, now U.S. Pat. No. 9,127,014 B2, which is a continuation of International application no. PCT/IB2011/001330, filed Jun. 10, 2011, which claims the benefit under 35 U.S.C.§119(e) of provisional application No. 61/354,036, filed Jun. 11, 2010, the contents of all of which are incorporated herein by reference.

1. FIELD

The present disclosure provides processes for preparing N-allyl amines from tertiary N-alkyl amines. The disclosed processes include haloformate-promoted N-dealkylation of a tertiary amine and a subsequent transition metal-catalyzed allylic decarboxylation to provide the N-allyl amine. The tertiary amines can be alkaloids, and more particularly, the tertiary amines can be opioids.

2. BACKGROUND

N-dealkylation of tertiary amines is a key chemical transformation in many processes for the preparation of clinically and commercially important compounds. Methods for N-dealkylation of tertiary amines are known in the art and include reaction of the tertiary amine with cyanogen bromide (see, e.g., U.S. Pat. Nos. 3,254,088 and 3,433,791; and Cooley et al., "Amine Dealkylations with Acyl Chlorides" (1989) Synthesis 1-7), dialkyl azodicarboxylates including diethylazodicarboxylate and di-iso-propylazodicarboxylate, (see, e.g., GB 1,124,441), and haloformate reagents, including vinyl, methyl, ethyl, allyl, propyl, heptyl, phenyl, benzyl, α-chloro-ethyl, and 2,2,2-tri-chloro-ethyl chloroformates (see, e.g., U.S. Pat. Nos. 3,905,981 and 4,472,253; Olofson et al. (1984) J. Org. Chem. 49(11):2081-2083; and Rice et al. (1975) J. Org. Chem. 40(12):1850-1851).

Additional methods for N-dealkylation, particularly N-demethylation of tertiary amines, involve photochemical cleavage, as well as the formation and hydrolysis of dithiocarbamate, methyoxymethylether, and amine N-oxide intermediates to provide the corresponding secondary amine derivatives (see, e.g., Santamaria et al. (1989) Tetrahedron Lett. 30:2927; Santamaria et al. (1990) Tetrahedron Lett. 31:4735; Acosta et al. (1994) J. Chem. Soc., Chem. Commun. 17(7):1985-1986; Murahashi et al. (1988) J. Am. Chem. Soc. 110:8256; Murahashi (1995) Angew. Chem., Int. Ed., Engl. 34:2443; Polniaszek et al. (1992) J. Org. Chem. 57:4103; Murahashi et al. (1992) Tetrahedron Lett. 33:6991; Murahashi et al. (2003) J. Am. Chem. Soc. 125:15312; McCamley et al. (2003) J. Org. Chem. Soc. 68:9847; Gesson et al., "Preparation of N-Demethyl and N-Alkyl Analogs of L-Rhodosamine" (November 1990) Synlett. 669-670; Rosenau et al. (2004) Org. Lett. 6:541; Menchaca et al. (2003) J. Org. Chem. 68:8859; Periasamy et al. (2000) J. Org. Chem. 65:3548; Saaby et al. (2000) Angew. Chem., Int. Ed., Engl. 39(22):4114-4116; Denis et al. (2002) Tetrahedron Lett. 43:4171; and Zhang et al. (2005) Org. Lett. 7:3239).

In particular, methods for the preparation of noroxymorphone and noroxycodone involve removal of the naturally occurring opioid N-methyl group to provide the corresponding secondary amine. Methods for the preparation of other semi-synthetic opiate derivatives, e.g., naloxone, naltrexone, nalorphine, nalmefene, and nalbuphine, involve removal of that naturally occurring opioid N-methyl group and its replacement with another alkyl or an alkenyl moiety. The ultimate starting materials for preparation of these semi-synthetic compounds include the natural products morphine, codeine, thebaine, and oripavine. Among these, thebaine and oripavine are particularly useful because they are readily oxidized to introduce the 14-hydroxyl group carried by each of the above semi-synthetic opiates. In a similar manner, the semi-synthetic processes for the synthesis of buprenorphine, levallorphan, pentazocine, cyclazocine, and ketazocine also involve replacement of an N-methyl group of a tertiary amine with an alkyl or an alkenyl moiety. Synthesis of cabergoline from either lysergol or elymoclavine also involves replacement of a tertiary N-methyl group with an allyl moiety.

As described in the above references, the tertiary amine is converted to an intermediate that is subsequently cleaved to provide the corresponding dealkylated (demethylated) secondary amine. The secondary amine can then be realkylated, e.g., by condensation with an alkyl or alkenyl halide selected from among propyl iodide, cyclopropyl methyl bromide, cyclobutyl methyl bromide, and allyl bromide (see, e.g., U.S. Pat. Nos. 3,905,981; 4,141,897; 3,254,088; 3,332,950; and 3,433,791).

However, these reactions can involve the use of materials and reagents that are relatively expensive, toxic and environmentally burdensome. Furthermore, the synthetic schemes disclosed generally involve three steps for conversion of a tertiary amine to the corresponding N-allyl derivative, as noted above. Such processes also may require purification of intermediates, extended process times, and harsh reaction conditions, and may provide overall yields that are not commercially viable.

Accordingly, there remains a need for more efficient methods for the preparation of N-allyl derivatives of tertiary amines, as well as for improved processes incorporating those methods that would be robust, cost effective, amenable to commercial scale-up, and/or that would impose lower burdens on the environment. In particular, there remains a need for more efficient methods for preparing semi-synthetic opiate derivatives including, e.g., naloxone, naltrexone, nalmefene, nalbuphine, noroxymorphone, noroxycodone, and buprenorphine, as well as levallorphan, pentazocine, cyclazocine, ketazocine, and cabergoline.

3. SUMMARY

The present disclosure provides methods for the preparation of N-allyl compounds from tertiary amines that involve conversion of the tertiary amine to an allyl carbamate that is, in turn, decarboxylated in a transition metal-catalyzed reaction to provide the desired N-allyl derivative. The present disclosure also provides methods for the preparation of tertiary allyl amines from secondary amines.

In one embodiment, the tertiary amine is contacted with an allyl haloformate reagent to provide the allyl carbamate derivative directly. In other embodiments, the tertiary amine is contacted with certain haloformate reagents to provide carbamate derivatives that are then converted to the corresponding allyl amine. As demonstrated below, the reactions and processes of the present disclosure are useful for the synthesis of a variety of N-allyl compounds as well as derivatives of those compounds.

In certain embodiments, the present disclosure provides methods for conversion of oxymorphone to naloxone that include transition metal-catalyzed decarboxylation reactions. In other embodiments, the present disclosure provides methods for conversion of oxymorphone to naltrexone that include transition metal-catalyzed decarboxylation reactions. In still other embodiments, the present disclosure provides methods that include transition metal-catalyzed decarboxylation reactions that are useful for the conversion of oxymorphone to noroxymorphone. In another embodiment, the present disclosure provides methods for conversion of oxymorphone to buprenorphine that include transition metal-catalyzed decarboxylation reactions.

In a specific embodiment, the reactions disclosed herein are used in processes through which oripavine, for example, is converted to naloxone. In another specific application, the reactions disclosed herein are used in processes through which oripavine is converted to naltrexone. In a further specific embodiment, the present disclosure provides processes that include transition metal-catalyzed decarboxylation reactions, for the preparation of noroxymorphone from oripavine.

In a further embodiment, the present disclosure provides a method for the conversion of naloxone to noroxymorphone.

In the embodiments involving a transition metal catalyst, the transition metal catalyst is present in an amount which enables the reaction to proceed. In certain embodiments, the transition metal catalyst is present in a sub-stoichiometric amount. In certain embodiments, the transition metal catalyst is present in a catalytic amount. In certain embodiments, the transition metal catalyst is present in an amount of from 0.001 to 30 mol % or of any numerical value within this range. In certain embodiments, the transition metal catalyst is present in an amount of from 0.1 to 10 mol % or of any numerical value within this range (like about 5 mol %).

In one embodiment, therefore, the present disclosure provides a method for making a compound of formula (1)

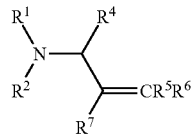

comprising
(a) converting a compound of formula (2)

to a compound of formula (3)

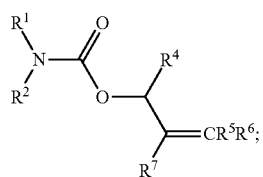

and
(b) contacting the compound of formula (3) with a transition metal catalyst to provide the compound of formula (1), where $R^1$, $R^2$, and $R^3$ are each independently selected from —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

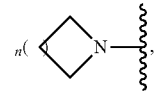

where n is an integer selected from 0, 1, 2, 3, 4, 5, 6, 7, 8, 9, 10, and 11; $R^4$ is selected from the group consisting of —H, —$(C_1$-$C_6)$ alkyl, phenyl, allyl, -2-butenyl, -3-butenyl, -4-pentenyl, -2-propynyl, -2-butynyl, -3-butynyl, -2-pentynyl,

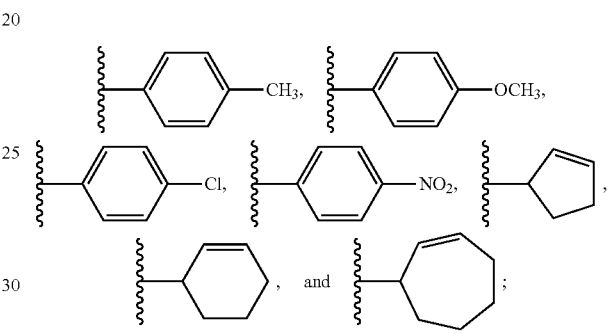

$R^5$, $R^6$, and $R^7$ are each independently selected from —H, —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —$(C_1$-$C_6)$ alkyl; and $R^{51}$ is —$(C_1$-$C_6)$ alkyl or an oxygen protecting group. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —$(C_1$-$C_6)$ alkyl; and $R^{51}$ is —$(C_1$-$C_6)$ alkyl or an oxygen protecting group.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —$O(C_1$-$C_6)$ alkyl, —C(=O)$(C_1$-$C_6)$ alkyl, and —$(C_1$-$C_6)$ alkyl, where each alkyl group is either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —$O(C_1$-$C_6)$ alkyl, and —$(C_1$-$C_6)$ alkyl, where each alkyl group is either unsubstituted or substituted with 1, 2, 3, 4, or 5 independently-selected —OR$^{53}$ groups; and R$^{53}$ is —H or an oxygen protecting group.

In certain embodiments, at least one of R$^1$, R$^2$, and R$^3$ of the tertiary amine of formula (2) is —(C$_1$-C$_6$)alkyl. In certain embodiments, R$^3$ is —(C$_1$-C$_6$)alkyl. In certain embodiments, at least one of R$^1$, R$^2$, and R$^3$ of the tertiary amine of formula (2) is methyl. In certain embodiments, R$^3$ is methyl.

In certain embodiments, the transition metal catalyst is present in a sub-stoichiometric amount. In certain embodiments, the transition metal catalyst is present in a catalytic amount. In certain embodiments, the transition metal catalyst is present in an amount of from 0.001 to 30 mol % or of any numerical value within this range. In certain embodiments, the transition metal catalyst is present in an amount of from 0.1 to 10 mol % or of any numerical value within this range (like about 5 mol %).

In another embodiment, the present disclosure provides a method for making a compound of formula (1)

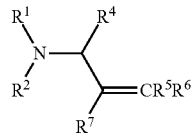

comprising (a) converting a compound of formula (2)

to a compound of formula (3)

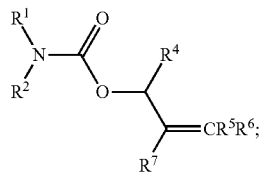

and (b) decarboxylating the compound of formula (3) to provide the compound of formula (1), where R$^1$, R$^2$, and R$^3$ are each independently selected from —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected R$^8$ groups, or R$^1$ and R$^2$ are taken together with the nitrogen atom to which they are bound to form a heterocyclic or heteroaryl ring of formula (5)

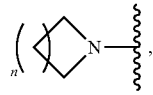

where n is an integer selected from 0, 1, 2, 3, 4, 5, 6, 7, 8, 9, 10, and 11; R$^4$ is selected from the group consisting of —H, —(C$_1$-C$_6$) alkyl, phenyl, allyl, -2-butenyl, -3-butenyl, -4-pentenyl, -2-propynyl, -2-butynyl, -3-butynyl, -2-pentynyl,

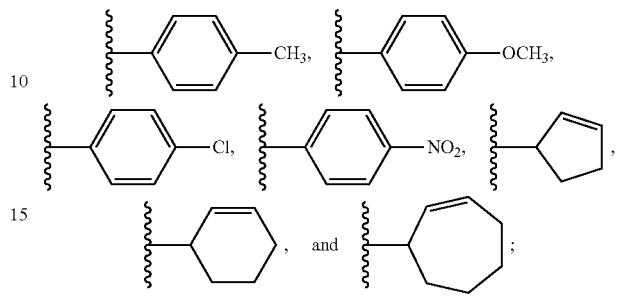

R$^5$, R$^6$, and R$^7$ are each independently selected from —H, —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected R$^8$ groups, or R$^6$ and R$^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected R$^8$ groups; R$^8$ is —OR$^{51}$, —F, —Cl, —Br, —I, phenyl, or —(C$_1$-C$_6$) alkyl; and R$^{51}$ is —(C$_1$-C$_6$) alkyl or an oxygen protecting group. In certain embodiments, R$^6$ and R$^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected R$^8$ groups; R$^8$ is —OR$^{51}$, —F, —Cl, —Br, —I, phenyl, or —(C$_1$-C$_6$) alkyl; and R$^{51}$ is —(C$_1$-C$_6$) alkyl or an oxygen protecting group.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected R$^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected R$^{52}$ groups. R$^{52}$ is selected from =O, =CH$_2$, —OR$^{53}$, —O(C$_1$-C$_6$) alkyl, —C(=O)(C$_1$-C$_6$) alkyl, and —(C$_1$-C$_6$) alkyl, where each alkyl group is either unsubstituted or substituted with 1, 2, 3, 4, or 5 independently-selected —OR$^{53}$ groups; and R$^{53}$ is —H or an oxygen protecting group. In certain embodiments, R$^{52}$ is selected from =O, =CH$_2$, —OR$^{53}$, —O(C$_1$-C$_6$) alkyl, and —(C$_1$-C$_6$) alkyl, where each alkyl group is either unsubstituted or substituted with 1, 2, 3, 4, or 5 independently-selected —OR$^{53}$ groups; and R$^{53}$ is —H or an oxygen protecting group.

In certain embodiments, the compound of formula (3) is formed by adding a compound of formula (2) to a compound of formula (93)

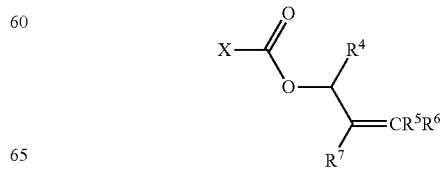

in a suitable solvent, where $R^1$, $R^2$, $R^3$, $R^4$, $R^5$, and $R^6$ and $R^7$ are as defined above and X is selected from —Cl, —Br, and —I. The reaction of the compound of formula (2) to the compound of formula (93) can be carried out in the presence of a base.

In particular embodiments, a stoichiometric excess of the compound of formula (93)

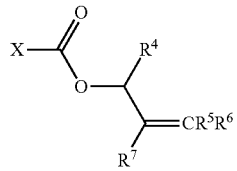

is added relative to the compound of formula (2)

to provide the compound of formula (3), where $R^1$, $R^2$, $R^3$, $R^4$, $R^5$, $R^6$, and X are defined as above. The compound of formula (93) can be added in total at the beginning of the reaction or can be added in a plurality of portions, i.e., portion-wise, throughout the course of the reaction. In certain embodiments, the compound of formula (93) is added continuously throughout the course of the reaction.

The conversion of a compound of formula (2) to a compound of formula (3) can be carried out in any suitable solvent in which the reaction can proceed. In certain embodiments, the solvent is selected from the group consisting of ether solvents, acetonitrile, benzene, N,N-dimethylformamide (DMF), dimethyl sulfoxide (DMSO), N,N-dimethylpropionamide, 1,3-dimethyl-3,4,5,6-tetrahydro-2 (1H)-pyrimidinone (DMPU), 1,3-dimethyl-2-imidazolidinone (DMI), 1,2-dimethoxyethane (DME), N,N-dimethylacetamide (DMAC), N-methylpyrrolidinone (NMP), ethyl acetate, ethyl formate, ethyl-methyl ketone, iso-butylmethylketone, formamide, hexamethylphosphoramide, methyl acetate, N-methylacetamide, N-methylformamide, nitrobenzene, nitromethane, propionitrile, sulfolane, tetramethylurea, tetrahydrofuran (THF), toluene, $CHCl_3$, $CH_2Cl_2$, 1,2-dichloroethane, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment, the solvent comprises tert-amyl alcohol. In another specific embodiment, the solvent consists essentially of tert-amyl alcohol. In another specific embodiment, the solvent is tert-amyl alcohol.

In other embodiments, in particular in embodiments regarding the heterocyclic or heteroaryl ring of formula (5), the conversion of a compound of formula (2) to a compound of formula (3) is carried out in the presence of an iodide salt. In certain embodiments, the iodide salt is present in a sub-stoichiometric amount. In certain embodiments, the iodide salt is present in a catalytic amount. The iodide salt is selected from the group consisting of NaI, KI, LiI, CsI, RuI, $MgI_2$, $CaI_2$, $NH_4I$, tetrabutylammonium iodide, and combinations of two or more thereof. In certain embodiments, the iodide salt is NaI.

In certain embodiments, n is an integer selected from 0, 1, 2, 3, 4, 5, 6, 7, 8, and 9. In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

In another embodiment, the present disclosure provides a method for making a compound of formula (1)

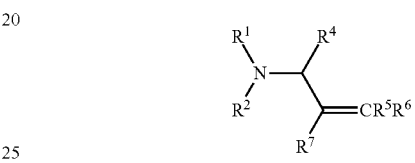

comprising contacting a compound of formula (2)

with a compound of formula (23)

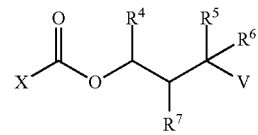

and a base in a solvent to provide a compound of formula (24)

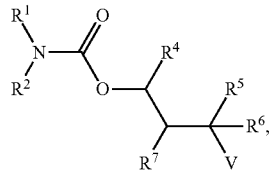

and contacting the compound of formula (24) with a transition metal catalyst to provide the compound of formula (1), where $R^1$, $R^2$, and $R^3$ are each independently selected from —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

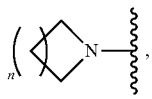

where n is an integer selected from 0, 1, 2, 3, 4, 5, 6, 7, 8, 9, 10, and 11; X is selected from —Cl, —Br, and —I; $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

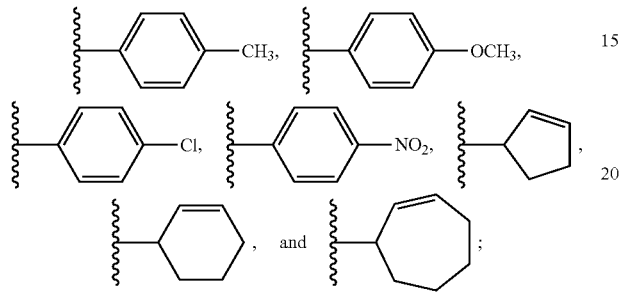

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; $R^{51}$ is —($C_1$-$C_6$) alkyl or an oxygen protecting group; and V is a leaving group.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —O($C_1$-$C_6$) alkyl, —C(=O)($C_1$-$C_6$) alkyl, and —($C_1$-$C_6$) alkyl, each alkyl group being either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —O($C_1$-$C_6$) alkyl, and —($C_1$-$C_6$) alkyl, where each alkyl group is either unsubstituted or substituted with 1, 2, 3, 4, or 5 independently-selected —$OR^{53}$ groups; and $R^{53}$ is —H or an oxygen protecting group.

In certain embodiments, the transition metal catalyst is present in a sub-stoichiometric amount. In certain embodiments, the transition metal catalyst is present in a catalytic amount. In certain embodiments, the transition metal catalyst is present in an amount of from 0.001 to 30 mol % or of any numerical value within this range. In certain embodiments, the transition metal catalyst is present in an amount of from 0.1 to 10 mol % or of any numerical value within this range (like about 5 mol %).

In another embodiment, the present disclosure provides a method for making a compound of formula (1)

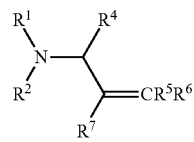

comprising contacting a compound of formula (25)

with a compound of formula (26)

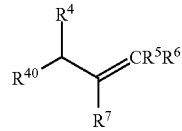

in a solvent comprising a transition metal catalyst to provide the compound of formula (1), where $R^1$ and $R^2$ are independently selected from —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

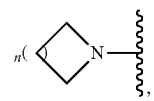

where n is an integer selected from 0, 1, 2, 3, 4, 5, 6, 7, 8, 9, 10, and 11; $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

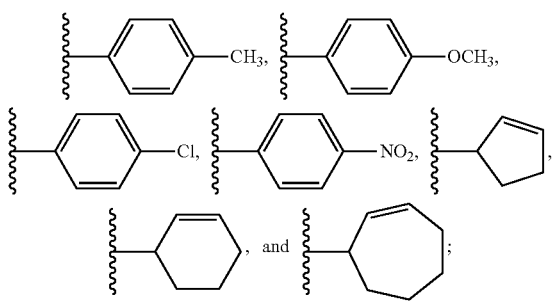

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —O($C_1$-$C_6$) alkyl, —C(=O)($C_1$-$C_6$) alkyl, and —($C_1$-$C_6$) alkyl, each alkyl group being either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —O($C_1$-$C_6$) alkyl, and —($C_1$-$C_6$) alkyl, where each alkyl group is either unsubstituted or substituted with 1, 2, 3, 4, or 5 independently-selected —$OR^{53}$ groups; and $R^{53}$ is —H or an oxygen protecting group.

In certain embodiments, $R^{40}$ is selected from —OC(O)$CH_3$ and —N($CH_3$)$_2$ while, in other embodiments, $R^{40}$ is —O(C)OX and X is —Cl, —Br, or —I.

In one embodiment, the compound of formula (25) is contacted with a compound of formula (23)

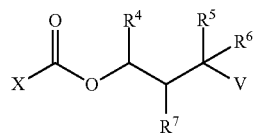

in a solvent in the presence of a transition metal catalyst to provide a compound of formula (1). X, $R^4$, $R^5$, $R^6$, $R^7$, and V are as defined above. In one aspect of this embodiment, the contacting is done in the presence of a base.

In another embodiment, the compound of formula (25) is contacted with a compound of formula (48)

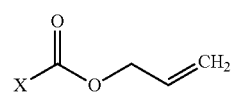

and a transition metal catalyst to provide a compound of formula (1).

In another embodiment, the compound of formula (25) is contacted with a compound of formula (46)

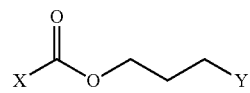

and a transition metal catalyst to provide a compound of formula (1). X is selected from —Cl, —Br, and —I. Y is a leaving group. In certain embodiments, the contacting of the compound of formula (25) with the compound of formula (46) is carried out under condition or in the presence of a reagent that promotes elimination of the leaving group, Y. In one aspect of this embodiment, the reagent is a base. Where the reagent is a base, it can, for example, be selected from the group consisting of NaOH, KOH, sodium tert-butoxide (tert-BuONa), potassium tert-butoxide (tert-BuOK), lithium di-iso-propylamide, sodium hydride, tert-butyl lithium, $LiAlH_4$, $AlCl_3$, triethylamine, sodium ethoxide, lithium diethyl amide (LiN(Et)$_2$), potassium acetate (KOAc), and combinations of two or more thereof. The reagent can also be, e.g., ethylmagnesium bromide and tributyltin hydride, in particular where there are two leaving groups which are both —Br. In another aspect, elimination of the leaving group Y is promoted by heat. In a further aspect, elimination of the leaving group Y is promoted by exposure to light of an appropriate wavelength.

In a further embodiment, the compound of formula (25) is contacted with a compound of formula (19)

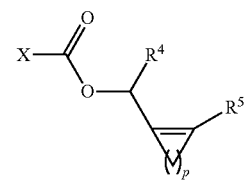

and a transition metal catalyst to provide a compound of formula (27)

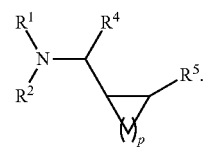

In another embodiment, the compound of formula (25) is contacted with a compound of formula (29)

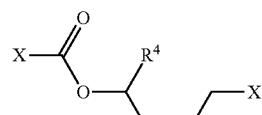

and a transition metal catalyst to provide a compound of formula (27)

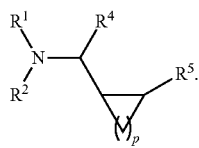

Each X is independently selected from —Cl, —Br, and —I. $R^1$, $R^2$, $R^4$, and $R^5$ are as defined above; p is an integer selected from 1, 2, 3, 4, 5, 6, and 7.

Accordingly, the present disclosure further provides a method for making a compound of formula (27)

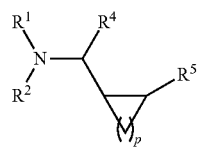

comprising
(a) contacting a compound of formula (2)

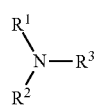

with a compound of formula (19)

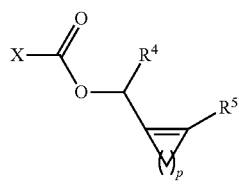

to provide a compound of formula (18)

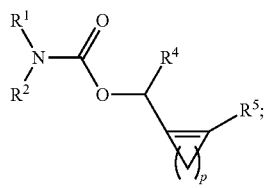

(b) contacting the compound of formula (18) with a transition metal catalyst to provide a compound of formula (17)

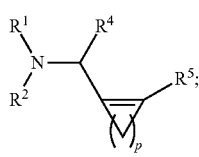

and
(c) hydrogenating the compound of formula (17), to provide the compound of formula (27), where $R^1$, $R^2$, and $R^3$ are each independently selected from —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

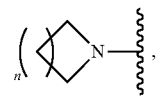

where n is an integer selected from 0, 1, 2, 3, 4, 5, 6, 7, 8, 9, 10, and 11; and X is selected from —Cl, —Br, and —I; $R^5$ is selected from —H, —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups; $R^8$ is —$OR^{51}$, —F, —Cl, —Br, —I, phenyl, or —$(C_1$-$C_6)$ alkyl; $R^{51}$ is —$(C_1$-$C_6)$ alkyl or an oxygen protecting group; and p is an integer selected from 1, 2, 3, 4, 5, 6, and 7.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —$O(C_1$-$C_6)$ alkyl, —$C(=O)(C_1$-$C_6)$ alkyl, and —$(C_1$-$C_6)$ each alkyl either being unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —$O(C_1$-$C_6)$ alkyl, and —$(C_1$-$C_6)$ alkyl, where each alkyl group is either unsubstituted or substituted with 1, 2, 3, 4, or 5 independently-selected —$OR^{53}$ groups; and $R^{53}$ is —H or an oxygen protecting group.

The present disclosure also provides a method for making a compound of formula (28)

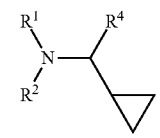

comprising
(a) contacting a compound of formula (2)

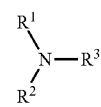

with a compound of formula (29)

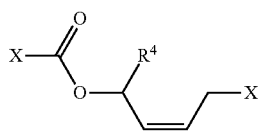

to provide a compound of formula (30)

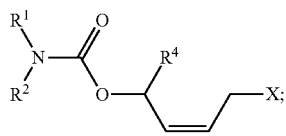

(b) contacting the compound of formula (30) with a transition metal catalyst to provide a compound of formula (31)

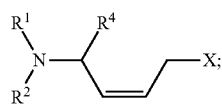

and (c) contacting the compound of formula (31) with a zinc-containing reagent, e.g., zinc[0], in the presence of an iodide salt to provide the compound of formula (28), where $R^1$, $R^2$, and $R^3$ are each independently selected from —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

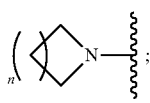

where n is an integer selected from 0, 1, 2, 3, 4, 5, 6, 7, 8, 9, 10, and 11; X is selected from —Cl, —Br, and —I; $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

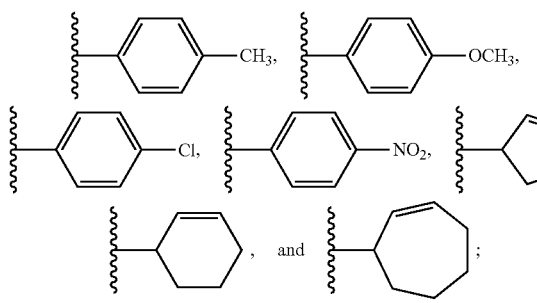

$R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —O($C_1$-$C_6$) alkyl, —C(=O)($C_1$-$C_6$) alkyl, and —($C_1$-$C_6$) alkyl, each alkyl group being either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —O($C_1$-$C_6$) alkyl, and —($C_1$-$C_6$) alkyl, where each alkyl group is either unsubstituted or substituted with 1, 2, 3, 4, or 5 independently-selected —$OR^{53}$ groups; and $R^{53}$ is —H or an oxygen protecting group.

In certain embodiments, the iodide salt is present in a sub-stoichiometric amount. In certain embodiments, the iodide salt is present in a catalytic amount. In certain embodiments, the iodide salt can be selected from, e.g., NaI, KI, LiI, CsI, RuI, $MgI_2$, $CaI_2$, $NH_4I$, tetrabutylammonium iodide, and combinations of two or more thereof. In certain embodiments, the iodide salt is NaI.

The present disclosure also provides a method for making a compound of formula (32)

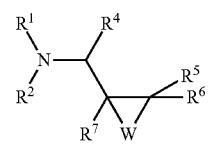

comprising (a) converting a compound of formula (2)

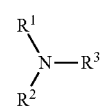

to a compound of formula (3)

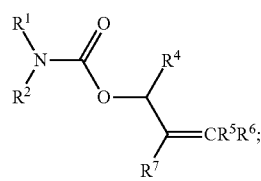

(b) contacting the compound of formula (3) with a transition metal catalyst to provide a compound of formula (1)

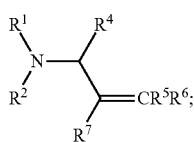

and (c) converting the compound of formula (1) to the compound of formula (32), where $R^1$, $R^2$, and $R^3$ are each independently selected from —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

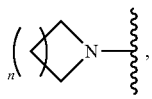

where n is an integer selected from 0, 1, 2, 3, 4, 5, 6, 7, 8, 9, 10, and 11; $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

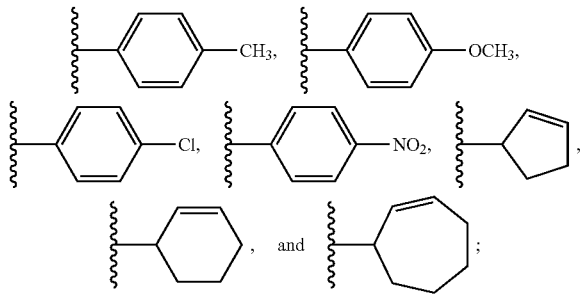

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; $R^{51}$ is —($C_1$-$C_6$) alkyl or an oxygen protecting group; W is $CH_2$, O, or $NR^{41}$; $R^{41}$ is selected from —H, tert-butyl, —$CH_2CH_2OCH_2CH_3$, —C(O)$OCH_3$, —P(O)($OCH_2CH_3$)$_2$, phthalimide, and —S(O)$_2$Z; and Z is selected from tert-butyl, phenyl, toluyl, para-methoxyphenyl, ortho-nitrophenyl, 2,4,6-trimethylphenyl, and —$CH_2CH_2Si(CH_3)_3$.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —O($C_1$-$C_6$) alkyl, —C(=O)($C_1$-$C_6$) alkyl, and —($C_1$-$C_6$) alkyl, each alkyl being either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —O($C_1$-$C_6$) alkyl, and —($C_1$-$C_6$) alkyl, where each alkyl group is either unsubstituted or substituted with 1, 2, 3, 4, or 5 independently-selected —$OR^{53}$ groups; and $R^{53}$ is —H or an oxygen protecting group.

In a further embodiment, the present disclosure provides a method for making a compound of formula (39)

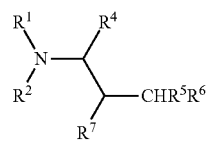

comprising
(a) converting a compound of formula (2)

to a compound of formula (3)

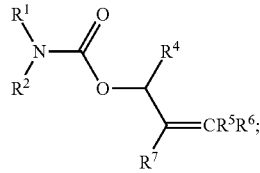

(b) contacting the compound of formula (3) with a transition metal catalyst to provide a compound of formula (1)

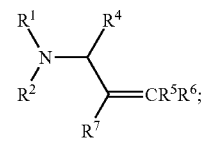

and
(c) hydrogenating the compound of formula (1) to provide the compound of formula (39), where $R^1$, $R^2$, and $R^3$ are each independently selected from —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

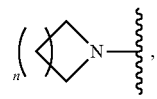

where n is an integer selected from 0, 1, 2, 3, 4, 5, 6, 7, 8, 9, 10, and 11; R⁴ is selected from the group consisting of —H, —(C₁-C₆) alkyl, phenyl, allyl, -2-butenyl, -3-butenyl, -4-pentenyl, -2-propynyl, -2-butynyl, -3-butynyl, -2-pentynyl,

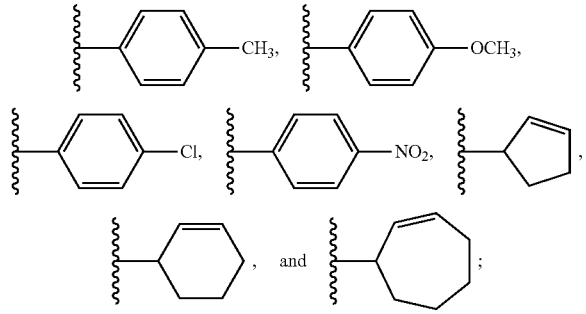

R⁵, R⁶, and R⁷ are each independently selected from —H, —(C₁-C₆) alkyl, —(C₂-C₆) alkenyl, and —(C₂-C₆) alkynyl, each alkyl, alkenyl, and alkynyl being unsubstituted or substituted with 1, 2, 3, 4, or 5 independently-selected R⁸ groups, or R⁶ and R⁷ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected R⁸ groups; R⁸ is —OR⁵¹, —F, —Cl, —Br, —I, phenyl, or —(C₁-C₆) alkyl; and R⁵¹ is —(C₁-C₆) alkyl or an oxygen protecting group. In certain embodiments, R⁶ and R⁷ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected R⁸ groups; R⁸ is —OR⁵¹, —F, —Cl, —Br, —I, phenyl, or —(C₁-C₆) alkyl; and R⁵¹ is —(C₁-C₆) alkyl or an oxygen protecting group.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected R⁵² groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected R⁵² groups. R⁵² is selected from =O, =CH₂, —OR⁵³, —O(C₁-C₆) alkyl, —C(=O)(C₁-C₆) alkyl, and —(C₁-C₆) alkyl, each alkyl being either unsubstituted or substituted with 1, 2, 3, 4, or 5 independently-selected —OR⁵³ groups; and R⁵³ is —H or an oxygen protecting group. In certain embodiments, R⁵² is selected from =O, =CH₂, —OR⁵³, —O(C₁-C₆) alkyl, and —(C₁-C₆) alkyl, where each alkyl group is either unsubstituted or substituted with 1, 2, 3, 4, or 5 independently-selected —OR⁵³ groups; and R⁵³ is —H or an oxygen protecting group.

In another embodiment, the disclosure provides a method for making a compound of formula (40)

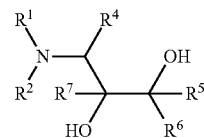

comprising (a) converting a compound of formula (2)

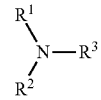

to a compound of formula (3)

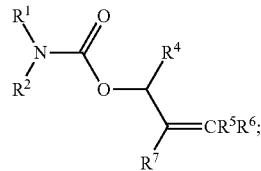

(b) contacting the compound of formula (3) with a transition metal catalyst to provide a compound of formula (1)

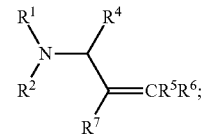

and (c) oxidizing the compound of formula (1) to provide the compound of formula (40), where R¹, R², and R³ are each independently selected from —(C₁-C₆) alkyl, —(C₂-C₆) alkenyl, and —(C₂-C₆) alkynyl, each alkyl, alkenyl, and alkynyl being unsubstituted or substituted with 1, 2, 3, 4, or 5 independently-selected R⁸ groups, or R¹ and R² are taken together with the nitrogen atom to which they are bound to form a heterocyclic or heteroaryl ring of formula (5)

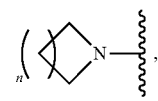

where n is an integer selected from 0, 1, 2, 3, 4, 5, 6, 7, 8, 9, 10, and 11; R⁴ is selected from the group consisting of —H, —(C₁-C₆) alkyl, phenyl, allyl, -2-butenyl, -3-butenyl, -4-pentenyl, -2-propynyl, -2-butynyl, -3-butynyl, -2-pentynyl,

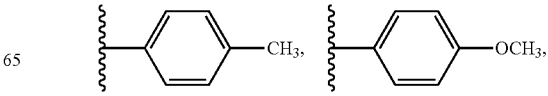

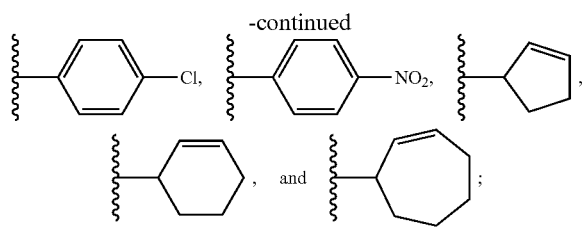

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —O($C_1$-$C_6$) alkyl, —C(=O)($C_1$-$C_6$) alkyl, and —($C_1$-$C_6$) alkyl, each alkyl being either unsubstituted or substituted with 1, 2, 3, 4, or 5 independently-selected —$OR^{53}$ groups; and $R^{53}$ is —H or an oxygen protecting group. In certain embodiments, $R^{52}$ is selected from =O, =$CH_2$, —$OR^{53}$, —O($C_1$-$C_6$) alkyl, and —($C_1$-$C_6$) alkyl, where each alkyl group is either unsubstituted or substituted with 1, 2, 3, 4, or 5 independently-selected —$OR^{53}$ groups; and $R^{53}$ is —H or an oxygen protecting group.

The methods disclosed herein are readily adapted for the synthesis of clinically and commercially important compounds including, but not limited to, naloxone, naltrexone, noroxymorphone, noroxycodone, buprenorphine, and cabergoline. In particular embodiments, the methods disclosed herein are useful for specific conversions, e.g., the preparation of naloxone from oxymorphone, and for incorporation into overall processes, e.g., the preparation of naloxone from oripavine. The methods disclosed herein are also readily adapted to the synthesis of such clinically and commercially important compounds from morphine, codeine, and thebaine.

Therefore, in another embodiment, the present disclosure provides a method for making a compound of formula (41)

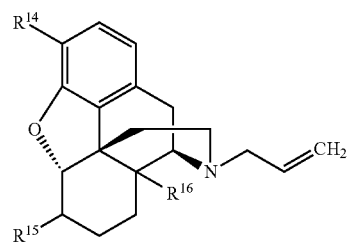

comprising contacting a compound of formula (42)

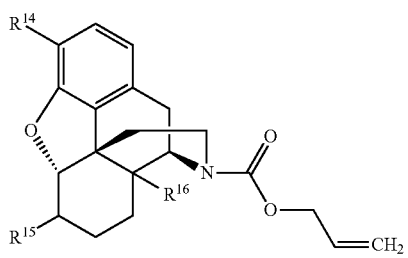

with a transition metal catalyst in a solvent to provide the compound of formula (41), where $R^{14}$ and $R^{16}$ are each independently selected from —OH, —H, and —$OR^{17}$; $R^{15}$ is selected from —OH, —H, —$OR^{17}$, =O, and =$CH_2$, and $R^{17}$ is an oxygen protecting group.

In another aspect of this embodiment, the preceding method further comprises reacting a compound of formula (45)

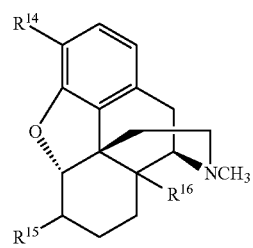

with a compound of formula (48)

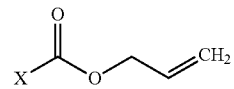

in a solvent comprising a base to provide the compound of formula (95)

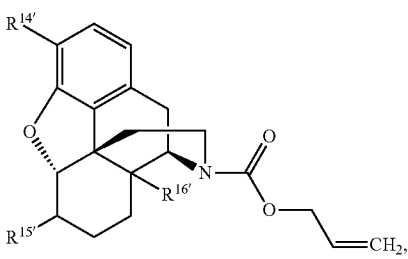

where $R^{14}$ and $R^{16}$ are each independently selected from —OH, —H, and —OR$^{17}$; $R^{15}$ is selected from —OH, —H, —OR$^{17}$, =O, and =CH$_2$; $R^{17}$ is an oxygen protecting group; and X is selected from —Cl, —Br, and —I.

As used throughout herein, it is to be understood that $R^{14'}$, $R^{15'}$, and $R^{16'}$ include not only $R^{14}$, $R^{15}$, and $R^{16}$, respectively, but also, when an $R^{14}$, $R^{15}$, and/or $R^{16}$ group is present as an —OH group or contains an —OH group, the reaction product of a compound of formula (48) or its equivalent, e.g., an "allyl haloformate equivalent," with that —OH group to form a group comprising a carbonate. Thus, $R^{14'}$, $R^{15'}$, and $R^{16'}$ groups include, in addition to the respective $R^{14}$, $R^{15}$, and $R^{16}$ groups, such carbonate-containing reaction products. Even further, certain reaction pathways described herein convert the carbonate portion of the carbonate-containing reaction product into an ether group. Thus, $R^{14'}$, $R^{15'}$, and $R^{16'}$ further include such ether-containing reaction products.

It is also to be understood that when $R^{14}$ is selected to be a particular moiety that is not an —OH group, then $R^{14'}$ is also that particular $R^{14}$ moiety. Likewise, it is to be understood that when $R^{15}$ is selected to be a particular moiety that is not an —OH group, then $R^{15'}$ is also that particular $R^{15}$ moiety. Likewise, it is to be understood that when $R^{16}$ is selected to be a particular moiety that is not an —OH group, then $R^{16'}$ is also that particular $R^{16}$ moiety.

In embodiments where an $R^{14'}$, $R^{15'}$, and/or $R^{16'}$ group(s) is or contains a carbonate-containing group formed from an —OH group, that carbonate-containing group can be converted back to the —OH group. Conversion of the carbonate-containing group to the —OH group can be carried out in the presence of a suitable base. Alternatively, when an $R^{14'}$, $R^{15'}$, and/or $R^{16'}$ group is an allyl carbonate, that allyl carbonate can first be converted into an —O-allyl group through a transition metal catalyzed decarboxylation reaction, in accordance with the present disclosure. Thereafter, the —O-allyl group can be converted into an —OH group in the presence of a suitable allyl scavenger, as described herein.

The reaction of the compound of formula (45) with a compound of formula (48) can be carried out in any suitable solvent in which the reaction can proceed. In certain embodiments, the solvent is selected from the group consisting of ether solvents, acetonitrile, benzene, DMF, DMSO, N,N-dimethylpropionamide, DMPU, DMI, DME, DMAC, NMP, ethyl acetate, ethyl formate, ethyl-methyl ketone, iso-butylmethylketone, formamide, hexamethylphosphoramide, methyl acetate, N-methylacetamide, N-methylformamide, nitrobenzene, nitromethane, propionitrile, sulfolane, tetramethylurea, THF, toluene, CHCl$_3$, CH$_2$Cl$_2$, 1,2-dichloroethane, THF, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment, the solvent comprises tert-amyl alcohol. In another specific embodiment, the solvent consists essentially of tert-amyl alcohol. In another specific embodiment, the solvent is tert-amyl alcohol.

In other embodiments, the reaction of the compound of formula (45) with the compound of formula (48) is carried out in the presence of an iodide salt. In certain embodiments, the iodide salt is present in a sub-stoichiometric amount. In certain embodiments, the iodide salt is present in a catalytic amount. The iodide salt is selected from the group consisting of NaI, KI, LiI, CsI, RuI, MgI$_2$, CaI$_2$, NH$_4$I, tetrabutylammonium iodide, and combinations of two or more thereof. In certain embodiments, the iodide salt is NaI.

In other embodiments, a stoichiometric excess of the compound of formula (48) is added relative to the compound of formula (45) to provide a compound of formula (95). The compound of formula (48) can be added in total at the beginning of the reaction or portion-wise throughout the course of the reaction (e.g., see Examples 3 and 18 below). In certain embodiments, the compound of formula (48) is added continuously throughout the course of the reaction.

The present disclosure also provides for an alternative method of making a compound of formula (41)

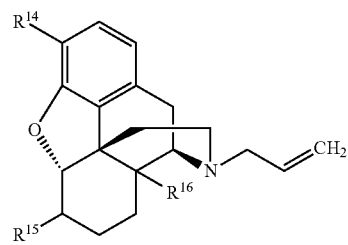

which comprises
(a) reacting a compound of formula (45)

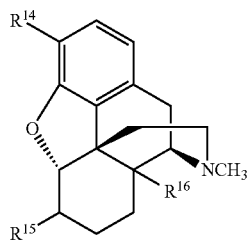

with a compound of formula (46)

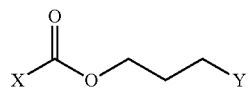

to provide a compound of formula (47)

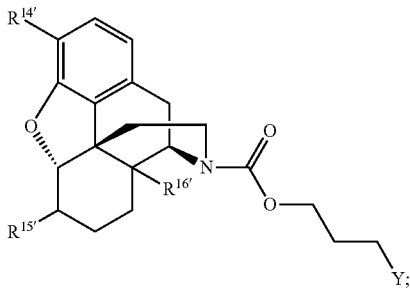

(b) optionally, converting the compound of formula (47) to the compound of formula (94)

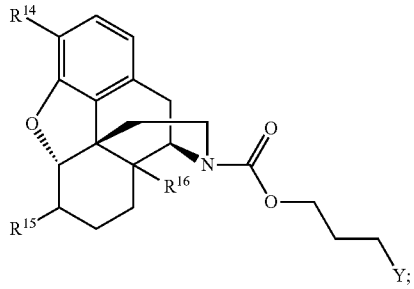

(c) converting the compound of formula (47) or the compound of formula (94) to a compound of formula (42)

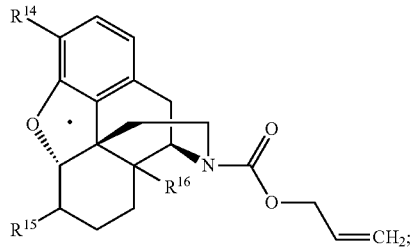

and (d) converting the compound of formula (42) to the compound of formula (41), where $R^{14}$, $R^{14'}$, $R^{15}$, $R^{15'}$, $R^{16}$, $R^{16'}$, X, and Y are defined as above.

In one embodiment, the reacting of the compound of formula (45) with the compound of formula (46) is carried out in the presence of a base.

In another embodiment, the converting of the compound of formula (47) or the compound of formula (94) to a compound of formula (42) is carried out under conditions and/or in the presence of a reagent that promotes elimination of the leaving group, Y. In one aspect of this embodiment, the reagent is a base. Where the reagent is a base, it can, for example, be selected from the group consisting of NaOH, KOH, sodium tert-butoxide (tert-BuONa), potassium tert-butoxide (tert-BuOK), lithium di-iso-propylamide, sodium hydride, tert-butyl lithium, $LiAlH_4$, $AlCl_3$, triethylamine, sodium ethoxide, lithium diethyl amide ($LiN(Et)_2$), potassium acetate (KOAc), and combinations of two or more thereof. The reagent can also be, e.g., ethylmagnesium bromide and tributyltin hydride, in particular where there are two leaving groups which are both —Br. In another aspect, elimination of the leaving group Y is promoted by heat. In a further aspect, elimination of the leaving group Y is promoted by exposure to light of an appropriate wavelength.

In particular embodiments of the above methods, the compound of formula (45) is a compound of formula (51)

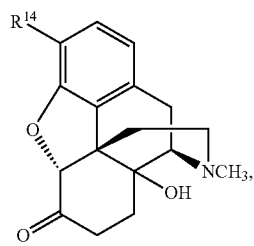

which can be prepared by oxidizing a compound of formula (52)

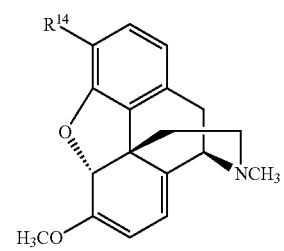

to provide a compound of formula (53)

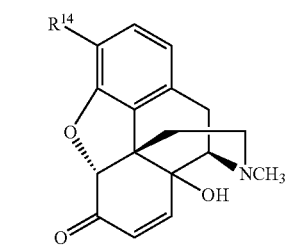

and hydrogenating the compound of formula (53) to provide the compound of formula (51). In certain embodiments of this method, $R^{14}$ is —OH while, in other embodiments, $R^{14}$ is —OCH$_3$.

The present disclosure also provides a method for making a compound of formula (54)

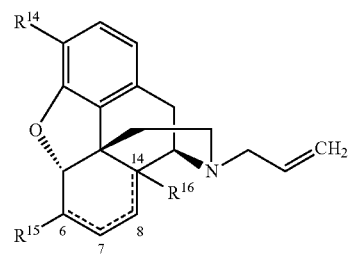

comprising contacting a compound of formula (55)

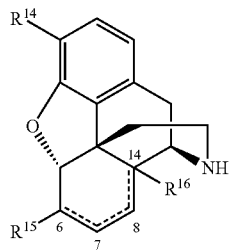

with a compound of formula (56)

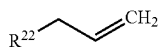

in a solvent comprising a base and a transition metal catalyst to provide the compound of formula (54), where $R^{14}$ and $R^{16}$ are each independently selected from —OH, —H, and —OR$^{17}$; the 6,7 ----- bond, the 7,8 ----- bond, and the 8,14 ----- bond are each independently a single bond or a double bond, with the provisos that (1) if the 6,7 ----- bond is a double bond, then the 7,8 ----- bond is a single bond, (2) if the 7,8 ----- bond is a double bond, then the 6,7 ----- and 8,14 ----- bonds are each a single bond, and (3) if the 8,14 ----- bond is a double bond, then the 7,8 ----- bond is a single bond and $R^{16}$ is not present. $R^{15}$ is selected from —OH, —H, —OR$^{17}$, =O, and =CH$_2$ with the proviso that if the 6,7 ----- bond is a double bond, then $R^{15}$ is selected from —OH, —H, and —OR$^{17}$; and $R^{17}$ is an oxygen protecting group. $R^{22}$ is selected from —N(CH$_3$)$_2$, —OC(O)CH$_3$, and —OC(O)X; and X is selected from —Cl, —Br, and —I. In one embodiment, $R^{22}$ is selected from —N(CH$_3$)$_2$ and —OC(O)CH$_3$. In another embodiment, $R^{22}$ is —OC(O)X.

In other embodiments, the compound of formula (54) can be prepared by contacting the compound of formula (55) with a compound of formula (46) in the presence of a transition metal catalyst. In other embodiments, the compound of formula (54) can be prepared by contacting the compound of formula (55) with a compound of formula (48) in the presence of a transition metal catalyst.

In another specific aspect, the present disclosure also provides a method for making a compound of formula (57)

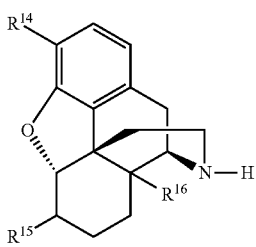

comprising contacting a compound of formula (42)

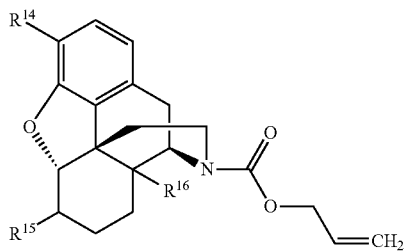

with a transition metal catalyst in the presence of an allyl scavenger, to provide the compound of formula (57), where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In one embodiment, the allyl scavenger can be selected from those known in the art, e.g., from among the following illustrative examples:

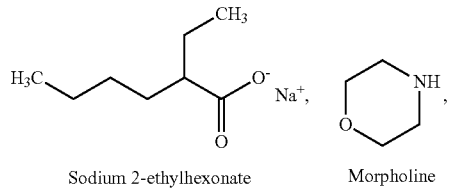

Sodium 2-ethylhexonate    Morpholine

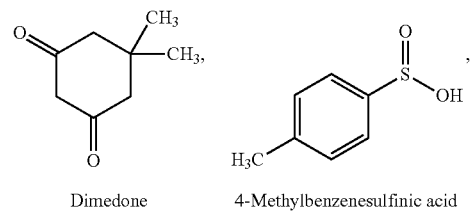

Dimedone    4-Methylbenzenesulfinic acid

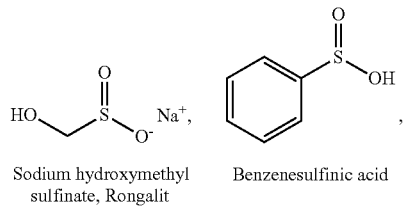

Sodium hydroxymethyl    Benzenesulfinic acid
sulfinate, Rongalit

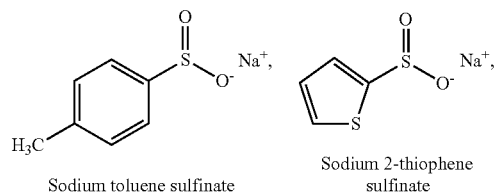

Sodium toluene sulfinate    Sodium 2-thiophene sulfinate

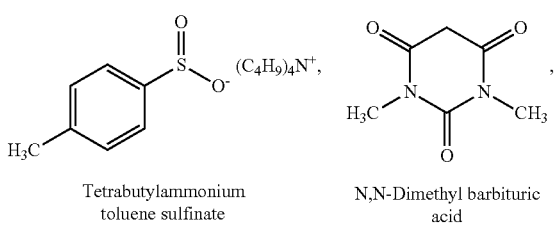

Tetrabutylammonium    N,N-Dimethyl barbituric
toluene sulfinate    acid

-continued

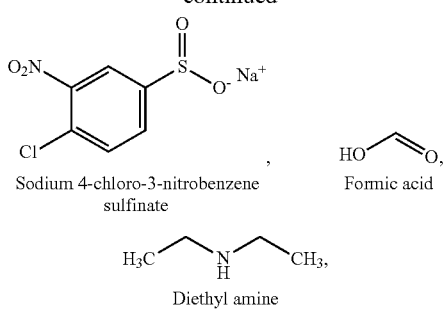

Sodium 4-chloro-3-nitrobenzene sulfinate, Formic acid, Diethyl amine methanol, ethanol, and combinations of two or more thereof. In another embodiment, the allyl scavenger can be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof. In another embodiment, the allyl scavenger is compound (146)

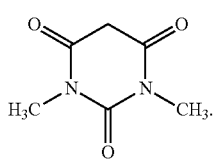

(146)

The present disclosure also provides a method for making a compound of formula (62)

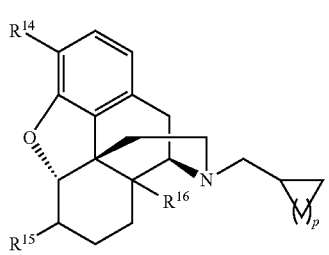

comprising (a) contacting a compound of formula (45)

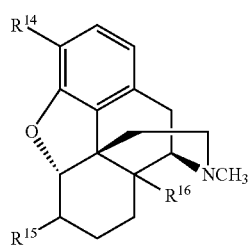

with a compound of formula (63)

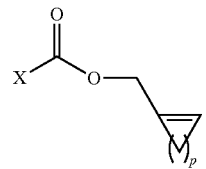

in a solvent comprising a base to provide a compound of formula (64)

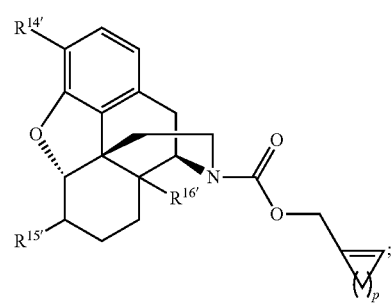

(b) optionally, converting the carbonate groups present at $R^{14'}$, $R^{15'}$, and $R^{16'}$ to —OH groups to provide a compound of formula (96)

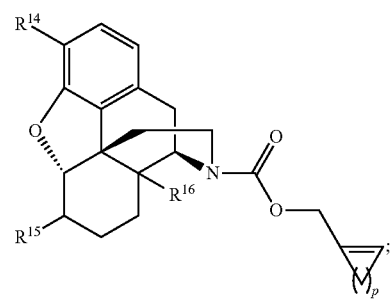

(c) contacting the compound of formula (64) or the compound of formula (96) with a transition metal catalyst to provide a compound of formula (65)

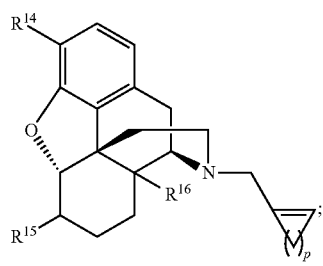

and (d) hydrogenating the compound of formula (65) to provide the compound of formula (62), where $R^{14}$, $R^{14'}$, $R^{15}$, $R^{15'}$, $R^{16}$, $R^{16'}$, and X are defined as above and p is an integer selected from 1, 2, 3, 4, 5, 6, and 7.

In another embodiment, the present disclosure provides a method for making a compound of formula (66)

the method comprising
(a) contacting a compound of formula (45)

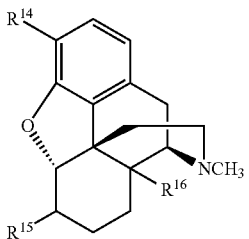

with a compound of formula (67)

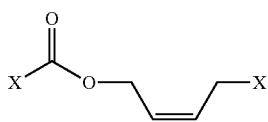

in a solvent comprising a base to provide a compound of formula (68)

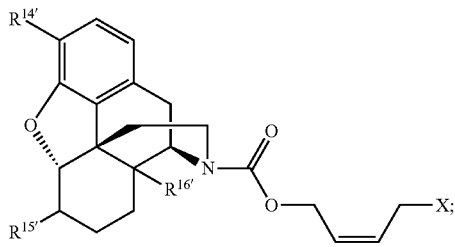

(b) optionally, converting the carbonate groups present at $R^{14'}$, $R^{15'}$, and $R^{16'}$ to —OH groups to provide a compound of formula (97)

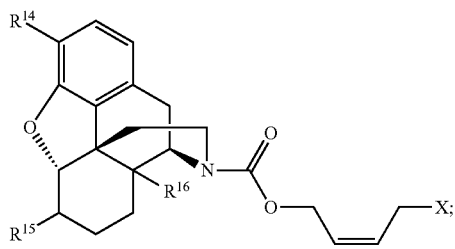

(c) contacting the compound of formula (68) or the compound of formula (97) with a transition metal catalyst to provide a compound of formula (69)

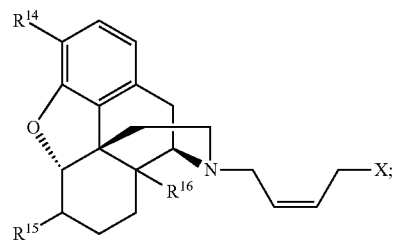

and (d) contacting the compound of formula (69) with a zinc-containing reagent, e.g., zinc[0], in the presence of an iodide salt to provide the compound of formula (66), where $R^{14}$, $R^{14'}$, $R^{15}$, $R^{15'}$, $R^{16}$, $R^{16'}$, and X are defined as above.

The reaction of the compound of formula (45) with a compound of formula (63) or with a compound of formula (67) can be carried out in any suitable solvent in which the reaction can proceed. In certain embodiments, the solvent is selected from the group consisting of ether solvents, acetonitrile, benzene, DMF, DMSO, N,N-dimethylpropionamide, DMPU, DMI, DME, DMAC, NMP, ethyl acetate, ethyl formate, ethyl-methyl ketone, iso-butylmethylketone, formamide, hexamethylphosphoramide, methyl acetate, N-methylacetamide, N-methylformamide, nitrobenzene, nitromethane, propionitrile, sulfolane, tetramethylurea, THF, toluene, $CHCl_3$, $CH_2Cl_2$, 1,2-dichloroethane, THF, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment, the solvent comprises tert-amyl alcohol. In another specific embodiment, the solvent consists essentially of tert-amyl alcohol. In another specific embodiment, the solvent is tert-amyl alcohol.

In other embodiments, the reaction of the compound of formula (45) with the compound of formula (63) or with the compound of formula (67) is carried out in the presence of an iodide salt. In certain embodiments, the iodide salt is present in a sub-stoichiometric amount. In certain embodiments, the iodide salt is present in a catalytic amount. The iodide salt is selected from the group consisting of NaI, KI, LiI, CsI, RuI, $MgI_2$, $CaI_2$, $NH_4I$, tetrabutylammonium iodide, and combinations of two or more thereof. In certain embodiments, the iodide salt is NaI.

The present disclosure also provides a composition comprising a compound of formula (42)

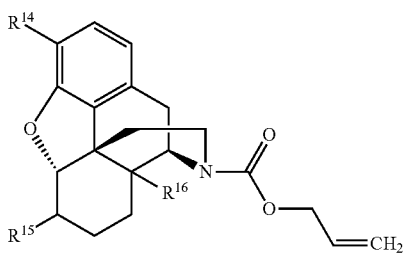

and a transition metal catalyst, where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In another embodiment, the present disclosure also provides a composition prepared by admixing a compound of formula (42)

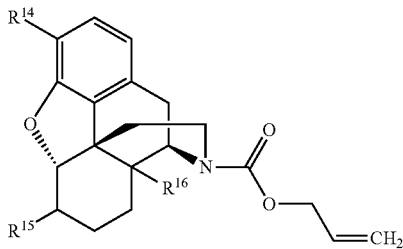

and a transition metal catalyst, where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In other embodiments, the present disclosure also provides for a compound prepared by any method of the disclosure.

4. DETAILED DESCRIPTION

The present disclosure provides processes for the preparation of N-allyl compounds from tertiary amines. The disclosed processes involve N-dealkylation of the tertiary amine to provide an N-allyl carbamate intermediate that, in turn, is decarboxylated in a transition metal-catalyzed reaction to provide an N-allyl product. The tertiary amines used as substrates in the presently disclosed reactions, methods, and processes also include compounds comprising the structural elements of compounds of formula (2) including, without limitation, opioid compounds.

Therefore, for example, in particular embodiments the present disclosure provides methods for the conversion of oxymorphone to naloxone, and processes for the conversion of oripavine to naloxone that comprise the transition metal-catalyzed reactions disclosed herein. In certain embodiments, the present disclosure provides "one pot" processes for the conversion of oxymorphone to naloxone, and "one pot" processes for the conversion of oripavine to naloxone that comprise the transition metal-catalyzed reactions disclosed herein.

In particular embodiments, the present disclosure provides methods for the conversion of oxymorphone to naltrexone, and processes for the conversion of oripavine to naltrexone that comprise the transition metal-catalyzed reactions disclosed herein. In certain embodiments, the present disclosure provides "one pot" processes for the conversion of oxymorphone to naltrexone, and "one pot" processes for the conversion of oripavine to naltrexone that comprise the transition metal-catalyzed reactions disclosed herein.

In further embodiments, the present disclosure provides methods for the conversion of oxymorphone to noroxymorphone, and processes for the conversion of oripavine to noroxymorphone that comprise the transition metal-catalyzed reactions disclosed herein. In certain embodiments, the present disclosure provides "one pot" processes for the conversion of oxymorphone to noroxymorphone, and "one pot" processes for the conversion of oripavine to noroxymorphone that comprise the transition metal-catalyzed reactions disclosed herein.

In a further embodiment, the present disclosure provides methods for the conversion of naloxone to noroxymorphone.

In other embodiments, the present disclosure provides for a compound prepared by any method of the disclosure.

4.1 Definitions

As used herein, the following terms are intended to have the following meanings:

"—(C$_1$-C$_6$) alkyl" as used herein means a straight or branched hydrocarbon chain having 1, 2, 3, 4, 5, or 6 carbon atoms that can contain or consist of a carbocyclic group. Representative straight chain —(C$_1$-C$_6$) alkyls include methyl, -ethyl, -n-propyl, -n-butyl, -n-pentyl and -n-hexyl. Representative branched chain —(C$_1$-C$_6$) alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, methyl cyclopropyl, methyl cyclobutyl, and the like.

"—(C$_2$-C$_6$) alkyl" as used herein means a straight or branched hydrocarbon chain having 2, 3, 4, 5, or 6 carbon atoms that can contain a cyclic carbocyclic group. Representative straight chain —(C$_2$-C$_6$) alkyls include -ethyl, -n-propyl, -n-butyl, -n-pentyl and -n-hexyl. Representative branched chain —(C$_2$-C$_6$) alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, methyl cyclopropyl, methyl cyclobutyl, and the like.

"—(C$_1$-C$_4$) alkyl" as used herein means a straight or branched hydrocarbon chain having 1, 2, 3, or 4 carbon atoms that can contain a cyclic carbocyclic group. Representative straight chain —(C$_1$-C$_4$) alkyls include methyl, -ethyl, -n-propyl, and -n-butyl. Representative branched chain —(C$_1$-C$_4$) alkyls include -iso-propyl, -sec-butyl, -iso-butyl, -tert-butyl, methyl cyclopentyl, and the like.

"—(C$_2$-C$_6$) alkenyl" as used herein means a straight chain or branched hydrocarbon that can contain a cyclic carbocyclic group, having 2, 3, 4, 5, or 6 carbon atoms and including at least one carbon-carbon double bond. Representative straight chain and branched —(C$_2$-C$_6$) alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—(C$_2$-C$_6$) alkynyl" as used herein means a straight chain or branched non-cyclic hydrocarbon having 2, 3, 4, 5, or 6 carbon atoms and including at least one carbon-carbon triple bond. Representative straight chain and branched —($C_2$-$C_6$) alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"Carbocyclic" as used herein means a ring structure in which all of the ring atoms are carbon. A carbocyclic group can be saturated or unsaturated. An unsaturated carbocyclic group can contain 1, 2, 3, or 4 double bonds or 1, 2, 3, or 4 triple bonds. Representative carbocyclic groups include cyclopropyl, cyclopropenyl, cyclobutyl, cyclobutenyl, cyclopentyl, cyclopentenyl, cyclohexyl, cyclohexenyl, and the like.

"Aryl" as used herein means a $C_6$-$C_{14}$ mono- or polycyclic aromatic ring system. Exemplary aryl groups include but are not limited to phenyl, naphthyl, anthryl, phenanthryl, and biphenyl groups.

"-(3- to 7-membered)heterocycle" or "-(3- to 7-membered)heterocyclo" as used herein means a 3-, 4-, 5-, 6-, or 7-membered monocyclic heterocyclic ring which is either saturated, unsaturated non-heteroaryl, or heteroaryl. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"Heteroaryl" as used herein encompasses aromatic heterocycle rings that are -(5- to 10-membered)heteroaryl or -(5- or 6-membered)heteroaryl.

"-(5- to 10-membered)heteroaryl" as used herein means an aromatic heterocycle ring of 5, 6, 7, 8, 9, or 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" as used herein means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"Halogen" as used herein means —F, —Cl, —Br, or —I. In certain embodiments, only a subset of the halogens are employed, e.g., the halogen can be selected from —Cl, —Br, and —I.

"Leaving group" as used herein means an atom, a group of atoms, or a molecular fragment that is detached, eliminated, or removed from the rest of a molecule during a reaction, e.g., a group that is displaced in a substitution reaction or elimination reaction. Representative, non-limiting examples of such leaving groups include —Cl, —Br, —I, —OS(O)$_2$C$_4$F$_9$, —OS(O)$_2$CF$_3$, —OS(O)$_2$F, -para-toluene sulfonate, and —OS(O)$_2$CH$_3$. In certain embodiments, the leaving group is a halogen selected from —Cl, —Br, and —I. In other embodiments, the leaving group is —Br.

"Oxygen protecting group" as used herein means an atom, a group of atoms, or a molecular fragment group introduced onto a molecule by chemical modification that is capable of modifying the reactivity of an oxygen atom, particularly that of a hydroxyl group, in order to obtain chemoselectivity in a subsequent chemical reaction and which, after the reaction for which protection is employed, can be removed without disturbing the remainder of the molecule. Representative, non-limiting examples of such oxygen protecting groups include allyl, acetyl, benzoyl, benzyl, β-methoxyethoxymethyl, dimethoxytrityl, methoxymethyl, para-methoxybenzyl, methylthiomethyl, pivaloyl, tetrahydropyranyl, trityl, silyl (trimethylsilyl, tert-butyldimethylsilyl, tert-butyldimethylsilyloxymethyl, and tri-iso-propylsilyl), methyl, and ethoxyethyl. In certain embodiments, an oxygen atom can be protected during a chemical reaction; e.g., the 3-hydroxyl of an opioid can react with a haloformate reagent to provide a "protected" 3-carbonate derivative. As used herein, alkylated hydroxyl groups are considered protected by the bound alkyl moiety; e.g., the 3-methoxy group of thebaine is considered, in this context, to carry a 3-hydroxyl moiety protected by the bound methyl group. In a similar manner, hydroxyl groups that react with a haloformate reagent yielding a carbonate derivative are considered protected hydroxyl groups. For example, reaction of a hydroxyl group with allyl chloroformate provides a carbonate moiety as the product, (—OC(O)O—CH$_2$—CH═CH$_2$), which can be represented herein as —OR$^{17}$, where the protecting group ("R$^{17}$") is the allyl oxycarbonyl moiety (—C(O)O—CH$_2$—CH═CH$_2$).

In connection with the heterocyclic or heteroaryl ring of formula (5) being a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected R$^{52}$ groups, the following polycyclic ring systems are non-limiting examples of a heterocyclic ring of formula (5) being a subunit of a polycyclic ring system comprising a combination of 5 total carbocyclic, heterocyclic, and aryl rings, each of which is unsubstituted:

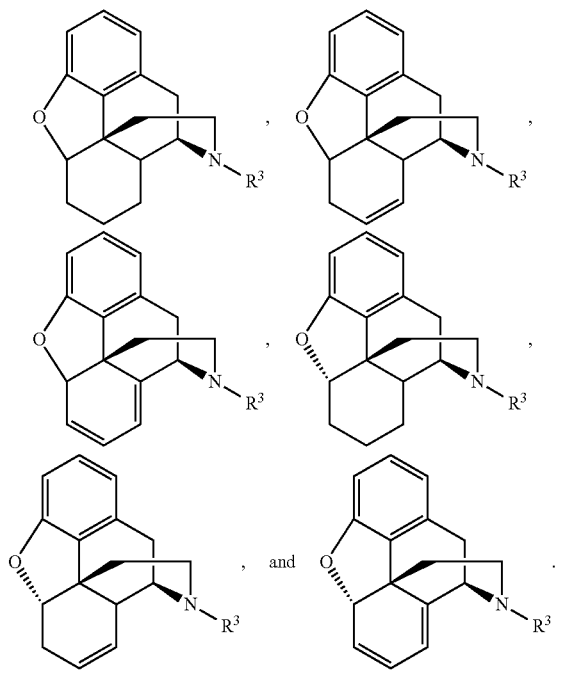

The following polycyclic ring systems are non-limiting examples of a heterocyclic ring of formula (5) being a subunit of a polycyclic ring system comprising a combination of 6 total carbocyclic, heterocyclic, and aryl rings, each of which is unsubstituted:

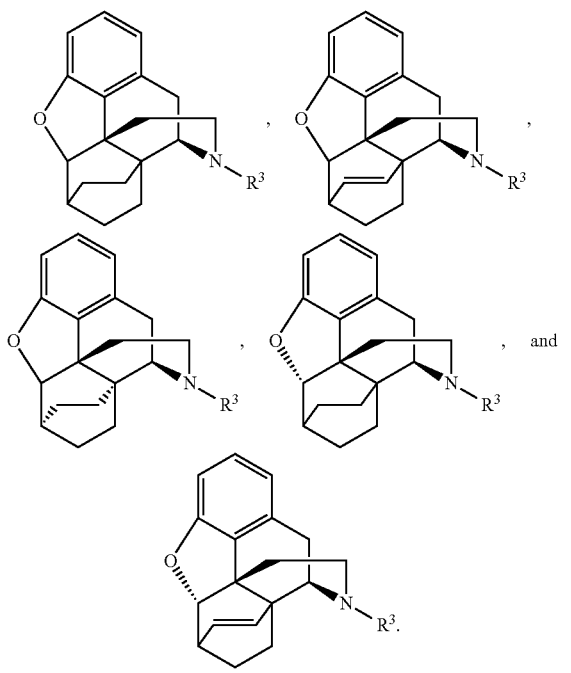

The following polycyclic ring system is a non-limiting example of a heterocyclic ring of formula (5) being a subunit of a polycyclic ring system comprising a combination of 4 total rings, one each of a carbocyclic, heterocyclic, aryl, and heteroaryl ring, each of which is unsubstituted:

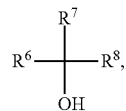

When a first group is "substituted with one or more" second groups, each of one or more of the first group's hydrogen atoms is replaced with an independently-selected second group. In one embodiment, a first group is substituted with 1, 2, or 3 independently-selected second groups. In another embodiment, a first group is substituted with 1 or 2 independently-selected second groups. In another embodiment, a first group is substituted with only one second group.

"Transition metal catalyst" as used herein means a catalyst comprising any of the transition elements capable of participating in a catalytic cycle, i.e., any of the metallic elements within Groups 3 to 12 in the Periodic Table. As used herein, the phrase "transition metal catalyst" encompasses those catalysts that comprise a transition metal of various oxidative states and that are capable of allylic decarboxylation. In certain embodiments, transition metal catalysts useful in the methods disclosed herein include complexes comprising a transition metal selected from the group consisting of Pd[0], Pd[II], Ni[0], Ni[II], Mo[0], Ru[II], Rh[I], and combinations of two or more thereof. In certain embodiments, transition metal catalysts useful in the methods disclosed herein include those comprising 1, 2, 3, or 4 phosphine moieties. Non-limiting examples of such transition metal complexes include $Pd(PPh_3)_4$, $Pd(Ph_2P(CH_2)_4PPh_2)_2$, $Ni(PPh_3)_4$, $Ni(Ph_2P(CH_2)_4PPh_2)_2$, ((pentamethylcyclopentadienyl)RuCl)$_4$, $[Pd(DBA)_2]/PPh_3$, $[Pd(OAc)_2]/PPh_3$, $[Ni(COD)_2]/PPh_3$, $NiCl_2/PPh_3$, $Ni[P(OEt)_3]_4$, $[Mo(CO)_6$-DPPE], $RhH(PPh_3)_4$-$P(n$-$Bu)_3$, and combinations of two or more thereof. In certain embodiments, the transition metal catalyst comprises $Pd(PPh_3)_4$. In certain embodiments, the transition metal catalyst consists essentially of $Pd(PPh_3)_4$. In certain embodiments, the transition metal catalyst is $Pd(PPh_3)_4$. In certain embodiments, the transition metal catalyst can be prepared in situ. For example, triphenylphosphine ($PPh_3$) can be added to a mixture containing $PdCl_2$ to prepare the catalysts $PdCl_2(PPh_3)_2$ or $Pd(PPh_3)_4$ in situ.

"Tertiary alcohol" as used herein refers to an alcohol of formula (4)

$$R^6 \overset{R^7}{\underset{OH}{-\!\!\!-\!\!\!-}} R^8,$$

in which $R^6$, $R^7$, and $R^8$ are each independently —($C_1$-$C_6$) alkyl. Illustrative tertiary alcohols therefore include tert-amyl alcohol, tert-butyl alcohol, 3-methyl-3-pentanol, 2,3-dimethyl-3-pentanol, 3-ethyl pentanol, 3-ethyl-3-pentanol, and 2-methyl-2-hexanol, and combinations of two or more thereof.

"Zinc-containing reagent" as used herein refers to any zinc-containing reagent capable to perform the reactions for which it is used in the context of present disclosure. In certain embodiments, the zinc-containing reagent can be selected from the group consisting of diethyl zinc, elementary zinc—e.g., in the form of zinc dust-, zinc-copper couple, and combinations thereof. In certain embodiments, the zinc has the oxidation number 0 (Zn[0]).

An "allyl haloformate equivalent," is a compound from which an allyl haloformate can readily be formed, e.g., a compound selected from among such compounds as formulae (6), (8), (13), (23), and (46), according to the methods disclosed herein, e.g., as depicted in Schemes 11, 12, and 29.

An "allyl scavenger" as used herein can be selected from those known in the art, e.g., from among the following illustrative examples:

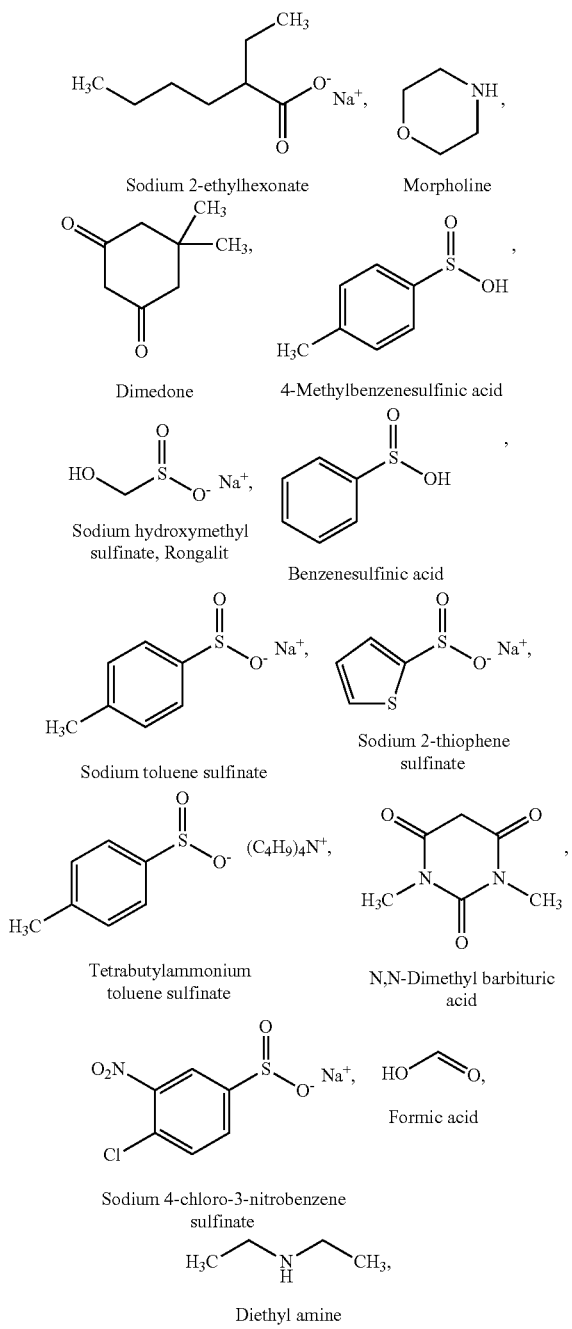

methanol, ethanol, and combinations of two or more thereof. In another embodiment illustrative example, the allyl scavenger can is be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof. In a further illustrative example, the allyl scavenger is compound (146)

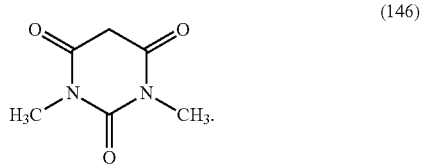

(146)

In a further illustrative example, the allyl scavenger is methanol. A "hydrogenation" is the addition of two hydrogen atoms to a double bond, thus converting it into a single bond, or the addition of two or four hydrogen atoms to a triple bond, thus converting it into a double or a single bond. It can be carried out using routine methods known in the art, for example, with a hydrogen atmosphere in the presence of a precious metal catalyst such as a carbon-supported palladium (Pd/C) or Pt/C. In other embodiments, a double bond can be subjected to transfer hydrogenation. In certain embodiments, reduction (hydrogenation) of an alkyne to an alkene is carried out in methanol with hydrogen and quinoline in the presence of 5% Lindlar catalyst. In other embodiments, the reduction of an alkyne to an alkene is carried out in the presence of $NaBH_4$, hydrogen, diethyl amine and Ni[II]acetate in aqueous methanol.

An "oxidation" is the addition of one or more (generally two) oxygen atoms to an unsaturated structural element. It can be carried out using routine methods known in the art. In certain embodiments, it is carried out using a peroxy acid, wherein the peroxy acid can be peroxybenzoic acid, performic acid, or peracetic acid, which can be prepared in situ by mixing hydrogen peroxide and excess formic acid or excess acetic acid. In a particular embodiment, it is performic acid, prepared by combining formic acid and hydrogen peroxide in a reaction mixture. In certain embodiments, the oxidation is carried out by adding osmium tetroxide and N-methyl morpholine N-oxide.

Numbering of the atoms in the structures disclosed herein is based upon the following scheme, using the chemical structure of morphine as the reference:

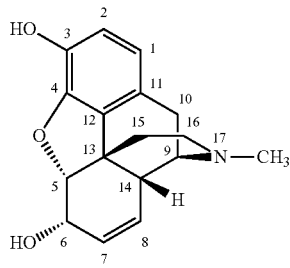

"Sub-stoichiometric amount" means an amount which is smaller than the stoichiometric amounts of a reactant(s) of the reactions described herein. For example, a sub-stoichiometric amount of the iodide salt used as catalyst in some embodiments is less than 100 mol % of the structure of formula (2). A sub-stoichiometric amount can be any numerical value within the range of from 0.001 to 99 mol % of the starting reactant (e.g., compound (2) or compound (3)) or the compounds taking place in the reaction schemes described herein. In certain embodiments, the sub-stoichiometric amount is in the range of from 20 to 70 mol %, 25 to 65 mol % or 30 to 60 mol % of the starting reactant, e.g., 30 mol % or 60 mol %.

"Catalytic amount" is a sub-stoichiometric amount which is sufficient to exert a catalytic effect on the reactions described herein. Typically, a catalytic amount can be any numerical value within the range of from 0.01 to 99 mol % of the starting reactant (e.g., compound (2) or compound (3)) or the compounds taking its place in the reaction schemes described herein. In certain embodiments, the catalytic amount is in the range of from 20 to 70 mol %, 25 to 65 mol % or 30 to 60 mol % of the starting reactant or has any numerical value within these ranges, e.g., 30 mol % or 60 mol %. An illustrative example for a catalytic compound to which these ranges apply is the iodide salt used in the context of present disclosure. In certain other embodiments, the catalytic amount is in the range of from 0.001 to 30 mol %, 0.01 to 20 mol %, 0.1 to 10 mol %, 2 to 8 mol %, or 3 to 7 mol % of the starting reagent or has any numerical value within these ranges, e.g., about 5 mol %. An illustrative example for a compound to which these ranges apply is the transition metal catalyst used in the context of present disclosure.

"Consisting essentially of" in certain embodiments of present disclosure means that the subsequently named component(s) is necessarily included but that another unlisted ingredient(s) that does not materially affect the basic and novel properties can also be present. In certain embodiments, the subsequently named component is the major component of the compound named before the term, e.g., a solvent consisting essentially of a tertiary alcohol (i.e., a compound of formula (5)) contains said tertiary alcohol (or said mixture of tertiary alcohols, see above) as major component, typically in an amount of more than 50 vol %, and other solvents (e.g., 1,2-dichloroethane, chloroform, dichloromethane, or acetonitrile) in a total amount of less than 50 vol %. In these embodiments, "consisting essentially of" means "comprising between 50 vol % and 100 vol % or any numeric value within this range of the subsequently named compound." In certain embodiments, "consisting essentially of" means "comprising from 80 to up to 100 vol % (excepting 100 vol %, as this is represented by "consisting of" in the context of present disclosure) or any numeric value within this range of the subsequently named compound, e.g., as in "a solvent comprising from 80 to up to 100 vol % tertiary alcohol".

Compounds disclosed herein can contain one or more asymmetric centers and can thus give rise to enantiomers, diastereomers, and other stereoisomeric forms. In reference to compounds of formula (1) for example, as well as all other compounds described herein that contain one or more olefinic double bonds or other centers of geometric asymmetry, unless specified otherwise, it is intended to include both E and Z geometric isomers. The method disclosed herein can be used with each of the enantiomers, diastereomers, and other stereoisomeric forms of the reagents disclosed herein to provide each of the enantiomers, diastereomers, and other stereoisomeric forms of the products disclosed herein.

In the event of doubt as to the agreement of a depicted chemical structure and a chemical name, the depicted chemical structure governs.

It will be appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.2 Methods for Making N-Allyl Compounds from Tertiary Amines

The present disclosure provides a two-step process for formation of N-allyl compounds from tertiary amines, which is depicted in Scheme 1, where $R^1$ through $R^7$ are as defined above.

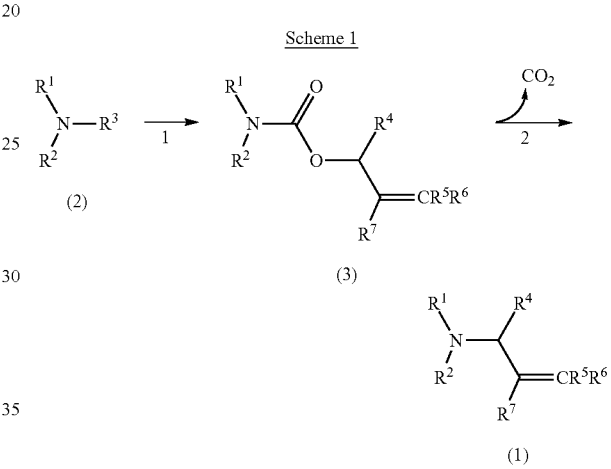

Scheme 1

The first step involves N-dealkylation of a tertiary amine of formula (2) to provide an N-allyl carbamate intermediate of formula (3) that is decarboxylated in the second step in a transition metal-catalyzed reaction to provide the N-allyl product, a compound of formula (1).

The present disclosure also provides a set of alternative reagents and methods, which can comprise one or more reactions that are useful for converting a tertiary amine of formula (2) to the N-allyl carbamate intermediate of formula (3).

For example, in one embodiment, the tertiary amine is contacted with an allyl haloformate, e.g., a compound of formula (93)

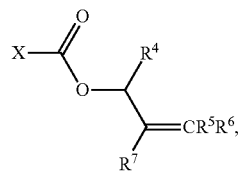

to provide the allyl carbamate product of formula (3) directly. In another embodiment, the tertiary amine is contacted with a haloformate reagent to provide a carbamate compound (e.g., a compound of formula (7) or a compound of formula (9)) that is subsequently converted to the corresponding N-allyl carbamate intermediate of formula (3).

For example, in another embodiment, the tertiary amine of formula (2) is contacted with a haloformate reagent carrying at least one leaving group (e.g., a compound of formula (6) or a compound of formula (8)), to provide a carbamate derivative (e.g., a compound of formula (7) or a compound of formula (9)). In certain embodiments, the haloformate reagent comprises one leaving group. In certain embodiments, the haloformate reagent comprises two leaving groups. The carbamate derivative is converted to the corresponding N-allyl carbamate and then to the N-allyl product in sequential transition metal-catalyzed reactions.

The two steps of Scheme 1 are illustrated by the reaction schemes below, in which oxymorphone and oxycodone are (1) demethylated to the corresponding carbamate derivatives and (2) decarboxylated to the corresponding N-allyl compounds.

4.2.1 Dealkylation of Tertiary Amines and Formation of Carbamate Intermediates: Conversion of Oxymorphone to N-Allyl Noroxomorphone and Oxycodone to N-Allyl Noroxycodone As noted above, the process disclosed herein for conversion of tertiary amines to N-allyl derivatives thereof can be depicted as comprising two steps. In the first step, which is depicted in Scheme 2, a tertiary amine is demethylated by contacting the tertiary amine with an allyl haloformate (in this case allyl chloroformate, compound (102)) in a solvent in the presence of a base to provide the intermediate N-allyl carbamate.

Scheme 2

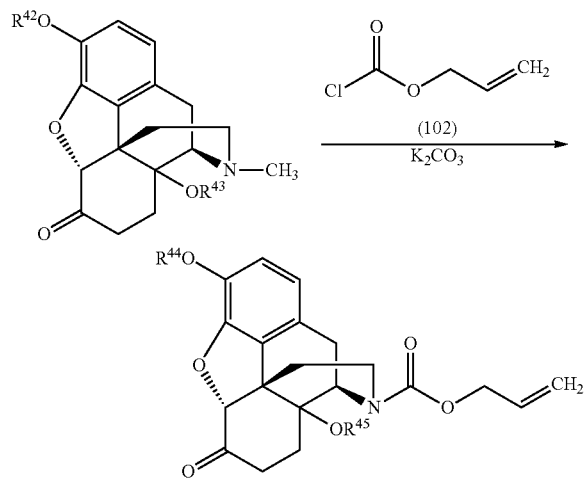

As previously discussed, e.g., in connection with $R^{14'}$ and $R^{16'}$, the definitions of $R^{44}$ and $R^{45}$ will depend on the functional groups present at $R^{42}$ and $R^{43}$, respectively. It will be appreciated that when $R^{42}$ is H, then —$OR^{44}$ can include allyl carbonate

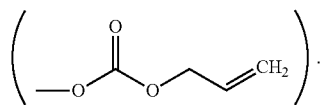

Likewise, when $R^{43}$ is H, then —$OR^{45}$ can be an allyl carbonate. The extent of allyl carbonate formation at the positions comprising $R^{42}$ and $R^{43}$ is dependent on the relative rate of reaction at these sites compared to the rate of reaction of the tertiary amine. Allyl carbonates can be converted back to —OH groups using methods described below. It will be further appreciated that when —$OR^{42}$ is selected to be a particular moiety that is not an —OH group, then —$OR^{44}$ is also that particular —$OR^{42}$ moiety. Likewise, it will be appreciated that when —$OR^{43}$ is selected to be a particular moiety that is not an —OH group, then —$OR^{45}$ is also that particular —$OR^{43}$ moiety.

Table 1 summarizes data from five reactions according to Scheme 2. These include N-demethylation of: 3,14-bis-acetoxy-oxymorphone (Reaction 1 in Table 1), oxycodone (Reaction 2), oxymorphone (Reaction 3), and 3-allyl oxymorphone (Reaction 4). Each of Reactions 1-4 was carried out with excess (at least 6 equivalents excess) allyl chloroformate (compound (102)) in the presence of potassium carbonate (1.5 equivalents) in 1,2-dichloroethane at reflux temperature for 48 hours. In the first four reactions, which were carried out at the reflux temperature of 1,2-dichloroethane (approximately 84° C.), 50-78% of the starting opioid was consumed.

In Reaction 5, oxymorphone was demethylated with excess allyl chloroformate (compound (102)) in the presence of $K_2CO_3$ using tert-amyl alcohol as the solvent. Reaction 5 was carried out according to the method described in Example 3 (described below), in which additional amounts of allyl chloroformate are added throughout the duration of the reaction. In this instance, more than 97% of oxymorphone was consumed.

TABLE 1

| Reaction | $R^{42}$ | $R^{43}$ | Solvent | % Starting Opioid Consumed |
|---|---|---|---|---|
| 1 | Acetyl | Acetyl | $ClCH_2CH_2Cl$ | 60 |
| 2 | $CH_3$ | H | $ClCH_2CH_2Cl$ | 78 |
| 3 | H | H | $ClCH_2CH_2Cl$ | 62 |
| 4 | Allyl | H | $ClCH_2CH_2Cl$ | 50 |
| 5 | H | H | $H_3C{-}C(CH_3)(CH_3){-}OH$ | >97 |

4.2.2 Transition Metal-Catalyzed Decarboxylation of N-Methyl Opioids to Provide N-Allyl Products In the second step of Scheme 2, the intermediate N-allyl carbamate is decarboxylated in a transition metal-catalyzed reaction to provide the corresponding N-allyl derivative. As illustrated in Scheme 3, the carbamate products of Table 1 were contacted with a transition metal catalyst comprising palladium[0] in the reaction depicted in Scheme 3.

Scheme 3

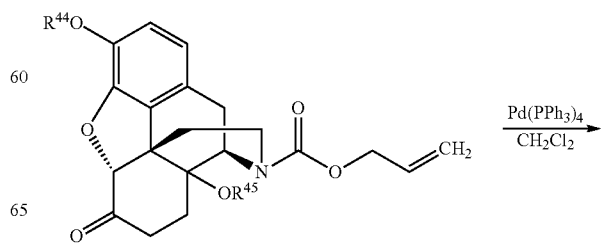

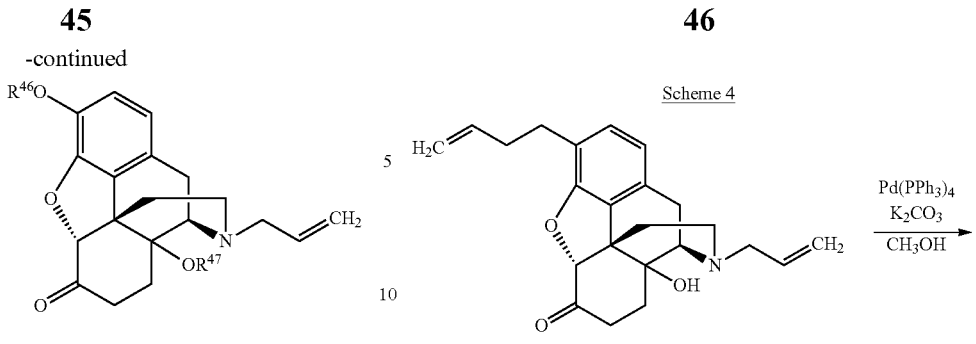

As previously discussed, e.g., in connection with $R^{14'}$ and $R^{16'}$, the definitions of $R^{46}$ and $R^{47}$ will depend on the functional groups present at $R^{44}$ and $R^{45}$, respectively. In Scheme 3, $R^{46}$ and $R^{47}$ can be —H, —CH$_3$, acetyl, or allyl.

Table 2 provides the results obtained upon decarboxylation of the oxymorphone and oxycodone functionalized carbamate starting compounds identified in Table 2. As indicated in Table 2, in certain embodiments reactions with 3,14-bis-acetoxy compounds provided a complex mixture of products (Reaction 1 of Table 2 below). In contrast, decarboxylation of substrates in which the 3- and 14-hydroxyl groups were not protected by acetylation, and therefore were present as free hydroxyl groups or as carbonate derivatives thereof, provided improved yields (Reactions 2 and 3 of Table 2). In these embodiments, the decarboxylation reactions were carried out in dichloromethane at a temperature of about 25° C. in the presence of a catalytic amount (0.05 equivalents) of tetrakis(triphenylphosphine)palladium[0]. In certain embodiments, $R^{47}$ is —H.

TABLE 2

| Reaction | $R^{44}$ | $R^{45}$ | Conversion |
|---|---|---|---|
| 1 | Acetyl | Acetyl | About 5%, many products |
| 2 | CH$_3$ | H/Allyl carbonate (a) | >99% |
| 3 | Allyl carbonate (b) | H/Allyl carbonate (a) | >99% |

(a) Indicates a mixture of 14-hydroxyl and 14-allyl carbonate species.

(b) Indicates that the 3-position of the compound carried an allyl carbonate moiety. As noted below, as in Reaction 3 of Table 2, the 3-carbonate moiety is converted to the 3-allyl ether in the transition metal-catalyzed decarboxylation reactions depicted in Scheme 3 (i.e., $R^{46}$ is allyl).

It has also been found that 14-functionalized allyl carbonates selectively undergo allylic decarboxylation, yielding the desired 14-hydroxyl products. Therefore, in Reactions 2 and 3 of Table 2, the product of the transition metal-catalyzed reaction depicted in Scheme 3 is one in which $R^{47}$ is —H.

It has also been found that allylic decarboxylation was successful with 3-allyl functionalized substrates, e.g., where $R^{44}$ of Scheme 3 is an allyl carbonate moiety (Reaction 3 of Table 2). In this instance, the 3-allylcarbonate group was converted to a 3-allyl ether derivative rather than to a free hydroxyl (i.e., $R^{46}$ is allyl). The 3-allyl ether can be converted to the corresponding 3-OH in a transition metal-catalyzed reaction in the presence of a base and an allyl scavenger (e.g., methanol), as depicted in Scheme 4.

Scheme 4

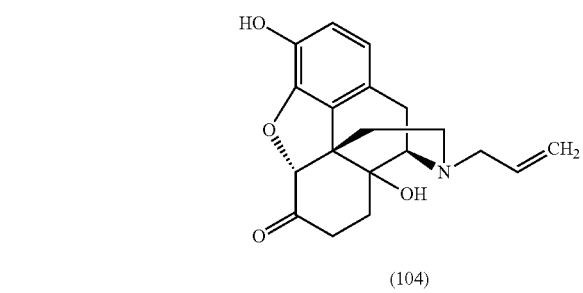

(103)

(104)

In other embodiments, e.g., as depicted in Scheme 10, formation of the 3-allyl ether can be avoided by incorporating a base-treatment step after synthesis of the N-allyl carbamate derivative comprising a 3-carbonate moiety but before the transition metal-catalyzed decarboxylation reaction depicted in Scheme 3 above and Scheme 5 below.

4.3 Processes for Conversion of Oxymorphone to Naloxone and for Conversion of Oripavine to Naloxone 4.3.1 Process for the Conversion of Oxymorphone to Naloxone As indicated in Section 4.2.1, a tertiary amine, e.g., oxymorphone, can be contacted with allyl chloroformate to provide the 17-carbamate derivative, e.g., the 17-carbamate of of oxymorphone, 17-allyloxycarbonyl-noroxomorphone (compound (105)) (e.g., see Example 3 below). Compound (105) in turn can be decarboxylated to provide compound (104) (naloxone) in a transition metal-catalyzed reaction, as depicted in Scheme 5.

Scheme 5

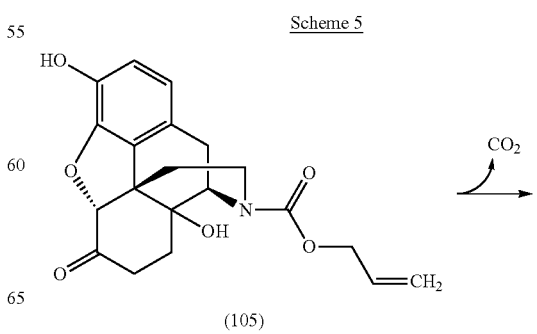

(105)

-continued

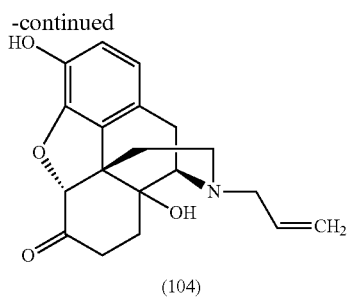

In another illustrative embodiment, the decarboxylation reaction depicted in Scheme 5 can be incorporated in an overall process, depicted in Scheme 6, for conversion of oripavine to naloxone. In fact, the synthetic approach of Scheme 6 can be carried out as a "one pot" process without chromatographic isolation of the intermediate products.

4.3.2 Process for Synthesis of Naloxone from Oripavine

The transition metal-catalyzed decarboxylation of 17-allyloxycarbonyl noroxymorphone can be exploited to provide the overall process for conversion of the natural product oripavine (compound (106)) to the semi-synthetic derivative thereof, naloxone (compound (104)) according the reaction scheme depicted below. In these reactions, the 3-hydroxyl of oripavine and the 3- and 14-hydroxyls of compound (107) and compound (108) (oxymorphone) need not be protected in one or more separate steps. As disclosed below, the phenolic 3-OH is expected to react with the allyl haloformate reagent employed in the demethylation reaction to yield the 3-allyl carbonate. Although the 14-OH is typically less reactive than the 3-OH group, a 14-allyl carbonate group can also be formed by reaction with the haloformate reagent.

Step 1 of Scheme 6 depicts the oxidation of oripavine (compound (106)) to 14-hydroxymorphinone (compound (107)) which can be carried out by contacting oripavine with a peroxyacid such as peracetic acid, performic acid, or m-chloroperbenzoic acid. The peroxy acid can be formed in situ, for example by addition of hydrogen peroxide to acetic acid or to formic acid.

In Step 2 of Scheme 6, the oxidized compound (compound (107)) is hydrogenated to oxymorphone (compound (108)). Hydrogenation can be carried out, for example, with a hydrogen atmosphere in the presence of a precious metal catalyst such as a carbon-supported palladium (Pd/C) or Pt/C (see, e.g., Krassnig et al. (1996) *Arch. Pharm. Med. Chem.* 329:325-326; U.S. Pat. No. 5,112,975 to Wallace; U.S. Pat. No. 4,472,253 to Schwartz; and U.S. Pat. Nos. 1,485,673 and 1,468,805 to Freund et al., each of which is hereby incorporated by reference in its entirety). In other embodiments, the 7,8-double bond of compound (107) can be subjected to transfer hydrogenation to provide compound (108) (see, e.g., WO 2005/097801 A1; U.S. Pat. No. 6,177,567 B1; WO 2006/094672 A1; and Fahrenholtz (1972) *J. Org. Chem.* 37(13):2204-2207, each of which is hereby incorporated by reference in its entirety).

In Step 3 of Scheme 6, oxymorphone can be contacted with an allyl haloformate, e.g., allyl chloroformate

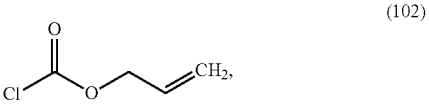

(compound (102)), in a solvent in the presence of a base to provide the corresponding allyl carbamate, a compound of formula (70)

Scheme 6

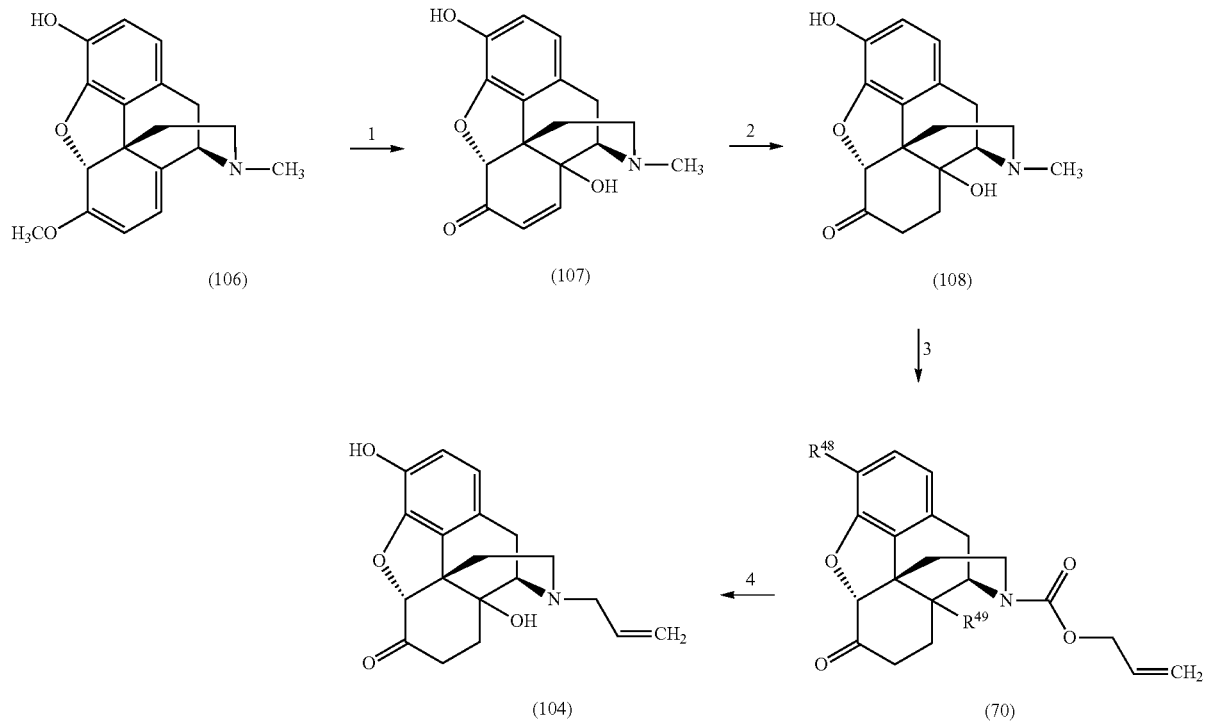

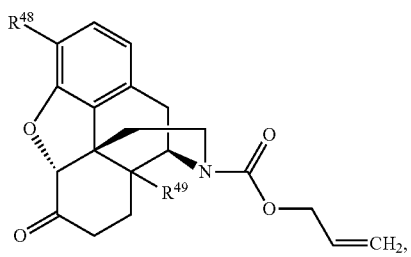

in which R⁴⁸ is —OC(O)OCH₂CH═CH₂ and R⁴⁹ is —OH or —OC(O)OCH₂CH═CH₂.

In one embodiment, the. Step 3 starting material, e.g., oxymorphone (compound (106)), is taken up in a solvent in the presence of a base. The solvent can be any suitable solvent in which the reaction can proceed. In certain embodiments, the solvent is selected from the group consisting of ether solvents, acetonitrile, benzene, DMF, DMSO, N,N-dimethylpropionamide, DMPU, DMI, DME, DMAC, NMP, ethyl acetate, ethyl formate, ethyl-methyl ketone, iso-butylmethylketone, formamide, hexamethylphosphoramide, methyl acetate, N-methylacetamide, N-methylformamide, nitrobenzene, nitromethane, propionitrile, sulfolane, tetramethylurea, THF, toluene, CHCl₃, CH₂Cl₂, 1,2-dichloroethane, THF, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments of Step 3, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment, the solvent comprises tert-amyl alcohol. In another specific embodiment, the solvent consists essentially of tert-amyl alcohol. In another specific embodiment, the solvent is tert-amyl alcohol.

In certain embodiments of Step 3, the base is selected from the group consisting of borate salts (such as, for example, NaBO₃), di- and tri-basic phosphate salts (such as, for example, Na₂HPO₄, Na₃PO₄, combinations thereof, and the like), bicarbonate salts (such as, for example, NaHCO₃, KHCO₃, combinations thereof, and the like), hydroxide salts (such as, for example, NaOH, KOH, combinations thereof, and the like), carbonate salts (such as, for example, Na₂CO₃, K₂CO₃, Cs₂CO₃, combinations of two or more thereof, and the like), organic proton acceptors (such as, for example, pyridine, triethylamine, di-iso-propylethylamine, N-methylmorpholine, N,N-dimethylaminopyridine, combinations of two or more thereof, and the like), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl) piperazine-1-ethanesulfonic acid (HEPES), 2-(4-morpholinyl) ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), any salt thereof and/or combinations of two or more thereof, and the like. In certain embodiments, the base is selected from the group consisting of NaHCO₃, KHCO₃, LiHCO₃, KHCO₃, LiHCO₃, Na₂CO₃, K₂CO₃, Cs₂CO₃, NaOH, KOH, Na₂HPO₄Na₃PO₄, K₂HPO₄, K₃PO₄, and combinations of two or more thereof. In specific embodiments, the base is selected from the group consisting of triethylamine, di-iso-propylethylamine, Na₂CO₃, NaHCO₃, KHCO₃, K₂CO₃, Cs₂CO₃, and combinations of two or more thereof. In a specific embodiment, the base is NaHCO₃.

In one embodiment, Step 3 of Scheme 6 can be carried out in the presence of an iodide salt, which can be selected from the group consisting of NaI, KI, LiI, CsI, RuI, MgI₂, CaI₂, NH₄I, tetrabutylammonium iodide, and combinations of two or more thereof. In certain embodiments, the iodide salt is NaI. In certain embodiments, the iodide salt is present in a sub-stoichiometric amount. In certain embodiments, the iodide salt is present in a catalytic amount.

In one embodiment, the allyl haloformate (compound (48)), here allyl chloroformate (compound (102)), is added to the mixture and the reaction run at a temperature within the range of from about 15° C. to about 85° C., or from about 20° C. to about 75° C., or from about 25° C. to about 75° C., or from about 35° C. to about 70° C., or from about 45° C. to about 65° C., or from about 50° C. to about 60° C. for an initial period of time within the range of from about 0.5 hours to about 2 hours, or from about 0.5 hours to about 1.5 hours, or from about 0.75 hours to about 1.25 hours. In certain embodiments, the reaction is run at a temperature of about 55° C. In certain embodiments, the reaction is run for an initial period of about one hour. An aliquot of the mixture is analyzed to determine the extent of the reaction. If the reaction has not proceeded to the extent desired, the mixture is heated, thereby removing water (e.g., as an azeotrope with tert-amyl alcohol) and allyl chloroformate, as well as any ethanol, allyl chloride, or allyl alcohol that might be present in the reaction. After cooling, the solvent is replenished as necessary, additional allyl haloformate reagent is added, and the reaction continued. This cycle of testing, distillation, solvent replenishment, and allyl haloformate addition can be repeated one or more times. In certain embodiments, particularly where the base treatment step (Step 4A of Scheme 10 below) is omitted, the allyl carbamate product (e.g., see the compound of formula (70)) R⁴⁸ moiety can be an allyloxycarbonyl moiety and, in certain embodiments, R⁴⁹ will be a hydroxyl moiety (e.g., see compound (109)) while, in other embodiments, R⁴⁸ and R⁴⁹ will both be allyloxycarbonyl moieties (e.g., see compound (110)). Where R⁴⁸ and R⁴⁹ are each hydroxyl moieties, the compound of formula (70) is 17-allyloxycarbonyl noroxymorphone, compound (105).

In certain embodiments, e.g., those in which R⁴⁸ and/or R⁴⁹ are allyloxycarbonyl groups, Step 4 can involve multiple sub-steps that result in conversion of the 17-allyloxycarbonyl intermediate, carrying a 3-allyloxycarbonyl moiety and/or 14-allyloxycarbonyl moiety, to the end product, naloxone, as depicted in Scheme 6. Step 4 of Scheme 6, therefore, reflects conversion of the allyl carbamate group (17-allyloxycarbonyl group) of compound (70) to an N-allyl moiety via the transition metal-catalyzed reaction depicted in Schemes 1 and 3, and where both R⁴⁸ and R⁴⁹ either are hydroxyl groups or are converted to hydroxyl groups, the product of Step 4 of Scheme 6 is compound (104), i.e., naloxone.

More specifically, the product of Step 3 of Scheme 6 (i.e., compounds of formula (70)) can include both of the following compounds.

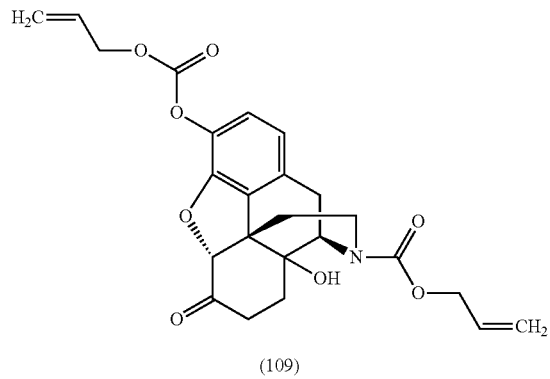

(109)

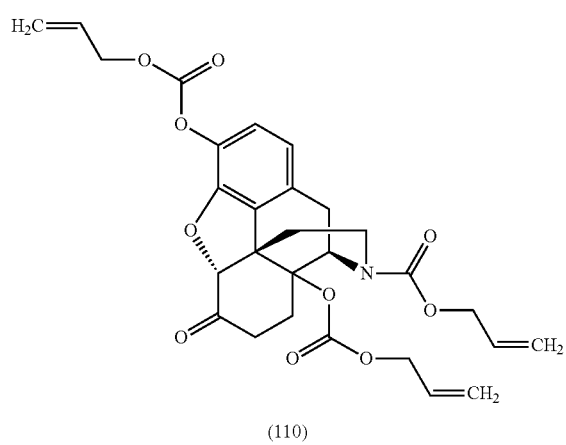

(110)

That is, the product of Step 3 of Scheme 6 is expected to carry an allyloxycarbonyl group at both the 3-position and the 17-position, and can also carry an allyloxycarbonyl moiety at the 14-position as well. In certain embodiments, the product of Step 3 of Scheme 6 carries a free hydroxyl at the 14-position and, in particular embodiments, the product of Step 3 of Scheme 6 is almost entirely compound (109).

In certain embodiments, particularly at early time points (see, e.g., Example 3), an initial product of Step 3 of Scheme 6, can be compound (145):

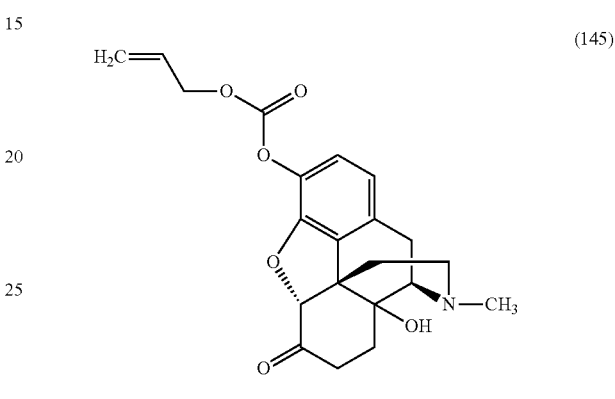

(145)

and therefore, the products of Step 3 of Scheme 6 can include compound (145), compound (109), and compound (110).

In one embodiment, the product(s) of Step 3 of Scheme 6 are contacted with a transition metal catalyst, whereby the 14-allyloxycarbonyl group is converted to a hydroxyl, the N-allylcarbamate group is converted to an N-allyl moiety, and the 3-allyloxycarbonyl is converted to a 3-allyl ether moiety, as depicted in Scheme 7.

Scheme 7

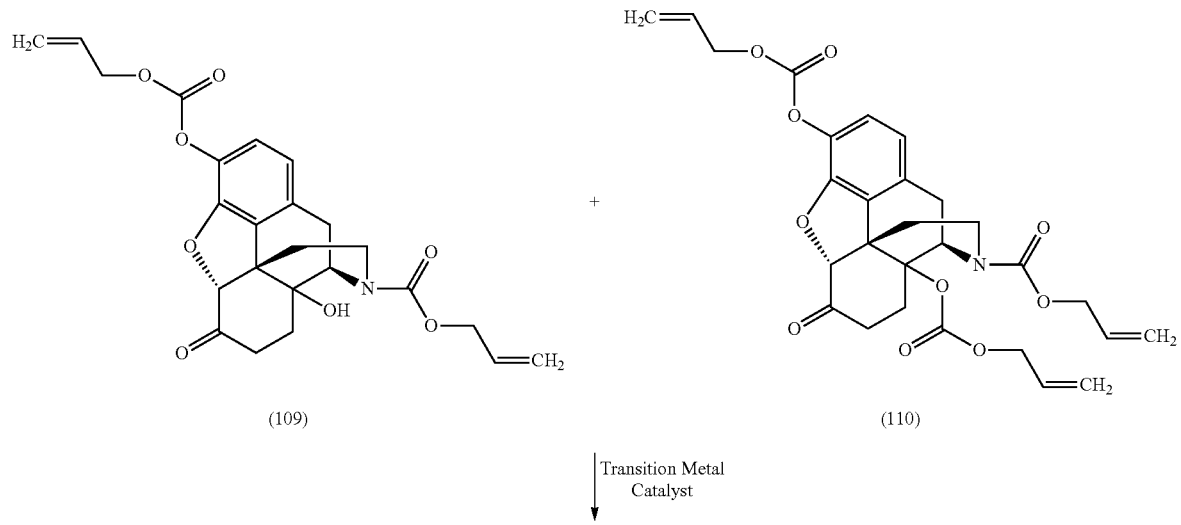

(109)         (110)

Transition Metal
Catalyst

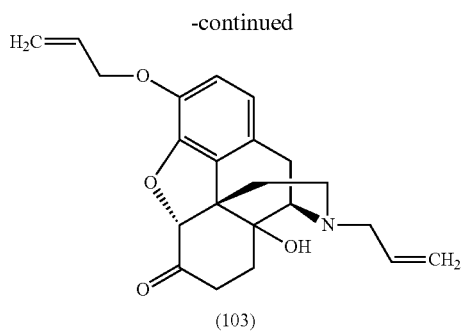

(103)

In certain embodiments, the mixture of 3,17-diallyloxycarbonyl-noroxymorphone (compound (109)) and 3,14,17-triallyloxycarbonyl-noroxymorphone (compound (110)) is dissolved in a solvent (e.g., chloroform or methylene chloride) and a suitable transition metal catalyst, e.g., tetrakis(triphenylphosphine)palladium[0], is added. The decarboxylation reaction is carried out for a suitable time and at an appropriate temperature for the reaction to proceed to completion. In one embodiment, the reaction is carried out for four hours at a temperature of about 20° C.

The reaction mixture is filtered and the filtrate concentrated. The resulting oil is taken up in a solvent, e.g., ethyl acetate, extracted with acid, e.g., 0.5N HCl, and the aqueous layer washed with an organic solvent, which in one embodiment is ethyl acetate. The aqueous layer is basified, e.g., to pH 9.1 using 50% aqueous NaOH, and extracted with an organic solvent which, in one embodiment, is chloroform. The recovered organic layers are combined, dried, filtered, and concentrated to provide an oil comprising the product, 3-allyl-naloxone (compound (103)), as depicted in Scheme 7 above.

In one embodiment, the 3-allylether naloxone product (compound (103)) is oxygen de-allylated to naloxone, by contact with a suitable transition metal catalyst, e.g., tetrakis(triphenylphosphine)palladium[0], in the presence of a base and an allyl scavenger. In certain embodiments, the base is $K_2CO_3$.

In one embodiment, the allyl scavenger can be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof. In another embodiment, the allyl scavenger is methanol.

In a particular embodiment, the base is $K_2CO_3$ and the allyl scavenger is methanol, i.e., the reaction is that depicted in Scheme 8.

Scheme 8

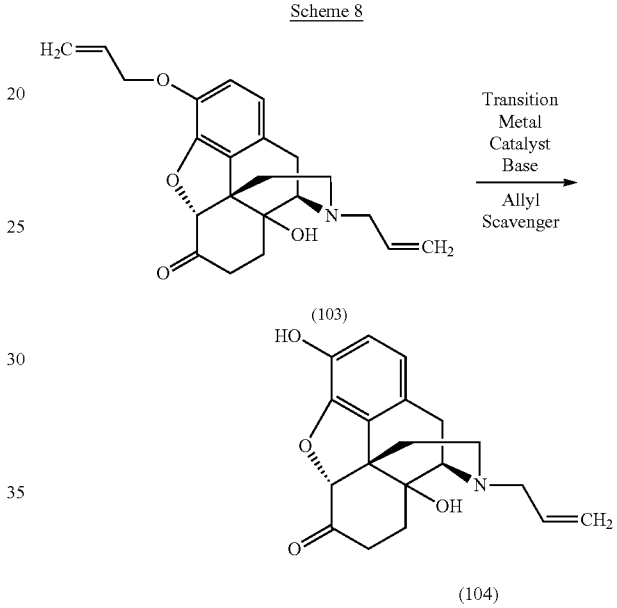

Thus, in one embodiment, 3-allylether-naloxone is taken up in a suitable solvent and contacted with a base and a transition metal catalyst in the presence of an allyl scavenger. The base can be selected from among those described above as useful in Step 3 of Scheme 6, and the transition metal catalyst is a catalyst that comprises a transition metal selected from the group consisting of Pd[0], Pd[II], Ni[0], Ni[II], Mo[0], Ru[II], Rh[I], and combinations of two or more thereof. In certain illustrative embodiments, the transition metal catalyst is a complex selected from the group consisting of $Pd(PPh_3)_4$, $Pd(Ph_2P(CH_2)_4PPh_2)_2$, $Ni(PPh_3)_4$, $Ni(Ph_2P(CH_2)_4PPh_2)_2$, ((Pentamethylcyclopentadienyl)$RuCl)_4$, $[Pd(DBA)_2]/PPh_3$, $[Pd(OAc)_2]/PPh_3$, $[Ni(COD)_2]/PPh_3$, $NiCl_2/PPh_3$, $Ni[P(OEt)_3]_4$, $[Mo(CO)_6$-DPPE], RhH$(PPh_3)_4$-P(n-Bu)$_3$, and combinations of two or more thereof. In another embodiment, the transition metal catalyst comprises 1, 2, 3, or 4 phosphine moieties. In another embodiment, the transition metal catalyst is tetrakis(triphenylphosphine)palladium[0]. In one embodiment, the base is potassium carbonate and the allyl scavenger is methanol. The de-allylation reaction is carried out for a suitable time and at an appropriate temperature for the reaction to proceed to completion; in one embodiment, the reaction is carried out for four hours at a temperature of about 20° C., i.e., a temperature typically within the range of from about 15° C. to about 25° C., or from about 17° C. to about 23° C., or from about 19° C. to about 21° C.

The reaction mixture is filtered and the filtrate concentrated. The resulting oil is taken up in a solvent, e.g., ethyl acetate, extracted with acid, e.g., 0.5N HCl, and the aqueous layer washed with an organic solvent, which in one embodiment is ethyl acetate. The aqueous layer is basified, e.g., to pH 9 using 50% aqueous NaOH, and extracted with an organic solvent which, in one embodiment, is chloroform. The recovered organic layers are combined, dried, filtered, and concentrated to provide an oil comprising the product, naloxone.

In certain embodiments, the reactions of Schemes 7 and 8 can be combined by including a base and an allyl scavenger in the reaction mixture used for decarboxylative de-allylation, thereby providing the reaction scheme depicted in Scheme 9.

3,17-diallyloxycarbonyl and 3,14,17-triallyloxycarbonyl intermediates, and combinations thereof, in a single step.

4.3.3 Additional Process for Making Naloxone from Oripavine

In another approach, the 3-allylcarbonate and 14-allylcarbonate groups can be cleaved before the transition metal-catalyzed decarboxylation of the 17-carbamate moiety. In this embodiment, once Step 3 of Scheme 6 is deemed complete, base and water are added and the reaction mixture is heated at a temperature and for a time sufficient to hydrolyze the 3-allyoxycarbonyl and 14-allyloxycarbonyl moieties. After cooling, the reaction mixture is first acidified to a pH of about pH 1 to about pH 2, and the layers allowed to separate. The organic layer is retained, washed with 10% sodium hydrogen sulfate, and concentrated to provide 17-al-

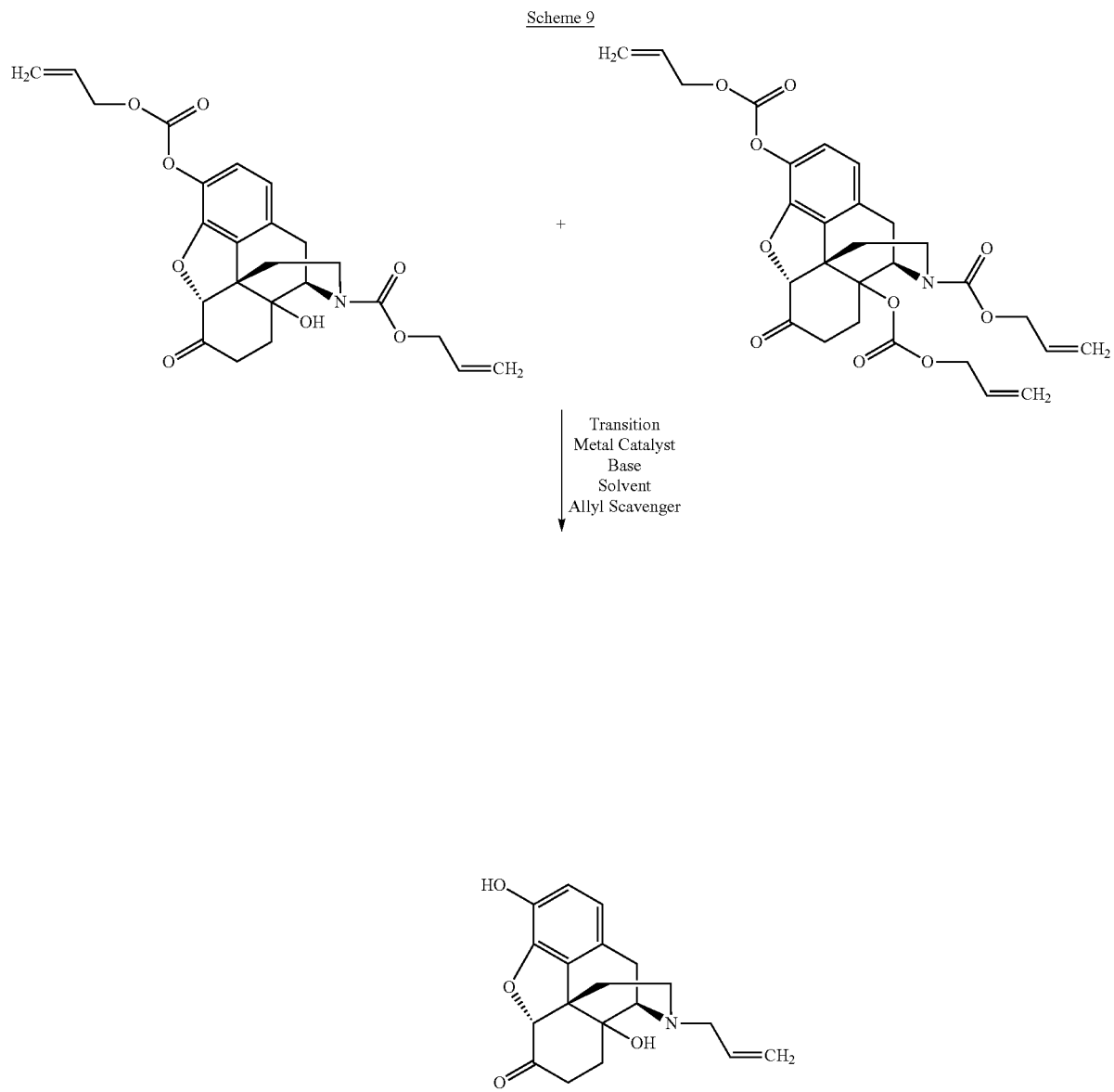

Scheme 9

In certain embodiments, the transition metal catalyst is Pd(PPh$_3$)$_4$, the base is K$_2$CO$_3$, the solvent is chloroform, and the allyl scavenger is methanol. The reaction depicted in Scheme 9 therefore permits formation of naloxone from the lyloxycarbonyl-noroxymorphone. This hydrolysis step of can be incorporated into an overall process, e.g., for the production of naloxone from oripavine, as depicted in Scheme 10.

Scheme 10

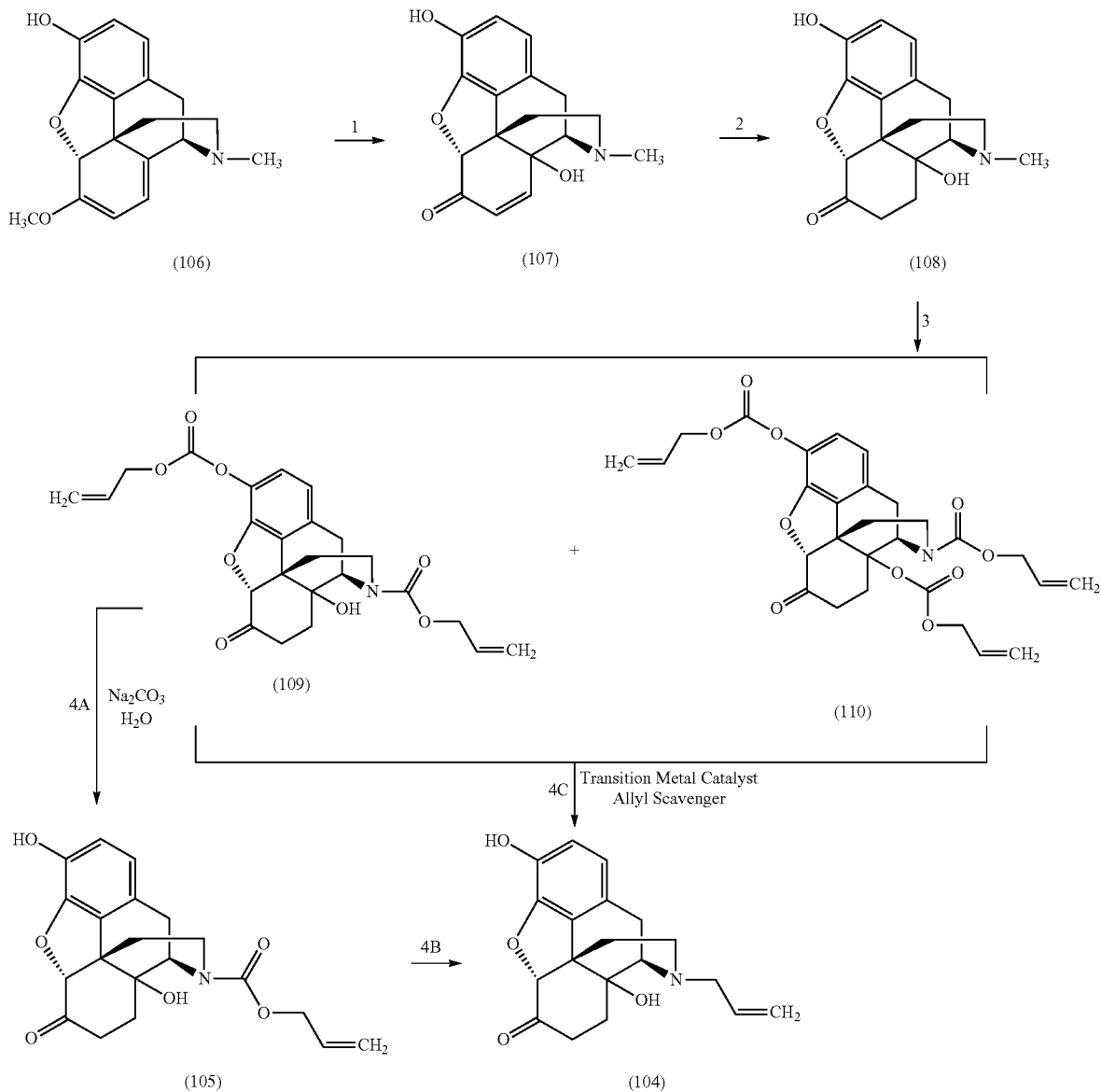

The base-mediated hydrolysis step described above is depicted as Step 4A in Scheme 10 and the transition metal-catalyzed decarboxylation step (Step 4B of Scheme 10) corresponds to the reaction depicted in Schemes 3 and 5, above.

In certain embodiments, the compounds of formula (109) and formula (110) are converted to compound (104) in Step 4C mediated by a transition metal catalyst in the presence of an allyl scavenger (e.g., as depicted in Scheme 9).

In one embodiment of the process of Scheme 10, oripavine (compound (106)) is oxidized (Step 1) with a peroxy acid to 14-hydroxy morphinone (compound (107)). In certain embodiments, the peroxy acid is peroxybenzoic acid, performic acid, or peracetic acid, which can be prepared in situ by mixing hydrogen peroxide and excess formic acid or excess acetic acid. In a particular embodiment, oripavine is oxidized in performic acid, prepared by combining oripavine, formic acid, and hydrogen peroxide into a reaction mixture. The reaction mixture is warmed to a suitable temperature within the range of from about 25° C. to about 80° C., or from about 30° C. to about 70° C., or from about 35° C. to about 65° C., or from about 40° C. to about 60° C., or from about 45° C. to about 55° C., and maintained at that temperature for about 0.5 hours to about 3.5 hours, or from about 1 hour to about 3 hours, or from about 1.5 hours to about 2.5 hours, until the starting material is consumed. In particular embodiments, the oxidation is carried out at about 48° C. for about 2 hours.

The crude product, 14-hydroxy-morphinone (compound (107)) of the oxidation reaction (Step 1) is then taken directly on to the second step without purification. Thus, once oxidation is complete, the crude 14-hydroxy-morphinone (compound (107)) is hydrogenated (Step 2) in the presence of a palladium catalyst under a hydrogen atmosphere at 40-45° C. (Step 2) to provide oxymorphone (compound (108)). The hydrogen can be provided at a pressure of from about 15-70 psig, or from about 20-65 psig, or from about 25-60 psig, or from about 30-55 psig, or from about 35-50 psig. In one embodiment, hydrogen is provided at a pressure of 40-45 psig. The hydrogenation is carried out at a temperature within the range of from about 25° C. to about 80° C., or from about 30° C. to about 70° C., or from about 35° C. to about 65° C., or from about 40° C. to about 60° C. In certain embodiments, the hydrogenation is carried out at a temperature within the range of from about 40° C. to about 45° C. The reaction mixture is then cooled to a temperature within the range of from about 2° C. to about 10° C. and filtered to remove the catalyst. The pH of the filtrate is adjusted and the reaction mixture stirred to allow the resultant crude oxymorphone free base to form a precipitate that is filtered, washed and dried.

Crude oxymorphone, which contains residual water and, in some instances, can also contain residual ethanol, is dissolved in tert-amyl alcohol and the solution dried to remove water. This oxymorphone solution is then treated with excess allyl chloroformate (compound (102)) and sodium bicarbonate at 70-85° C. (Step 3). Once the reaction is complete (i.e., conversion of oxymorphone to the 3-allylcarbonate-N-allylcarbamate noroxymorphone (compound (109)), in which none, some, or all of the 14-OH can also be converted to a 14-allylcarbonate group (i.e., compound (110)), water and sodium carbonate are added and, in Step 4A, the mixture is heated to 80-85° C. for at least 15 hours to destroy excess allyl chloroformate and to hydrolyze the 3-carbonate moiety as well as any 14-carbonate groups that might be present, providing the 17-allylcarbamate derivative of noroxymorphone (compound (105)). The product, noroxymorphone-17-allylcarbamate, can be extracted into a suitable organic solvent which can be filtered, washed, and dried using normal work-up procedures. If desired, the product can be recovered by evaporation of that solvent.

In certain embodiments, the reaction of oxymorphone with allyl chloroformate can be carried out in the presence of an iodide salt, which can be selected from the group consisting of NaI, KI, LiI, CsI, RuI, $MgI_2$, $CaI_2$, $NH_4I$, tetrabutylammonium iodide, and combinations of two or more thereof. In certain embodiments, the iodide salt is NaI. In certain embodiments, the iodide salt is present in a sub-stoichiometric amount. In certain embodiments, the iodide salt is present in a catalytic amount.

In the decarboxylation reaction, Step 4B, N-allyl carbamate noroxymorphone (compound (105)) is taken up in an appropriate solvent, e.g., chloroform, and contacted with a transition metal catalyst, e.g., tetrakis(triphenylphosphine) palladium[0]. The resulting mixture is allowed to stir at a temperature of about 20° C. before being filtered, e.g., through a pad of CELITE. The desired product, naloxone (compound (104)), is then separated from the reaction by normal work-up procedures.

4.3.4 Further Processes for Conversion Of Oxymorphone to Noroxymorphone-17-allylcarbamate and to Naloxone In another embodiment, oxymorphone is converted to noroxymorphone-17-allylcarbamate in two steps, as depicted in Scheme 11.

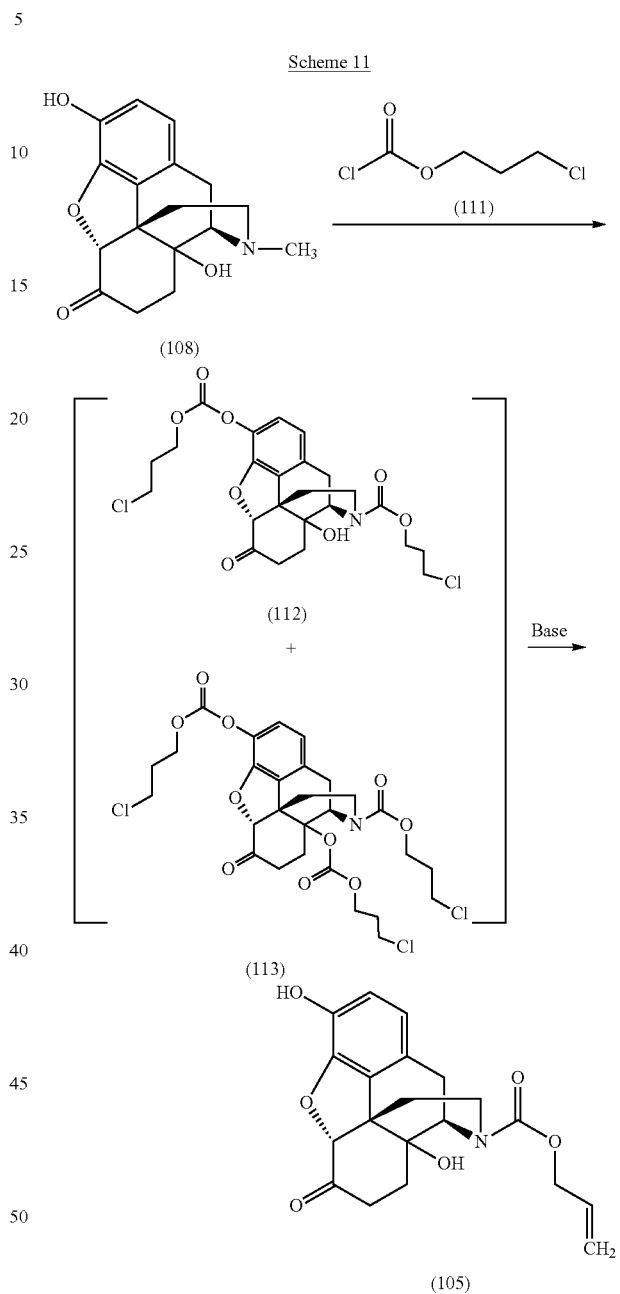

As provided above, oxymorphone (compound (108)) starting material can be prepared from oripavine (compound (106)) according to the methods depicted in Schemes 6 and 10 above, and the product noroxymorphone-17-allylcarbamate (compound (105)) can be converted to naloxone (compound (104)) by the transition metal-catalyzed decarboxylation reactions depicted in Schemes 3, 5, 6, 7, 9, and 10 above.

In a further embodiment, oxymorphone can be converted to naloxone as depicted in Scheme 12.

Scheme 12
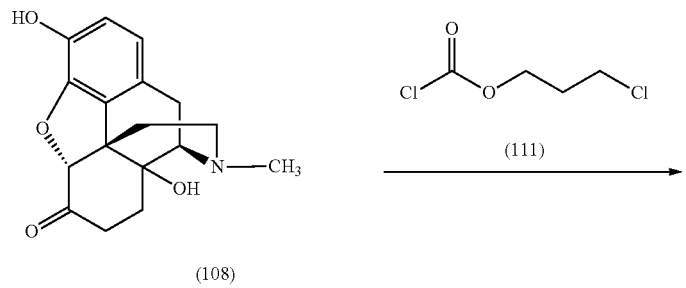
(108) (111)
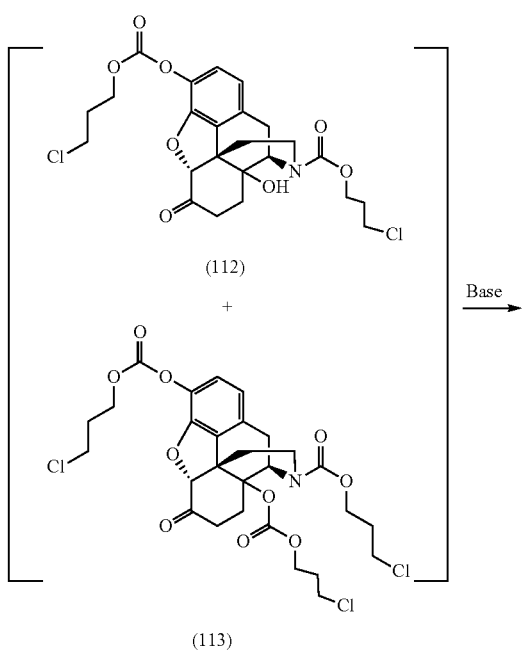
(112)
+
(113)
Base →
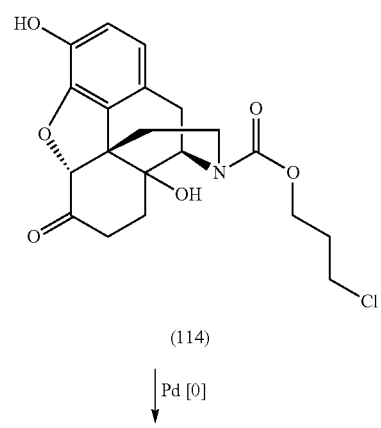
(114)
↓ Pd [0]

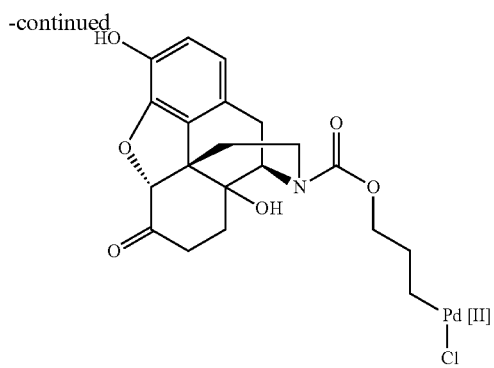

(115)

β—Hydride elimination → HCl

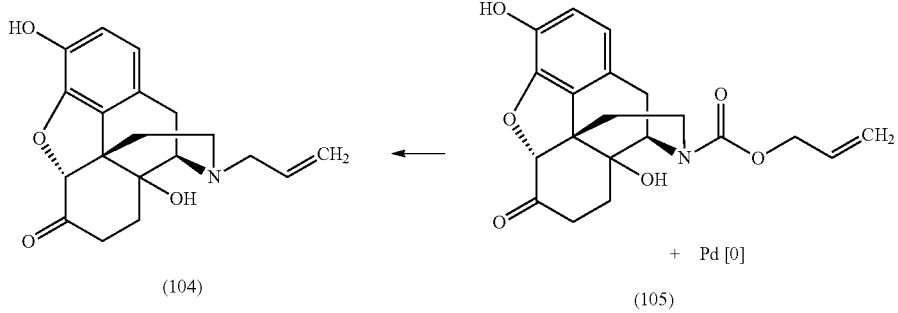

(104)     (105)     + Pd [0]

Although the transition metal catalyst is depicted in Scheme 12 as "Pd[0]," as noted above other transition metal catalysts, including but not limited to those transition metal catalysts comprising Pd[II], Ni[0], Ni[II], Mo[0], Ru[II], and Rh[I], can be used in those reactions. In another embodiment, the transition metal catalyst comprises 1, 2, 3, or 4 phosphine moieties. In another embodiment, the transition metal catalyst is tetrakis(triphenylphosphine)palladium[0].

4.4 Preparation of N-Allyl Compounds from Secondary Amines

In certain embodiments, the present disclosure provides transition metal-catalyzed reactions for the preparation of N-allyl compounds from secondary amines, including, for example, methods for the preparation of naloxone from noroxymorphone as depicted in Scheme 13.

Scheme 13

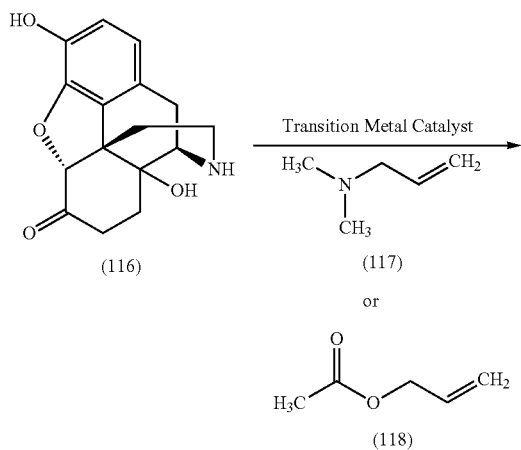

(116)     (117)

or (118)

-continued

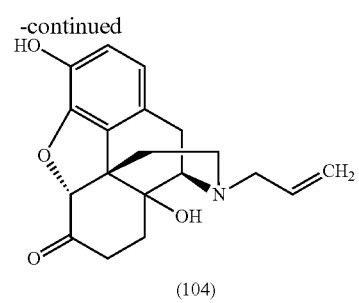

(104)

In other embodiments, the allylation reaction depicted in Scheme 13 can be carried out using 1-cyclopropenyl-N,N-dimethylmethanamine or cyclopropenylmethyl acetate to provide the corresponding cyclopropenyl-comprising derivative of noroxymorphone that can be hydrogenated to provide naltrexone.

In another embodiment, the allylation reaction depicted in Scheme 13 can be carried out using 1-cyclobutenyl-N,N-dimethylmethanamine or cyclobutenylmethyl acetate to provide the corresponding cyclobutenyl-comprising derivative of noroxymorphone that again can be hydrogenated to provide the corresponding cyclobutyl-comprising derivative of noroxymorphone.

In still other embodiments, the allylation reaction depicted in Scheme 13 can be carried out using an allyl haloformate, e.g., allyl chloroformate, to provide an allyl carbamate intermediate, or another reagent providing a carbamate intermediate that can be converted to an allyl carbamate intermediate, and then converting the allyl carbamate to the allyl amine in a transition metal-catalyzed reaction.

4.5 Synthesis of Noroxymorphone from Oxymorphone and from Naloxone

4.5.1 Synthesis of Noroxymorphone from Naloxone

In another embodiment, the present disclosure provides a method for conversion of oxymorphone and naloxone to noroxymorphone as depicted in Scheme 14.

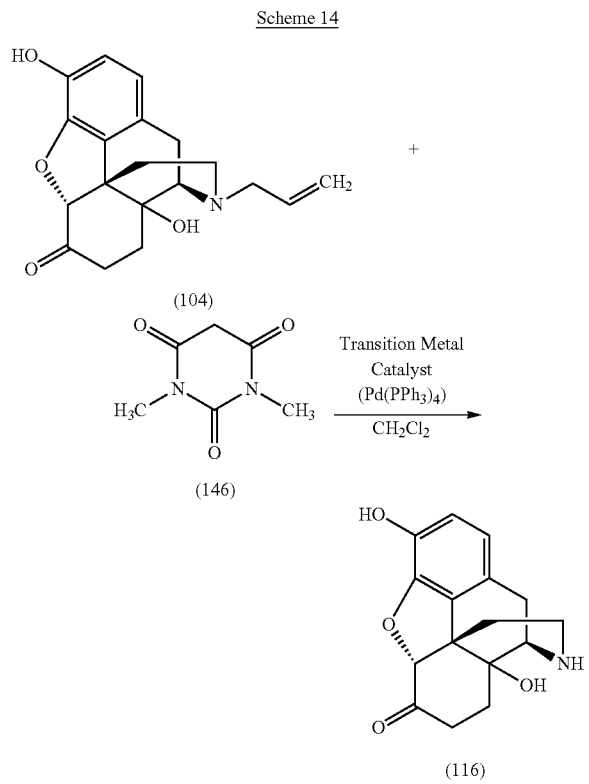

Naloxone (compound (104)) is contacted with an allyl scavenger, e.g., N,N-dimethyl barbituric acid (compound (146)), and a transition metal catalyst, e.g., tetrakis(triphenylphosphine)palladium[0], in dichloromethane at a temperature of about 20° C. Naloxone as a suspension in dichloromethane is added, and the resulting mixture stirred overnight at a temperature within the range of from about 10° C. to about 70° C., or from about 20° C. to about 60° C., or from about 30° C. to about 60° C. The mixture is cooled and the solids collected by filtration, washed with dichloromethane, and then washed with water. The washed solids are dissolved in aqueous acid (e.g., 10:1 water:concentrated sulfuric acid) at a temperature within the range of from about 10° C. to about 70° C., or from about 20° C. to about 60° C., or from about 30° C. to about 60° C., and the solution washed with dichloromethane before being basified to a pH within the range of from about pH 8 to about pH 10, e.g., using 28% ammonium hydroxide. The solids are collected by filtration and dried to provide the desired product, noroxymorphone (see, e.g., Example 7).

In other aspects of this embodiment, for example, oxymorphone is first converted to naloxone by the methods depicted in Schemes 10 and 12 above, and then to noroxymorphone by the method depicted in Scheme 14, thereby providing an overall process for conversion of oxymorphone to noroxymorphone.

4.5.2 Synthesis of Noroxymorphone from Oxymorphone

In a further embodiment, naloxone is prepared from oxymorphone in three steps. In the first step (not depicted in Scheme 15), oxymorphone is demethylated to provide a first 17-oxycarbonyl derivative (i.e., a compound of formula (71)), e.g., according to the method depicted in Scheme 10 above but using a haloformate reagent of the formula X—C(O)OR$^{50}$, where X is selected from —Cl, —Br, and —I, and in which R$^{50}$ is not an allyl moiety. For example, in one embodiment, R$^{50}$ is phenyl and, in another embodiment, R$^{50}$ is benzyl. In the second step, the 17-oxycarbonyl derivative (compound (71)) is contacted with an alkoxide derivative of an allyl alcohol (i.e., a compound of formula (61)) to provide a 17-allyloxycarobnyl derivative (e.g., compound (105)) which, in a third step, is decarboxylated in a transition metal-catalyzed reaction, e.g., that of Schemes 3 and 5, to provide naloxone (compound (104)). This embodiment is depicted in Scheme 15.

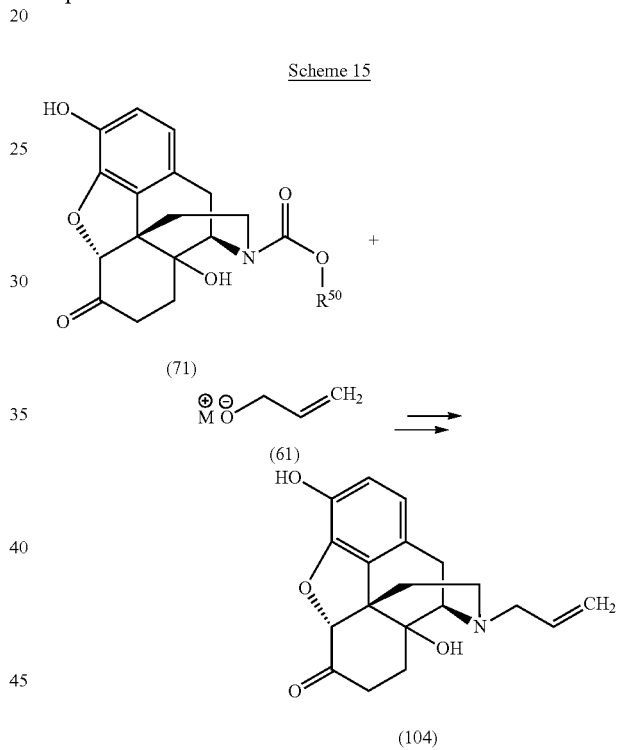

The methods of the present disclosure are versatile and, as but one example, they are readily adapted to provide a process for the synthesis of naltrexone from oripavine, according to the process depicted in Scheme 10 above but using, e.g.,

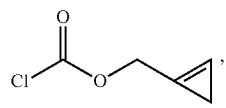

compound (119) as the allyl haloformate reagent for N-demethylation of oxymorphone, and including a final hydrogenation step to convert the cyclopropene moiety to a cyclopropane group. An illustrative example of such a process is provided in Scheme 16.

Scheme 16
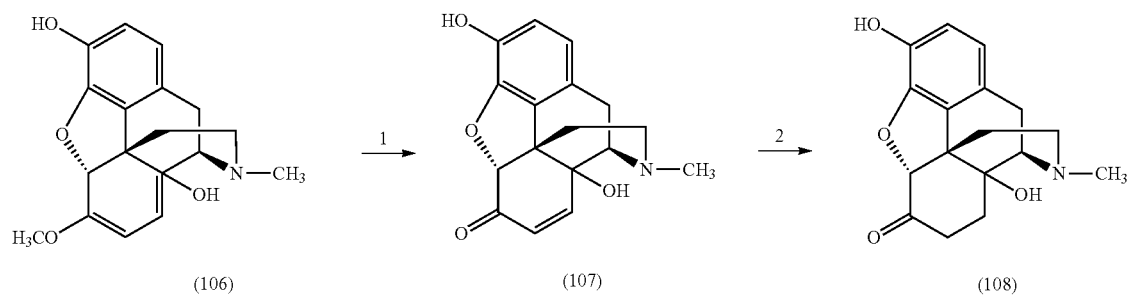
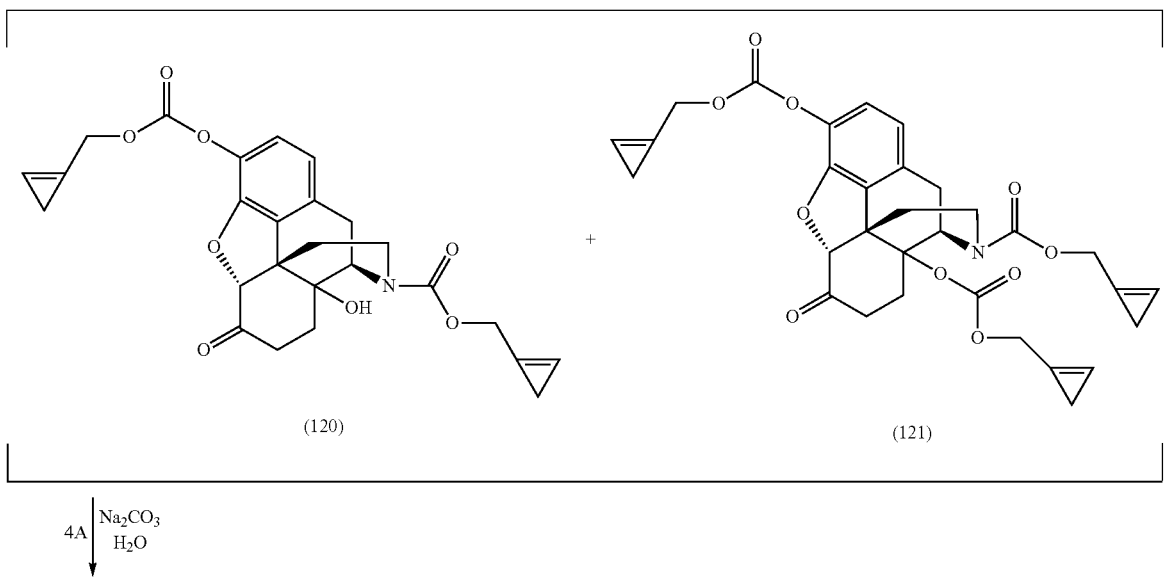
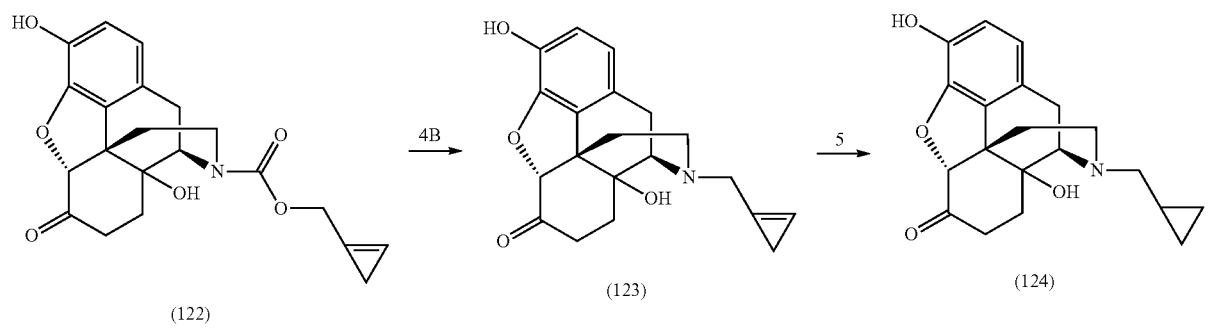

In certain embodiments, Step 2 of Scheme 16 can be omitted since the 7,8-double bond can be hydrogenated step in Step 5 (see, e.g., Scheme 34 below).

4.6 Transition Metal-catalyzed Reactions for the Synthesis of Cabergoline

In another embodiment, the methods disclosed herein are also useful in processes for the synthesis of the potent dopamine receptor agonist cabergoline (compound (125)),

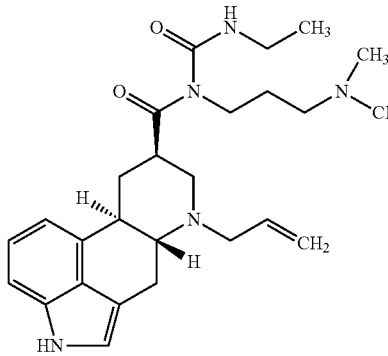

(125)

which involve the conversion of the tertiary amine of either lysergol (compound (126)) or elymoclavine (compound (128)) to include the N-allyl group of cabergoline, using the reagents and methods disclosed herein.

Scheme 17

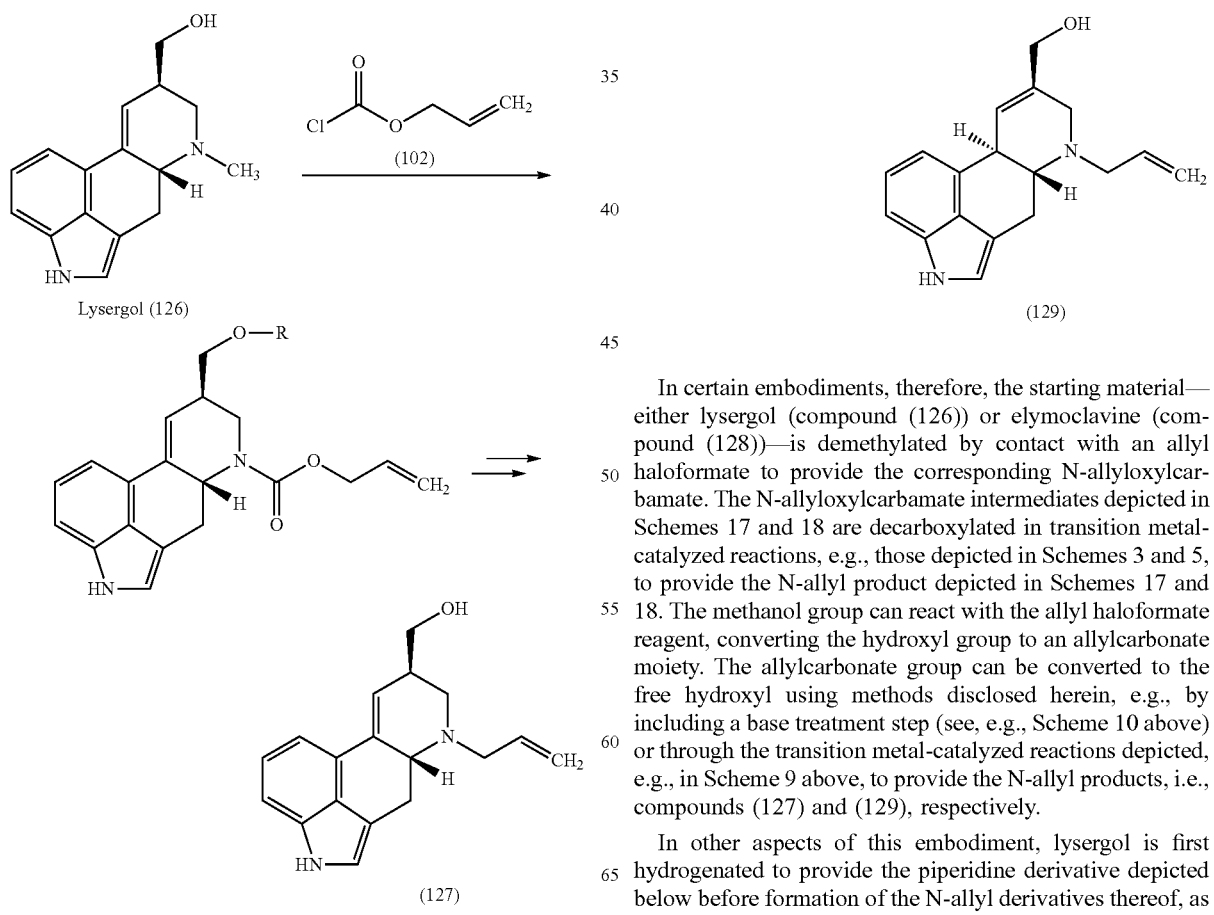

Scheme 18

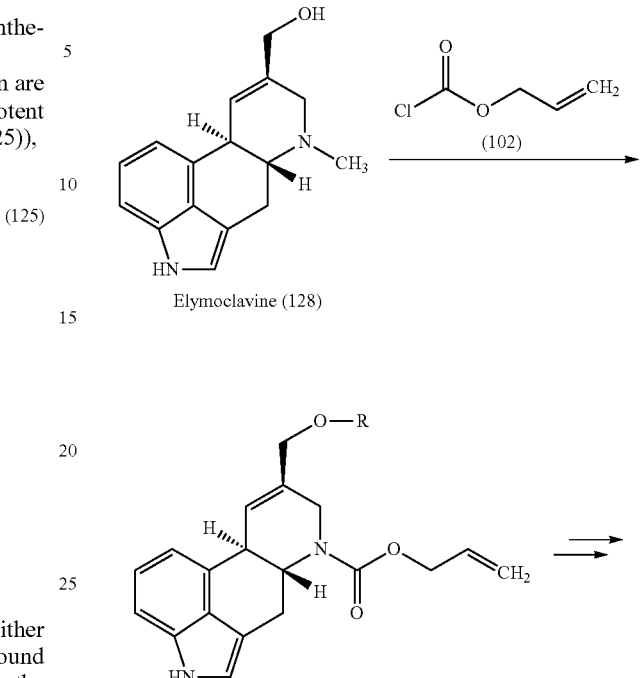

In certain embodiments, therefore, the starting material—either lysergol (compound (126)) or elymoclavine (compound (128))—is demethylated by contact with an allyl haloformate to provide the corresponding N-allyloxylcarbamate. The N-allyloxylcarbamate intermediates depicted in Schemes 17 and 18 are decarboxylated in transition metal-catalyzed reactions, e.g., those depicted in Schemes 3 and 5, to provide the N-allyl product depicted in Schemes 17 and 18. The methanol group can react with the allyl haloformate reagent, converting the hydroxyl group to an allylcarbonate moiety. The allylcarbonate group can be converted to the free hydroxyl using methods disclosed herein, e.g., by including a base treatment step (see, e.g., Scheme 10 above) or through the transition metal-catalyzed reactions depicted, e.g., in Scheme 9 above, to provide the N-allyl products, i.e., compounds (127) and (129), respectively.

In other aspects of this embodiment, lysergol is first hydrogenated to provide the piperidine derivative depicted below before formation of the N-allyl derivatives thereof, as depicted Scheme 19.

Scheme 19
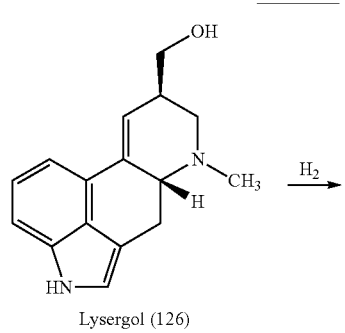
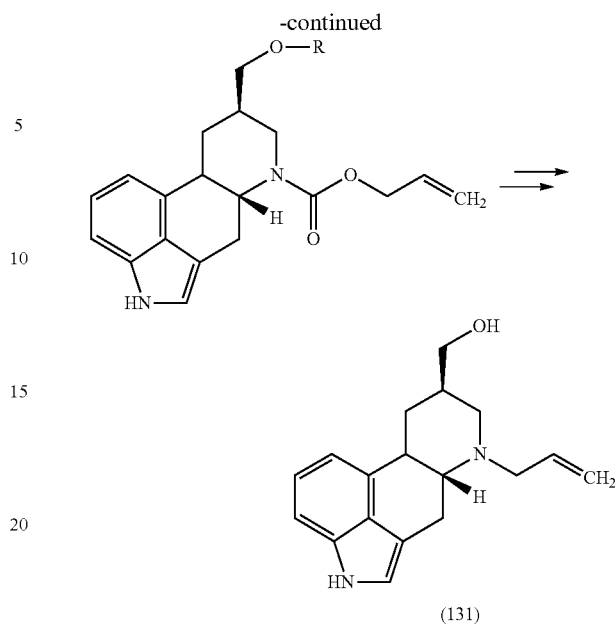
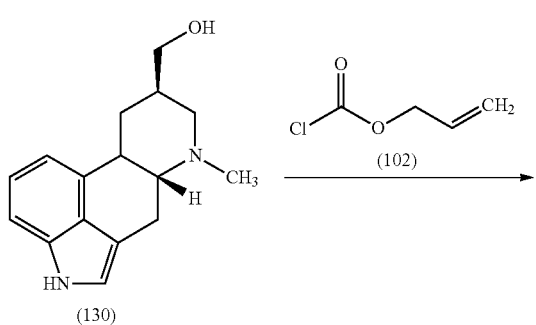
Other synthetic routes useful in a process for production of cybergoline from lysergol that employ the transition metal-catalyzed decarboxylation reactions disclosed herein are depicted in Scheme 20.
Scheme 20
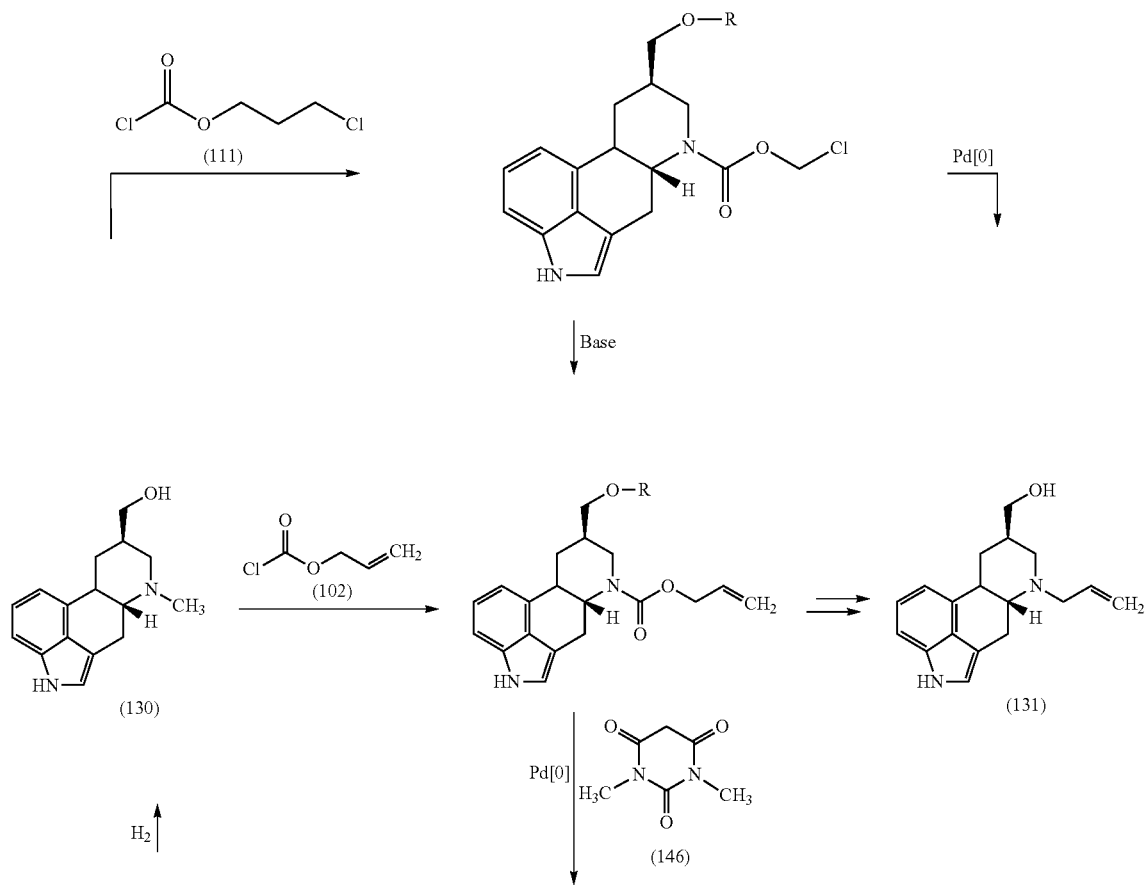

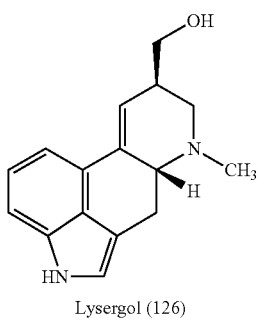

Lysergol (126)

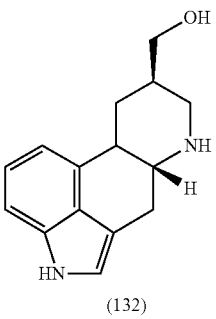

(132)

Elymoclavine could be substituted for lysergol in the methods depicted in Scheme 20 for preparation of cabergoline. In other aspects of this embodiment, elymoclavine is first hydrogenated to provide the piperidine derivative depicted below before formation of the N-allyl derivatives thereof, as depicted Scheme 21.

Scheme 21

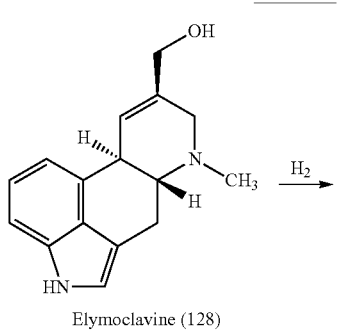

Elymoclavine (128)

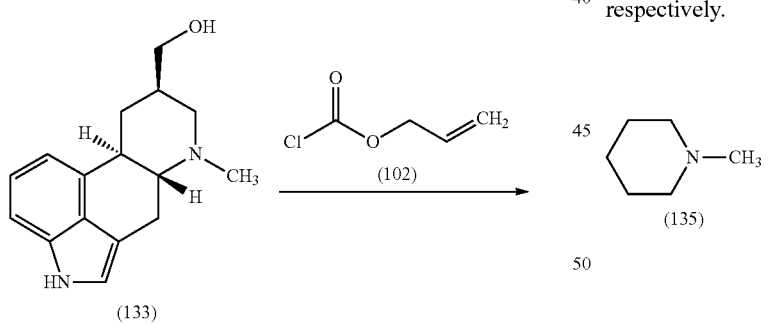

(133)

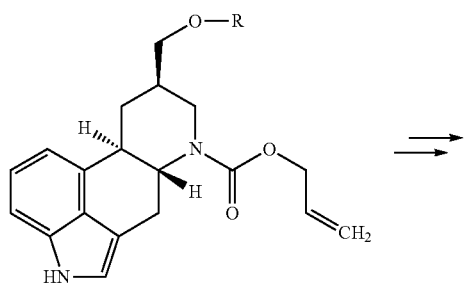

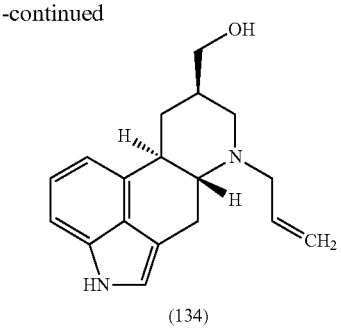

(134)

Conditions for hydrogenation of lysergol or elymoclavine and the additional reactions for conversion of the N-allyl derivative disclosed above to the final product can be found in U.S. Patent Application Publication No. US 2008/0275240 A1 and U.S. Pat. No. 7,217,822 B2, each of which is hereby incorporated by reference in its entirety.

In certain other, illustrative embodiments, the methods disclosed are used for converting 1-methyl-piperidine and di-iso-propylethylamine to the corresponding N-allyl derivatives, as depicted in Scheme 22 and Scheme 23, respectively.

Scheme 22

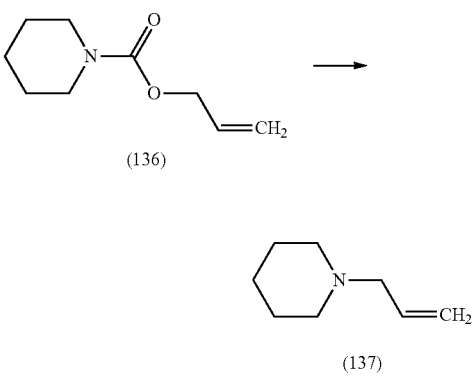

-continued
Scheme 23

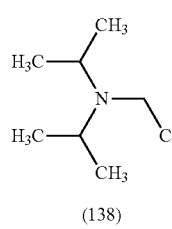

(138)

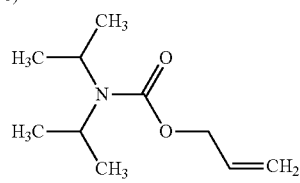

(139)

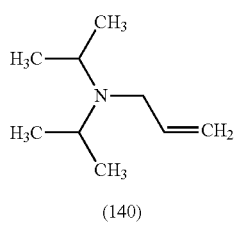

(140)

In certain other, illustrative embodiments, the methods disclosed are used for converting the following tertiary amines to the corresponding secondary amines or "nor" derivatives: atropine, caffeine, (+) eschscholtzidine, galanthamine, and nicotine, according to Schemes 24 through 28.

Scheme 24: Atropine

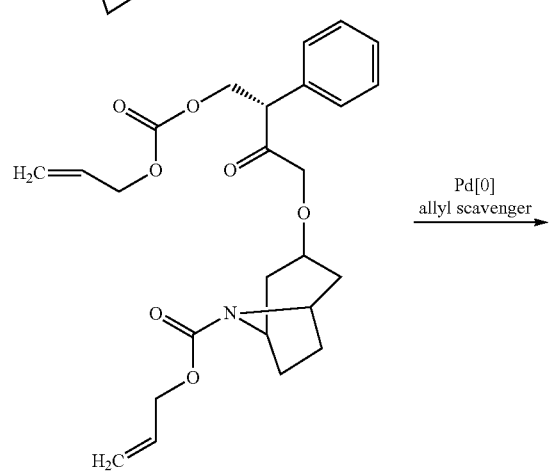

-continued

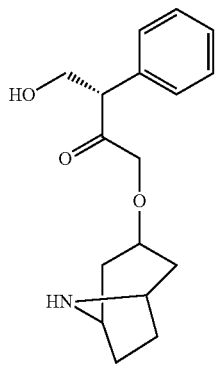

Scheme 25: Caffeine

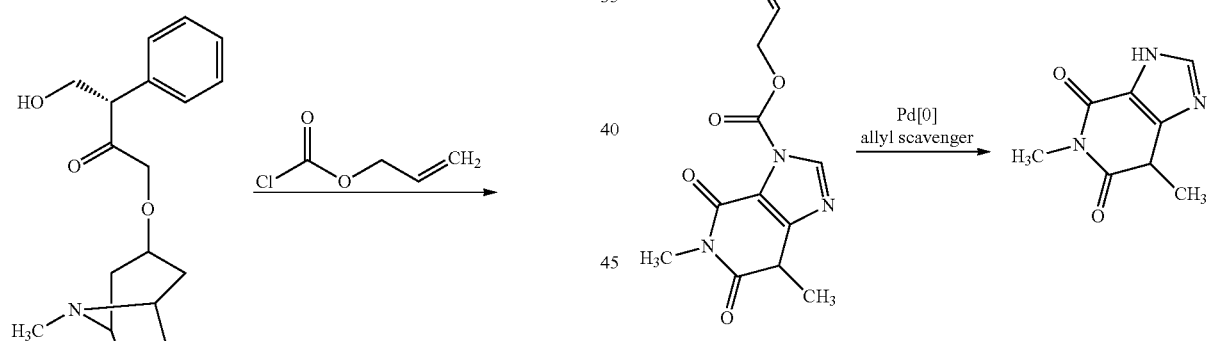

Scheme 26: (+)-Eschscholtzidine

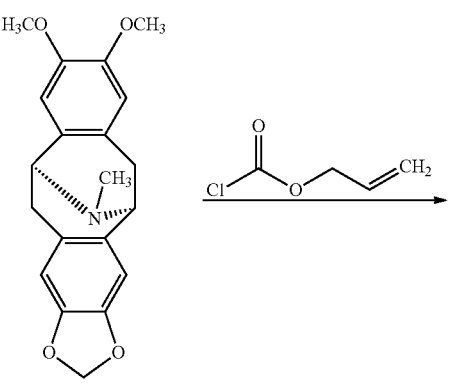

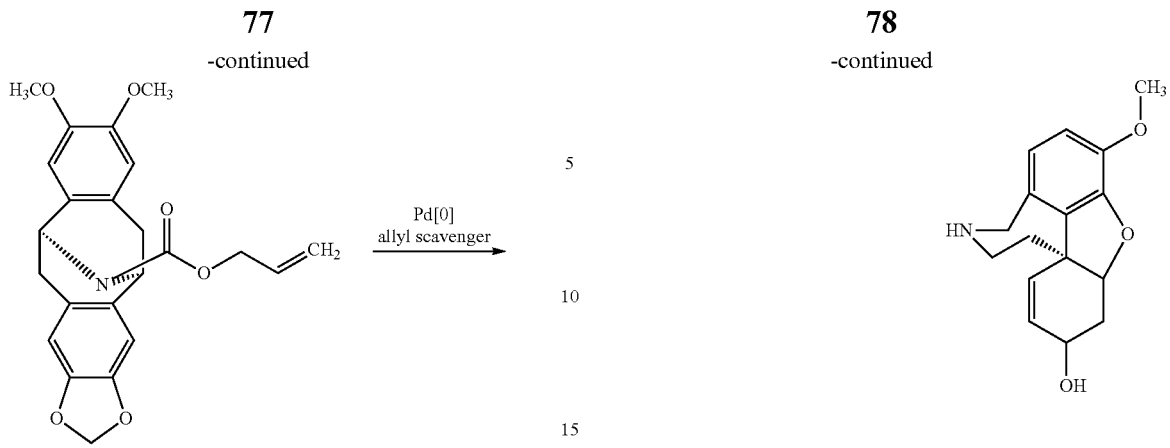

Scheme 27: Galanthamine

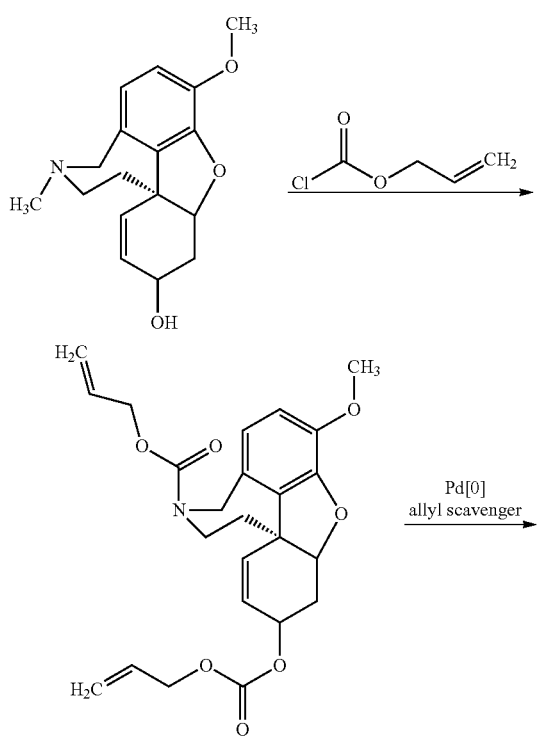

Scheme 28: Nicotine

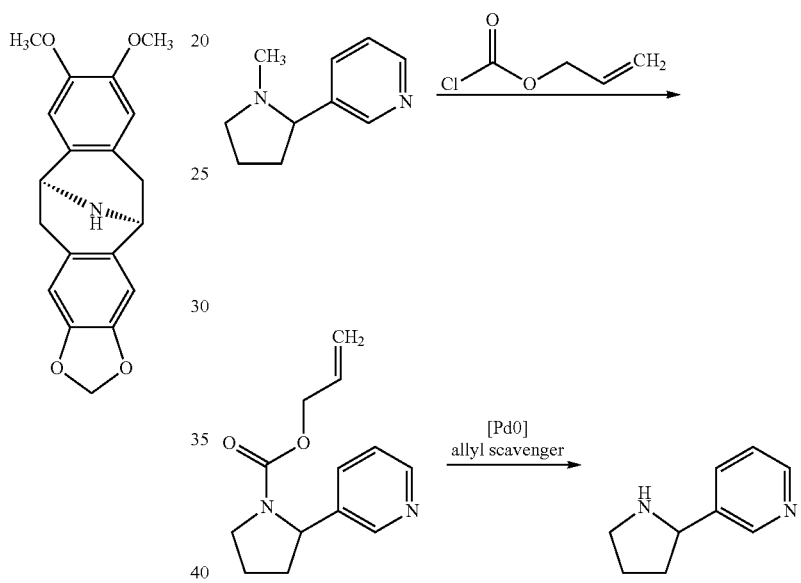

As depicted, each compound (atropine, caffeine, (+)-eschscholtzidine, galanthamine, and nicotine) can be taken up in an appropriate solvent, e.g., tert-amyl alcohol, and contacted with an allyl haloformate reagent (here allyl chloroformate) to provide the depicted carbamate intermediate. The carbamate intermediates are contacted with a transition metal catalyst in the presence of an allyl scavenger to provide the demethylated secondary amine or "nor" derivative of each compound. In certain embodiments, the tertiary amine is contacted with an allyl haloformate in the presence of an iodide salt. In certain embodiments, the iodide salt is present in a sub-stoichiometric amount. In certain embodiments, the iodide salt is present in a catalytic amount.

In one embodiment, the allyl scavenger can be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof. In another embodiment, the allyl scavenger is compound (146)

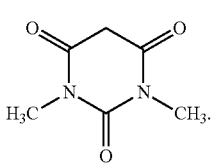

(146)

In other embodiments, the allyl haloformate employed in the reactions depicted in Schemes 24 through 28 can be prepared from an "allyl haloformate equivalent," i.e., a compound from which an allyl haloformate can readily be formed, selected from among such compounds as formulae (6), (8), (13), (23), and (46), according to the methods disclosed herein, e.g., as depicted in Schemes 11, 12, and 29.

4.7 Method for Making Compounds of Formula (1)

In one embodiment, the present disclosure provides a method for making a compound of formula (1)

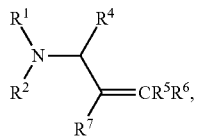

in which a tertiary amine of formula (2)

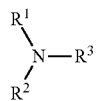

is converted to a carbamate derivative of formula (3)

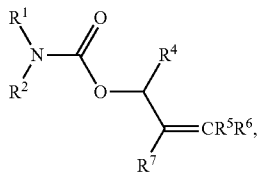

and the carbamate derivative of formula (3) is contacted with a transition metal catalyst to provide the compound of formula (1). In specific aspects of this embodiment, $R^1$, $R^2$, and $R^3$ are each independently selected from —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups, or $R^1$ and $R^2$ are taken together with the nitrogen atom to which they are bound to form a heterocyclic or heteroaryl ring of formula (5)

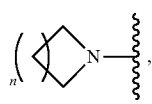

where n is an integer selected from 0, 1, 2, 3, 4, 5, 6, 7, 8, 9, 10, and 11; $R^4$ is selected from the group consisting of —H, —$(C_1$-$C_6)$ alkyl, phenyl, allyl, -2-butenyl, -3-butenyl, -4-pentenyl, -2-propynyl, -2-butynyl, -3-butynyl, -2-pentynyl,

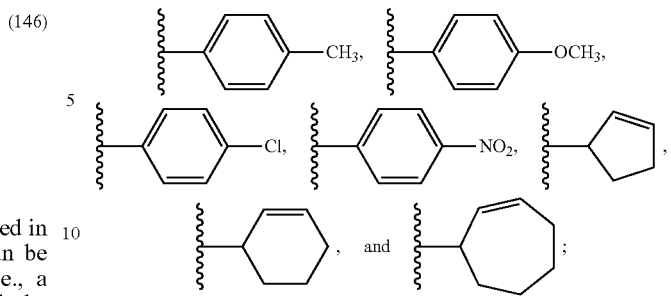

$R^5$, $R^6$, and $R^7$ are each independently selected from —H, —$(C_1$-$C_6)$ alkyl, —$(C_2$-$C_6)$ alkenyl, and —$(C_2$-$C_6)$ alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —$(C_1$-$C_6)$ alkyl; and $R^{51}$ is —$(C_1$-$C_6)$ alkyl or an oxygen protecting group. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —$(C_1$-$C_6)$ alkyl; and $R^{51}$ is —$(C_1$-$C_6)$ alkyl or an oxygen protecting group. For example, $R^6$ and $R^7$ taken together can form a methylene (i.e., —$CH_2$—) which, combined with the carbon atom to which $R^6$ and $R^7$ are attached, provides a three-membered cyclopropenyl ring, e.g., as contained in the compound of formula (18) when p is 1.

In certain other embodiments, n is an integer selected from 0, 1, 2, 3, 4, 5, 6, and 7. In further embodiments, n is an integer selected from 0, 1, 2, 3, 4, and 5. In a particular embodiment, n is an integer selected from 0, 1, 2, and 3. In another particular embodiment, n is 3.

The heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =$CH_2$, —$OR^{53}$, —$O(C_1$-$C_6)$ alkyl, —C(=O)$(C_1$-$C_6)$ alkyl, and —$(C_1$-$C_6)$ alkyl, each alkyl being either unsubstituted or substituted with 1, 2, 3, 4, or 5 independently-selected —$OR^{53}$ groups; and $R^{53}$ is —H or an oxygen protecting group. Accordingly, compounds of formula (2) include, e.g., opioid compounds. In certain embodiments, $R^{52}$ is selected from =O, =$CH_2$, —$OR^{53}$, —$O(C_1$-$C_6)$ alkyl, and —$(C_1$-$C_6)$ alkyl, where each alkyl group is either unsubstituted or substituted with 1, 2, 3, 4, or 5 independently-selected —$OR^{53}$ groups; and $R^{53}$ is —H or an oxygen protecting group.

Among the three R groups (R', $R^2$, and $R^3$) attached to the nitrogen atom of the tertiary amine of formula (1), the group removed in the dealkylation reaction can be predicted according to the following hierarchy: benzyl>allyl>cycloxhexyl>methyl (see, e.g., Cooley et al., "Amine Dealkylations with Acyl Chlorides" (1989) *Synthesis* 1-7). In certain embodiment, e.g., those in which each of $R^1$, $R^2$, and $R^3$ is an alkyl group, it may be predicted that the least sterically hindered moiety will be the group displaced in the dealkylation reaction. In addition, where $R^1$ and $R^2$ are taken together with the nitrogen atom to which they are bound to form a heterocyclic or heteroaryl ring of formula (5)

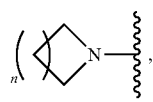

where n is as defined above, then it can be predicted that $R^3$ would be the chemical group removed in the dealkylation reaction. Moreover, the heterocyclic or heteroaryl ring of formula (5) is a monocyclic ring that is saturated, unsaturated non-heteroaryl, or heteroaryl, which is unsubstituted or substituted with 1, 2, 3, 4, or 5 independently-selected $R^{52}$ groups, or is a subunit of a polycyclic ring system comprising any combination of 1, 2, 3, 4, 5, or 6 carbocyclic, heterocyclic, aryl, or heteroaryl rings, each of which is unsubstituted or substituted with 1, 2, 3, 4, or 5 independently-selected $R^{52}$ groups. $R^{52}$ is selected from =O, =CH$_2$, —OR$^{53}$, —O(C$_1$-C$_6$) alkyl, —C(=O)(C$_1$-C$_6$) alkyl, and —(C$_1$-C$_6$) alkyl, each alkyl group being either unsubstituted or substituted with 1, 2, 3, 4, or 5 independently-selected —OR$^{53}$ groups; and $R^{53}$ is —H or an oxygen protecting group. In certain embodiments, $R^{52}$ is selected from =O, =CH$_2$, —OR$^{53}$, —O(C$_1$-C$_6$) alkyl, and —(C$_1$-C$_6$) alkyl, where each alkyl group is either unsubstituted or substituted with 1, 2, 3, 4, or 5 independently-selected —OR$^{53}$ groups; and $R^{53}$ is —H or an oxygen protecting group.

Compounds disclosed herein can contain one or more asymmetric centers and can thus give rise to enantiomers, diastereomers, and other stereoisomeric forms. In reference to compounds of formula (1) for example, as well as all other compounds described herein that contain one or more olefinic double bonds or other centers of geometric asymmetry, unless specified otherwise, it is intended to include both E and Z geometric isomers. The method disclosed herein can be used with each of the enantiomers, diastereomers, and other stereoisomeric forms of the reagents disclosed herein to provide each of the enantiomers, diastereomers, and other stereoisomeric forms of the products disclosed herein.

The transition metal catalyst mediating the decarboxylation of the compound of formula (3) to provide the compound of formula (1) can be selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, [Mo(CO)$_6$-DPPE], RhH(PPh$_3$)$_4$-P(n-Bu)$_3$, and combinations of two or more thereof. In another embodiment, the transition metal catalyst comprises 1, 2, 3, or 4 phosphine moieties. In another embodiment, the transition metal catalyst is tetrakis(triphenylphosphine)palladium[0].

The transition metal catalyst is present in an amount which enables the reaction to proceed. In certain embodiments, the transition metal catalyst is present in a substoichiometric amount. In certain embodiments, the transition metal catalyst is present in a catalytic amount. In certain embodiments, the transition metal catalyst is present in an amount of from 0.001 to 30 mol % or of any numerical value within this range. In certain embodiments, the transition metal catalyst is present in an amount of from 0.1 to 10 mol % or of any numerical value within this range (like about 5 mol %).

4.7.1 Method for Making Compound of Formula (3): Reaction With Allyl Haloformates In one embodiment, the compound of formula (3) is prepared by contacting the compound of formula (2) with a compound of formula (93)

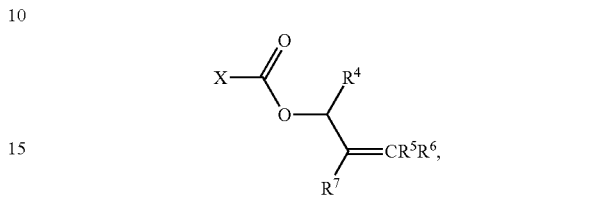

where X can be selected from —Cl, —Br, and —I, in a solvent. In certain embodiments, the contacting the compound of formula (2) with a compound of formula (93) is carried out in the presence of a base. In certain embodiments, the reaction between the compound of formula (2) and the compound of formula (93) is carried out in solvent that can be selected from the group consisting of CHCl$_3$, CH$_2$Cl$_2$, 1,2-dichloroethane, toluene, THF, ethyl acetate, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment, the solvent comprises tert-amyl alcohol. In another specific embodiment, the solvent consists essentially of tert-amyl alcohol. In another specific embodiment, the solvent is tert-amyl alcohol.

In certain embodiments, the reaction between the compound of formula (2) and the compound of formula (93) is carried out in the presence of a base selected from the group consisting of Na$_2$CO$_3$, NaHCO$_3$, KHCO$_3$, K$_2$CO$_3$, Cs$_2$CO$_3$, and combinations of two or more thereof.

In certain embodiments, the compound of formula (93) or its equivalent, e.g., an "allyl haloformate equivalent," is added to the reaction mixture containing the compound of formula (2) in a single portion. In other embodiments, the compound of formula (93) is added in a plurality of portions or portion-wise to the reaction mixture containing the compound of formula (2) throughout the course of the reaction (e.g., see Examples 3 and 18 below). For example, the compound of formula (93) can be added in 2, 3, 4, 5, 6, 7, 8, 9, 10, or more distinct portions throughout the course of the reaction. The individual quantities of the compound of formula (93) in each portion can be the same or different. Portions of the compound of formula (93) can be added at well-defined intervals during the reaction. For example, individual portions of the compound of formula (93) can be added about every 1 to 26 hours, about every 20 hours, or about every 16 hours as the reaction progresses. Alternatively, individual portions of the compound of formula (93) can be added at times during the reaction when the rate of formation of the desired product(s) diminishes.

In another embodiment, the compound of formula (93) or its equivalent, e.g., an "allyl haloformate equivalent," is added continuously to the reaction mixture containing the compound of formula (2) throughout the course of the reaction. In another embodiment, continuous addition is achieved by preparing a solution of the compound of formula (93) in the reaction solvent, e.g., a dilute solution in one embodiment, adding the dilute solution to an addition funnel, and slowly dropping the dilute solution into the reaction mixture containing the compound of formula (2). In another embodiment, continuous addition is achieved by filling a hypodermic syringe equipped with a mechanically-driven plunger with the dilute solution of the compound of formula (93) and adding the dilute solution through a hypodermic needle into the reaction mixture containing the compound of formula (2). In another embodiment, continuous addition is achieved by using a continuous or semi-continuous reactor in which the compound of formula (93) is added to a stream containing the compound of formula (2). The volume of the dilute solution, the concentration of the dilute solution, and/or the rate at which the dilute solution is added to the reaction mixture can be varied depending on the time needed for the reaction to achieve substantial completion.

Methods of carrying out portion-wise and continuous addition of a liquid reagent to a reaction mixture are known in the art. For example, U.S. Pat. Nos. 2,191,786, 2,583,420, 3,355,486, 3,749,646, 4,217,787, 6,486,692, and 6,994,827, each of which is hereby incorporated by reference in its entirety, disclose chemical reactors in which one reagent is added incrementally to a solution containing additional reagents. Incremental addition is known in the art as the metering-in of a reagent over a finite period of time in contrast with the dumping of the total reagent into the reactor at once. The term incremental addition includes addition using a continuous stream, addition using a variable stream, addition intermittently using separate portions, and other related methods. See U.S. Pat. No. 4,217,287 (col. 2, lines 56-62).

In certain embodiments, a stoichiometric excess of the compound of formula (93) or its equivalent, e.g., an "allyl haloformate equivalent," is added relative to the compound of formula (2). The stoichiometric (molar) ratio, i.e., the total amount of the compound of formula (93) to the total amount of the compound of formula (2), can vary from about 1.2:1 to about 20:1 in one embodiment, from about 1.8:1 to about 9:1 in another embodiment, from about 1.9:1 to about 7:1 in another embodiment, and from about 1.9:1 to about 4.5:1 in another embodiment. It has been discovered that for embodiments in which the compound of formula (93) is added portion-wise or continuously throughout the course of the reaction, the quantity of the compound of formula (93) required to reach a desired level of conversion to the compound of formula (3) is reduced relative to embodiments where the full amount of the compound of formula (93) is added only in the beginning of the reaction. In these portion-wise or continuous embodiments, the stoichiometric (molar) ratio of the compound of formula (93) to the compound of formula (2) ranges from about 1.9:1 to about 7:1 in one embodiment, from about 1.9:1 to about 4.5:1 in another embodiment, from about 1.5:1 to about 3:1 in another embodiment, and from about 1.5:1 to about 2.2:1 in another embodiment. Thus, the overall molar ratio of the compound of formula (93) to the compound of formula (2) needed to produce the desired yield of the compound of formula (3) can be reduced. Minimizing the quantity of the compound of formula (93) employed can be advantageous when that compound possesses undesirable properties, e.g., allyl chloroformate (compound (102)), which is flammable, toxic, and not easily handled and/or disposed of.

4.7.2 Method for Making Compounds of Formula (3): β-Carbon Elimination of a Single Leaving Group In another embodiment, the compound of formula (3) is prepared by contacting the compound of formula (2) with a compound of formula (6)

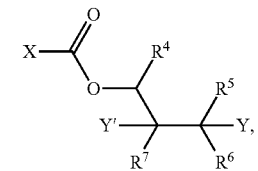

in which one of Y and Y' is a leaving group and the other is —H, in a solvent to provide a compound of formula (7)

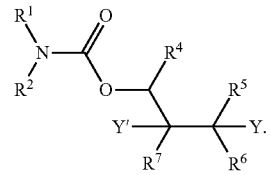

The compound of formula (7) can be converted to the compound of formula (3) as disclosed herein.

In particular aspects of this embodiment, the leaving group is selected from —Cl, —Br, —I, —OS(O)$_2$C$_4$F$_9$, —OS(O)$_2$CF$_3$, —OS(O)$_2$F, -para-toluene sulfonate, and —OS(O)$_2$CH$_3$. In certain embodiments, the leaving group is a halogen selected from —Cl, —Br, and —I. In other embodiments, the leaving group is —Br.

In certain embodiments, the contacting of a compound of formula (2) with a compound of formula (6) is carried out in the presence of a base, which can, e.g., be selected from the group consisting of Na$_2$CO$_3$, NaHCO$_3$, KHCO$_3$, K$_2$CO$_3$, Cs$_2$CO$_3$, and combinations of two or more thereof.

In certain embodiments, conversion of the compound of formula (7) to the compound of formula (3) is carried out under conditions and/or in the presence of a reagent that promotes elimination of the leaving group, Y or Y'. In one aspect of this embodiment, elimination of the leaving group Y is promoted by heat. In another aspect, elimination of the leaving group Y is promoted by exposure to light of an appropriate wavelength. In a further aspect, elimination of the leaving group Y is promoted by including a reagent that is a base. Where the reagent is a base, it can, for example, be selected from the group consisting of NaOH, KOH, sodium tert-butoxide (tert-BuONa), potassium tert-butoxide (tert-BuOK), lithium di-iso-propylamide, sodium hydride, tert-butyl lithium, LiAlH$_4$, AlCl$_3$, triethylamine, sodium ethoxide, lithium diethyl amide (LiN(Et)$_2$), potassium acetate (KOAc), and combinations of two or more thereof.

The reaction is carried out in a suitable solvent that, e.g., can be selected from the group consisting of DMSO, 2-methyl-propan-2-ol, benzene, hexane, THF, 1,4-dioxane, DMF, diethylether, acetone, methanol, ethanol, toluene, and combinations of two or more thereof.

4.7.3 Method for Making Compounds of Formula (3): α,β-Carbon Elimination of Two Leaving Groups In one aspect of this embodiment, the compound of formula (3) is prepared by elimination of two leaving groups (Z and Z') from a compound of formula (9)

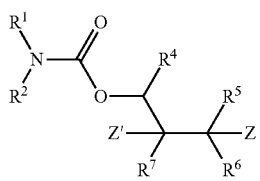

to provide the compound of formula (3), where Z and Z' are each leaving groups independently selected from —Cl, —Br, and —I. In certain embodiments, Z and Z' are each —Br while, in other embodiments, Z and Z' are each —Cl. Elimination of leaving groups Z and Z' is carried out in the presence of a transition metal catalyst by contacting the compound of formula (9) under conditions and/or in the presence of a reagent that promotes elimination of the leaving groups to provide the compound of formula (3). In one illustrative embodiment, Z and Z' are each —Br and elimination of both Br atoms is carried out in the presence of a promoting reagent, e.g., ethylmagnesium bromide and tributyltin hydride. In certain embodiments, the catalyst is, for example, nickel diphenylphosphinoethane dichloride [Ni(DPPE)Cl$_2$]. This reaction can be carried out in a solvent selected, e.g., from among THF and acetonitrile, at temperature within the range of from about –20° C. to about 40° C.

In one embodiment, the compound of formula (9) can be formed by contacting a compound of formula (2) with a compound of formula (8)

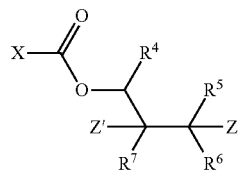

where X is selected from —Cl, —Br, and —I, in a solvent in the presence of base to provide the compound of formula (9).

This reaction can be carried out in a solvent selected from the group consisting of CHCl$_3$, CH$_2$Cl$_2$, 1,2-dichloroethane, toluene, THF, ethyl acetate, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent comprises, consists essentially, or is (i.e., consists of) a tertiary alcohol selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof.

In a specific embodiment, the solvent comprises tert-amyl alcohol. In another specific embodiment, the solvent consists essentially of tert-amyl alcohol. In another specific embodiment, the solvent is tert-amyl alcohol.

This reaction can be carried out in the presence of a base, which can, e.g., be selected from the group consisting of Na$_2$CO$_3$, NaHCO$_3$, KHCO$_3$, K$_2$CO$_3$, Cs$_2$CO$_3$, and combinations of two or more thereof. In certain embodiments, the base is selected from the group consisting of NaHCO$_3$, KHCO$_3$, and combinations thereof.

4.7.4 Method for Making Compounds of Formula (3): Carbamate/Allyl Alcohol Exchange In another embodiment, compounds of formula (3) are prepared in two steps. In the first, a compound of formula (2) is contacted with a haloformate compound of formula (10)

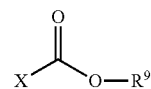

to provide a carbamate of formula (11)

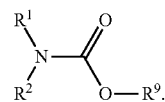

The compound of formula (11) is then contacted with an alkoxide derivative of an allyl alcohol of formula (12)

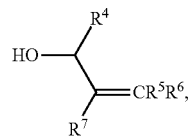

to provide the compound of formula (3). In one aspect of this embodiment, the alkoxide derivative is a compound of formula NaO—CH$_2$CH=CH$_2$ (i.e., a compound of formula (61) in which M is Na).

In one embodiment, the alkoxide derivative is NaO—CH$_2$CH=CH$_2$ which is prepared by reacting sodium with a 15-30 fold molar excess of HO—CH$_2$CH=CH$_2$ to provide an alkoxide solution which is contacted with a solution of a compound of formula (11), and the mixture is heated at 100° C. for four hours and then allowed to stand at a temperature of about 20° C. for about 16 hours.

4.7.5 Method for Making Compounds of Formula (3): Alkyne Hydrogenation

In another embodiment, the compound of formula (3) is prepared by contacting the compound of formula (2) with a haloformate of formula (13)

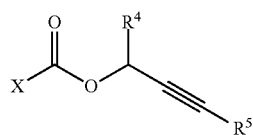

to provide a compound of formula (14)

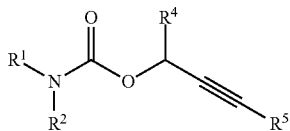

and then selectively hydrogenating the compound of formula (14) to provide an allyl carbamate derivative of formula (16)

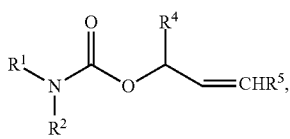

which is a compound of formula (3) in which $R^6$ and $R^7$ are each hydrogen. The compound of formula (16) can be converted to a compound of formula (15)

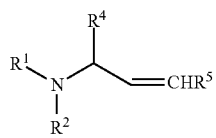

using the transition metal-catalyzed, decarboxylation reactions disclosed herein.

In one embodiment, reduction (hydrogenation) of the alkyne to the alkene is carried out in methanol with hydrogen and quinoline in the presence of 5% Lindlar catalyst. In another embodiment, the reduction is carried out in the presence of 1.0 M NaBH$_4$, hydrogen, diethyl amine and Ni[II]acetate in aqueous methanol (see also U.S. Pat. No. 6,335,459, which is hereby incorporated by reference in its entirety).

4.8 Method for Making Compounds of Formula (17)

In a further embodiment, the compound of formula (1) is a compound of formula (17)

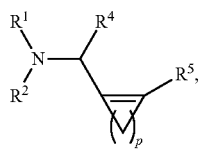

which can be prepared by contacting a compound of formula (2) with a compound of formula (19)

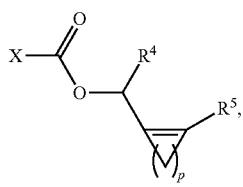

to provide a compound of formula (18)

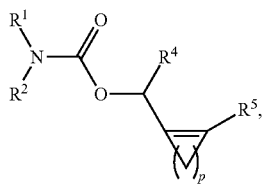

which is a compound of formula (3).

In certain embodiments, the compound of formula (19) is prepared in two steps which will be described using cyclopropene-1-methanol as exemplary compound in the following. In the first step, cyclopropene-1-methanol

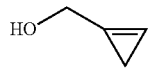

(compound (141)) is synthesized from 1,1,2-tribromocyclopropane-2-methanol as described by Dulayymi et al. (1996) *Tetrahedron* 52(10):3409-3424, which is hereby incorporated by reference in its entirety. The cyclopropene-1-methanol is then reacted with phosgene to provide the following chloroformate reagent

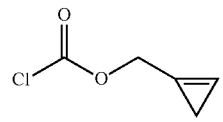

(compound (119)), which is a compound of formula (19) in which X is Cl, p is 1, and $R^4$ and $R^5$ are each H. Condensation of an allyl alcohol with phosgene is a typical method that can be used to provide the corresponding allyl chloroformate reagents that can be used to dealkylate tertiary amines. However, other methods and reagents can be utilized for the conversion of an allyl alcohol to the corresponding haloformate reagent. The resulting allyl carbamate derivatives can be decarboxylated using the transition metal-catalyzed reactions disclosed herein to provide N-allyl derivatives in which in allyl moiety of the allyl alcohol has been substituted for an alkyl group of the tertiary amine.

The compound of formula (18) can be contacted with a transition metal catalyst to provide the compound of formula (17). In certain embodiments, p is 1 and the compound of formula (17) has the following structure:

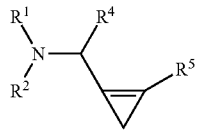

while, in other embodiments, p is 2 and the compound of formula (17) has the following structure:

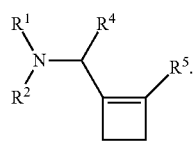

4.9 Method for Making Compounds of Formula (20)

In a further embodiment, the present disclosure provides a method for making a compound of formula (20)

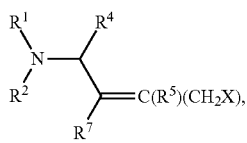

in which a compound of formula (2) is contacted with a compound of formula (21)

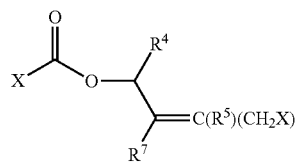

in a solvent to provide a compound of formula (22)

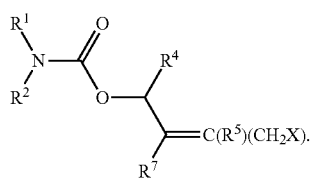

In certain embodiments, the contacting of the compound of formula (2) with the compound of formula (21) is carried out in the presence of a base. X can be selected from —Cl, —Br, and —I. In a particular embodiment, X is —I. In that particular embodiment, the compound of formula (21) is compound of formula (21'), i.e.,

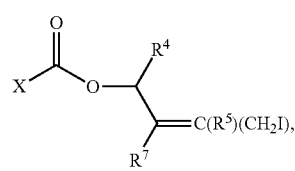

and the compound of formula (22) is compound of formula (22'), i.e.,

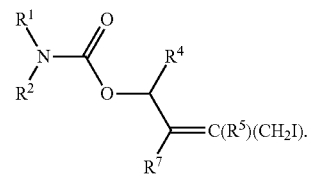

The compound of formula (22) can then be decarboxylated in a transition metal-catalyzed reaction to provide the compound of formula (20).

In certain embodiments, the compound of formula (21) has the following chemical structure:

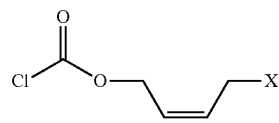

(where X is —I, the previous molecule is compound (142)), that is prepared by reacting an alcohol of the following formula

(where X is —I, the previous molecule is compound (143)) with phosgene to provide the depicted chloroformate ((Z)-4-iodobut-2-enyl carbonochloridate). For example, the alcohol ((Z)-4-iodobut-2-en-1-ol), can be prepared as described by Balas et al. (2009) *J. Med. Chem.* 52:1005-1017, which is hereby incorporated by reference in its entirety. Again, condensation of an allyl alcohol with phosgene is a typical method that can be used to provide the corresponding allyl chloroformate reagents that can be used to dealkylate tertiary amines. However, other methods and reagents for conversion of an allyl alcohol to the corresponding haloformate reagent can also be used. The resulting allyl carbamate derivatives can be decarboxylated using the transition metal-catalyzed reactions disclosed herein to provide N-allyl derivatives in which in allyl moiety of the allyl alcohol has been substituted for an alkyl group of the tertiary amine.

4.10 Method for Making Compounds of Formula (1): β-Carbon Elimination

The present disclosure also provides a method for making compounds of formula (1) that includes transition metal-catalyzed reaction in which a compound of formula (24)

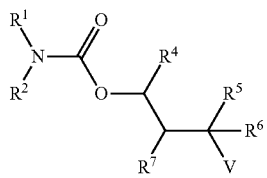

is converted to a compound of formula (1). In one illustrative embodiment, a compound of formula (2) is contacted with a compound of formula (23)

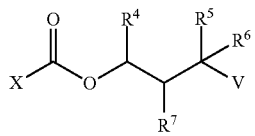

in a solvent to provide the compound of formula (24), where V is a leaving group. In certain embodiments, the contacting of the compound of formula (2) and the compound of formula (23) is carried out in the presence of a base.

The compound of formula (24) is contacted with a transition metal catalyst to provide an allyl carbamate intermediate of formula (3)

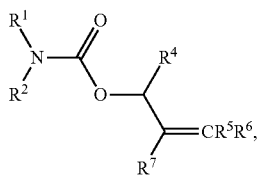

which is then decarboxylated to the corresponding N-allyl derivative

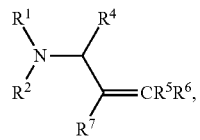

a compound of formula (1), in a second transition metal-catalyzed reaction.

Applicants believe, without wishing to be held to that belief, that the reactions of this embodiment involve the intermediates depicted below and proceed with both a metal insertion reaction and a β-hydride elimination, as depicted in the following Scheme 29, illustrated with an exemplary palladium-containing transition metal catalyst.

As indicated in Scheme 29, a compound of formula (24)

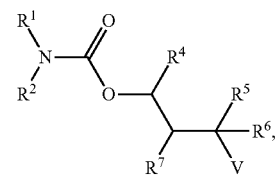

is contacted with a transition metal catalyst, which can insert into the indicated bond to provide an intermediate of formula (72)

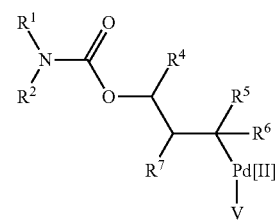

that undergoes β-hydride elimination to provide an intermediate of formula (3)

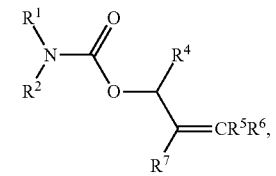

which in turn, reacts with the transition metal catalyst present in the reaction mixture to provide the decarboxylated N-allyl compound of formula (1)

Scheme 29

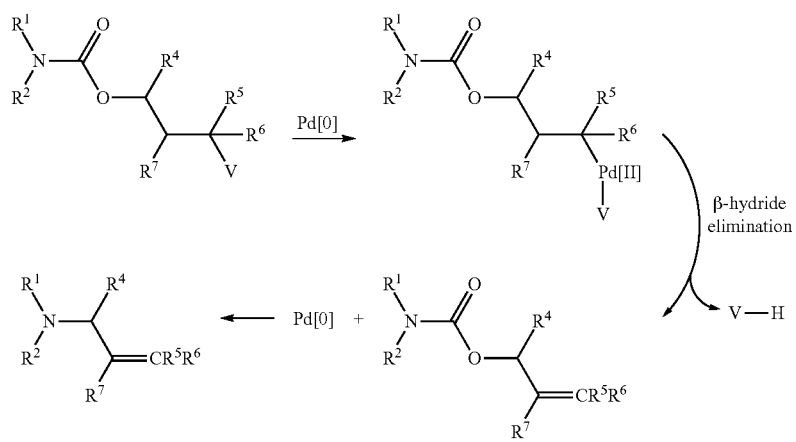

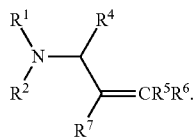

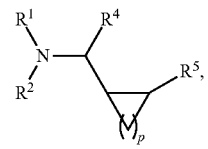

The reactions of Scheme 29 therefore provide a "single step" transition metal-catalyzed process for the preparation of compounds of formula (1) from compounds of formula (24) (e.g., see Scheme 12 which illustrates the use of the reactions of Scheme 29 for the preparation of, e.g., compound (104), naloxone).

The leaving group V, can be selected, for example, from among —Cl, —Br, —I, —OS(O)$_2$C$_4$F$_9$, —OS(O)$_2$CF$_3$, —OS(O)$_2$F, -para-toluene sulfonate, —OS(O)$_2$CH$_3$, and —B(O(C$_1$-C$_4$) alkyl)$_2$.

4.11 Method for Making Compounds of Formula (1): Allylation of Secondary Amines

In a further embodiment, compounds of formula (1) are prepared by

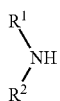

contacting a compound of formula (25) with a compound of formula (26)

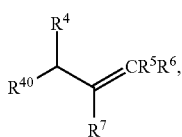

where R$^{40}$ is —OC(O)CH$_3$ or —N(CH$_3$)$_2$, in a solvent in the presence of a transition metal catalyst.

In certain embodiments, R$^{40}$ is —O(C)OX where X is selected from —Cl, —Br, and —I.

In one embodiment, allylation of noroxymorphone with allyl acetate is accomplished by combining noroxymorphone with triethylamine (3 equivalents), toluene (50 mL) and tetrakis(triphenylphosphine)palladium[0] (0.1 equivalent), and heating the mixture at 80° C. for 64 hours. The mixture is cooled to a temperature of about 20° C. and filtered through a plug of CELITE and the filtrate was concentrated under reduced pressure. Naloxone is isolated from the concentrated filtrate using normal extractive procedures.

In certain embodiments, allylation of noroxymorphone with dimethylallylamine is accomplished by combining noroxymorphone, 1,4-bis(diphenylphosphino)-butane (0.1 equivalent), palladium[II] acetate (0.05 equivalent), acetic acid (2 equivalents), and DMF (40 mL) and stirring the mixture at 50° C. for 16 hours.

4.12 Method for Making Compounds of Formula (27)

The present disclosure also provides a method for making compounds of formula (27)

in which a compound of formula (2) is contacted with a compound of formula (19)

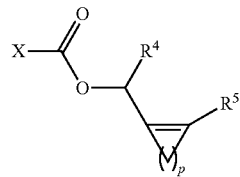

to provide a compound of formula (18)

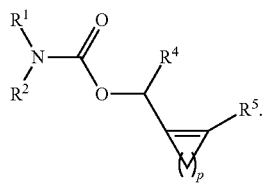

The compound of formula (18) is then decarboxylated in the presence of a transition metal catalyst to provide a compound of formula (17)

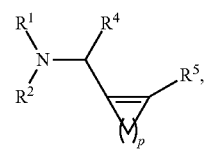

which is then hydrogenated to provide the compound of formula (27). Variable p is an integer selected from 1, 2, 3, 4, 5, 6, and 7. Where p is 1, the compound of formula (27) is a compound of the following formula

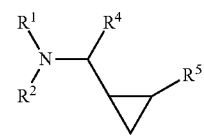

(formula (28)), and where p is 2, the compound of formula (27) is a compound of the following formula

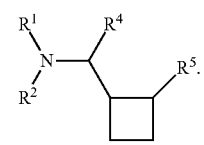

As noted above, compounds of formula (19) can be prepared in two steps. The unsaturated alcohols, e.g.,

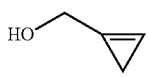

(compound (141)), can be prepared as described by Dulayymi et al. (1996) *Tetrahedron* 52(10):3409-3424, which is hereby incorporated by reference in its entirety. Those alcohols can then reacted with phosgene to provide the haloformate reagents of formula (19). Other methods and reagents can also be used for conversion of an allyl alcohol to the corresponding haloformate reagent of formula (19).

Haloformate reagents of formula (19) are condensed with a tertiary amine of formula (2) as described in Examples 1 and 2, below, to provide the carbamate intermediates of formula (18) that are decarboxylated in transition metal-catalyzed reactions, as described in Examples 4, 5 and 6, to provide compounds of formula (17). Hydrogenation of the compounds of formula (17) is carried out, in one embodiment, in the presence of precious metal catalyst, which can be dispersed on a solid support, e.g., Pd/C or Pt/C, under a hydrogen atmosphere. Hydrogenation can also be accomplished using additional methods disclosed herein including, without limitation, transfer hydrogenation.

4.13 Method for Making Compounds of Formula (28)

The present disclosure also provides a method for making a compound of formula (28)

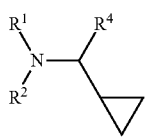

in which a compound of formula (2) is contacted with a compound of formula (29)

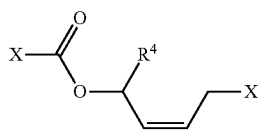

to provide a carbamate derivative of formula (30)

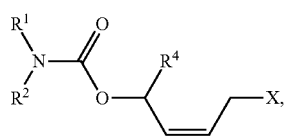

which is decarboxylated in a transition metal-catalyzed reaction to provide a compound of formula (31)

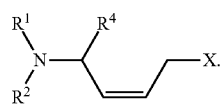

The compound of formula (31) is then contacted with a zinc-containing reagent, e.g., zinc[0], in the presence of an iodide salt to provide the compound of formula (28). X is a halogen selected from —Cl, —Br, and —I. In specific embodiments, X is —I.

In certain embodiments, the iodide salt is present in a sub-stoichiometric amount. In certain embodiments, the iodide salt is present in a catalytic amount.

Compounds of formula (29) are prepared by condensation of the corresponding alcohol with phosgene as noted above, where the alcohol is prepared according to the methods disclosed by Balas et al. (2009) *J Med. Chem.* 52:1005-1017. The zinc-promoted allyl iodide cyclization whereby compounds of formula (31) are converted to compounds of formula (28) are carried out according to the method disclosed by Sakuma et al. (2005) *Tetrahedron* 61:10138-10145, which is hereby incorporated by reference in its entirety. In certain embodiments, compounds of formula (31) are contacted with zinc powder (3 equivalents) in 2:1 tert-butanol/H$_2$O at reflux temperature under an argon atmosphere for 0.5 hours to about 24 hours. Once the reaction is deemed to be complete, the mixture can be filtered and the solvent removed by evaporation. The desired compounds of formula (28) are then isolated using standard chromatographic methods and equipment.

4.14 Method for Making Compounds of Formula (32)

Processes for the preparation of compound of formula (32)

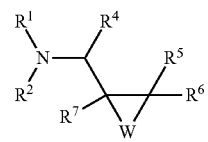

are also provided. These processes include contacting a compound of formula (2) with a haloformate reagent of formula (93) to provide a compound of formula (3) as described, e.g., in Section 4.7 above, and the compound of formula (3), in turn is converted to a compound of formula (1), using the methods disclosed herein. The compound of formula (1) can then be converted to a compound of formula (32) as depicted in Scheme 30 and as described below.

Scheme 30

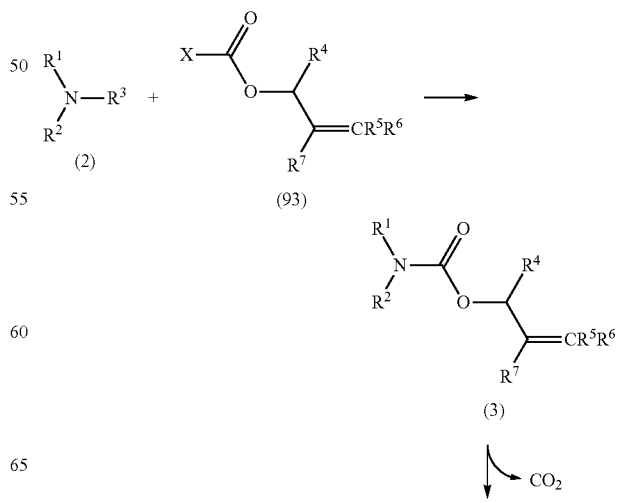

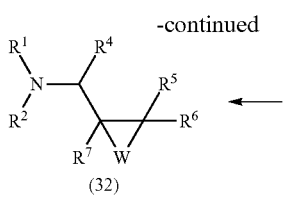

(32) ← (1)

In one embodiment, the compound of formula (1) is contacted with meta-chloroperbenzoic acid or ortho-chloroperbenzoic acid to provide a compound of formula (33)

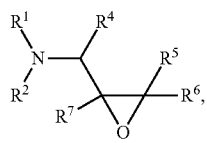

a compound of formula (32) in which W is O.

In one embodiment, compounds of formula (1) are taken up in a solvent and contacted with from about 1 equivalent to about 6 equivalents of m-chloro peroxybenzoic acid at a temperature within the range of from about 0° C. to about 40° C. for a period of time within the range of from about 0.5 hours to about 24 hours. In certain embodiments, the solvent is methylene chloride while, in other embodiments, the solvent is benzene or a mixture of benzene and methylene chloride. In certain embodiments, the reaction is carried out at about 20° C.

In another embodiment, the compound of formula (33) is contacted with NaN$_3$ and NH$_4$Cl to provide a compound of formula (34)

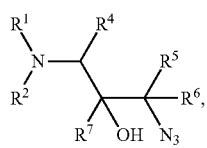

which is contacted with, e.g., PPh$_3$, to provide a compound of formula (35)

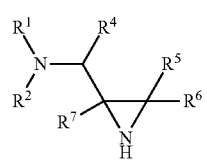

according to the methods disclosed by Chiappe et al. (1998) Asymmetry 9:4079-4088, which is hereby incorporated by reference in its entirety.

In certain embodiments, the compound of formula (33) is taken up in methanol:water (4:1) and NaN$_3$ (4.5 equivalents) and NH$_4$Cl (2.5 equivalents) added. The mixture is stirred at 80° C. and the reaction monitored until deemed complete, e.g., 18-20 hours. The intermediate azido alcohols of formula (34) can be recovered using normal work-up procedures. The recovered material can then be taken up in a suitable solvent, e.g., acetonitrile, and PPh$_3$ added (1 equivalent). The mixture is stirred at about 20° C. until the evolution of gas (N$_2$) is observed and then at reflux temperature overnight (about 16 hours). The desired product of formula (35) is isolated and characterized using normal work-up procedures and analytical methodology.

In a still further embodiment, the compound of formula (1) is contacted with compound (144)

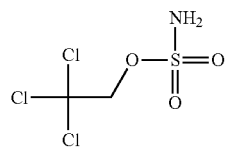

in the presence of iso-propylCu(dibenzoylmethane) and iodosylbenzene to provide a compound of formula (36)

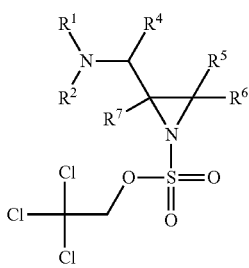

according to the methods disclosed by Xu et al. (2008) Org. Lett. 10(7):1497-1500 and Guthikonda et al. (2002) J. Am. Chem. Soc. 124:13672-13673, which are hereby incorporated by reference in their entireties.

In one embodiment, the compound of formula (1) is taken up in chlorobenzene and reacted with 10% IPrCu(dibenzoylmethane), iodosobenzene (PhIO) (1.5 equivalents), and trichloroethylsulfamate ester at about 25° C. for about 12 to about 30 hours, or until such time as the reaction is deemed complete, under an inert atmosphere, e.g., a nitrogen atmosphere. Once the reaction is deemed complete, the desired product of formula (36) is isolated and characterized using normal work-up procedures and analytical methodology.

In another embodiment, the compound of formula (1) is contacted with CHI$_3$ and CrCl$_2$ to provide a compound of formula (37)

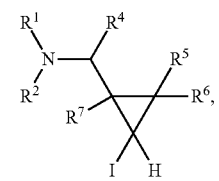

and the compound of formula (37) is contacted with a zinc-containing reagent, e.g., zinc[0], in the presence of acetic acid to provide a compound of formula (38)

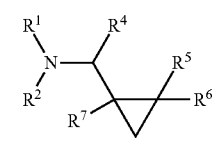

according to the methods disclosed in Takai et al. (2003) *J. Am. Chem. Soc.* 125:12990-12991, which is hereby incorporated by reference in its entirety.

In another embodiment, the compound of formula (1) is taken up in THF, and CHI$_3$ (1.5 equivalents), CrCl$_2$ (4 equivalents), and N,N,N',N'-tetraethylethylenediamine (TEEDA) are added. The reaction is carried out at about 25° C. until deemed complete. The product, a compound of formula (37), is isolated and characterized using normal work-up procedures and analytical methodology. Removal of the iodide group, converting the compound of formula (37) to a compound of formula (38), is accomplished by contacting the former compound with zinc in acetic acid, according to methods disclosed in Martin et al. (1994) *J. Am. Chem. Soc.* 116:4493-4494, which is hereby incorporated by reference in its entirety.

In another embodiment, the compound of formula (1) is contacted with CH$_2$I$_2$ to provide the compound of formula (38) directly, according to methods disclosed in U.S. Patent Application Publication No. US 2007/0142634 A1, and Aggarwal et al. (2003) *Org. Lett.* 5(23):4417-4420, each of which is hereby incorporated by reference in its entirety. In one embodiment, the compound of formula (1) is taken up in methylene chloride at 0° C. and contacted with the zinc-containing reagent diethyl zinc (5 equivalents) followed by diiodomethane (10 equivalents). The reaction is warmed to a temperature of about 20° C. and stirred for about 16 hours. The reaction is quenched and the desired product of formula (38) is isolated and characterized using normal work-up procedures and analytical methodology. In other embodiments, the zinc-containing reagent can be selected from the group consisting of diethyl zinc, zinc dust, zinc-copper couple, and combinations thereof.

4.15 Method for Making Compounds of Formula (39)

The present disclosure also provides a method for making a compound of formula (39), in which a compound of formula (1), prepared by the processes disclosed in section 4.7 above, is hydrogenated to provide the compound of formula (39)

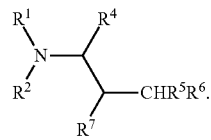

In certain embodiments, the compound of formula (1) is taken up in a suitable solvent, a catalyst added, and the mixture contacted with a hydrogen atmosphere at a temperature and for a time sufficient to convert the compound of formula (1) to a compound of formula (39). In representative embodiments, the solvent is selected from the group consisting of ethanol, methanol, dichloromethane, 1:1 ethylacetate:methanol, THF, and combinations of two or more thereof. The catalyst, for example, can be selected from the group consisting of palladium on carbon (Pd/C), platinum on carbon (Pt/C), and combinations thereof. The hydrogen pressure is typically between 15 psi and 60 psi. The hydrogenation is typically carried out at a temperature between about 15° C. and 30° C. for a period of time of from about 1 hour to about 24 hours.

4.16 Method for Making Compounds of Formula (40)

In another embodiment, the present disclosure provides a process for making compounds of formula (40)

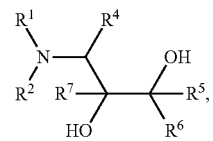

in which compounds of formula (1), prepared by the processes disclosed in section 4.7 above, are oxidized to provide the compound of formula (40). In certain embodiments, the oxidation is carried out in the presence of osmium tetroxide and N-methyl morpholine N-oxide. In one embodiment, the compound of formula (1) is taken up 1:1 water: THF and contacted with 0.025 equivalents of osmium tetroxide and 15 equivalents of N-methyl morpholine N-oxide for a time within the range of from about 6 hours to about 30 hours, or within the range of from about 12 to about 24 hours, and at a temperature within the range of from about 10° C. to about 30° C., or a temperature within the range of from about 15° C. to about 25° C. In certain embodiments, the reaction is carried out for 18 hours at a temperature of 20° C.

4.17 Method for Making Compounds of Formula (41)

As noted above, the present disclosure provides processes for preparing N-allyl amines from tertiary N-alkyl amines involving, inter alia, haloformate-promoted N-dealkylation of a tertiary amine (e.g., a compound of formula (2)) and a subsequent transition metal-catalyzed allylic decarboxylation (e.g., of a compound of formula (3)) to provide the N-allyl amine (e.g., a compound of formula (1)). The processes disclosed herein are also useful for preparing N-allyl amines from compounds (tertiary amines) comprising the structural elements of compounds of formula (2), e.g., from alkaloids, and more particularly, from opioids.

Accordingly, in a particular embodiment, the present disclosure provides a method for making compound of formula (41)

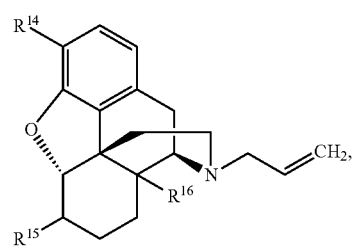

in which a compound of formula (95)

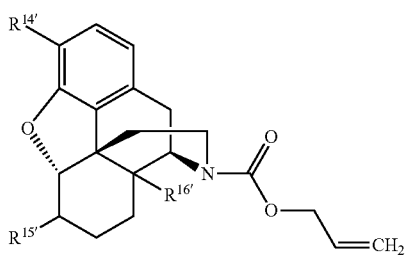

is contacted with a transition metal catalyst in a solvent to provide the compound of formula (41), where $R^{14}$ and $R^{16}$ are each independently selected from —OH, —H, and —OR$^{17}$; R$^{15}$ is selected from —OH, —H, —OR$^{17}$, =O, and =CH$_2$; and R$^{17}$ is an oxygen protecting group. As discussed above, e.g., in connection with the compound of formula (95), R$^{14'}$, R$^{15'}$, and R$^{16'}$ are as defined previously.

In a particular embodiment, R$^{14}$ and R$^{16}$ are each —OH, and R$^{15}$ is =O, and therefore the compound of formula (41) is naloxone.

In one embodiment of this method, R$^{14'}$ is selected from —OC(O)OCH$_2$CH=CH$_2$, and —OH and R$^{16}$ is —OH. In another embodiment, R$^{14}$, R$^{14'}$, R$^{16}$, and R$^{16'}$ are each —OH and R$^{15}$ and R$^{15'}$ are each =O.

In a further embodiment, the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, [Mo(CO)$_6$-DPPE], RhH(PPh$_3$)$_4$-P(n-Bu)$_3$, and combinations of two or more thereof. In another embodiment, the transition metal catalyst comprises 1, 2, 3, or 4 phosphine moieties. In another embodiment, the transition metal catalyst is tetrakis(triphenylphosphine)palladium[0].

In certain embodiments, the transition metal catalyst is present in a sub-stoichiometric amount. In certain embodiments, the transition metal catalyst is present in a catalytic amount. In certain embodiments, the transition metal catalyst is present in an amount of from 0.001 to 30 mol % or of any numerical value within this range. In certain embodiments, the transition metal catalyst is present in an amount of from 0.1 to 10 mol % or of any numerical value within this range (like about 5 mol %).

In another embodiment, the decarboxylation reaction is carried out in a solvent selected from the group consisting of CHCl$_3$, CH$_2$Cl$_2$, 1,2-dichloroethane, toluene, THF, ethyl acetate, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In certain embodiments, the oxygen protecting group, R$^{17}$, is selected from the group consisting of tert-butyldiphenylsilyl, tert-butyl-dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, para-methoxybenzyl, methylthiomethyl, pivaloyl, methyl, ethoxyethyl, triphenylmethyl, —C(O)(C$_1$-C$_4$) alkyl, —C(O)OR$^{18}$, and —(C$_1$-C$_6$) alkyl, each alkyl being unsubstituted or substituted with 1, 2, 3, 4, or 5 independently-selected R$^{21}$ groups; R$^{18}$ is —(C$_1$-C$_6$) alkyl, —(C$_2$-C$_6$) alkenyl, or —(C$_2$-C$_6$) alkynyl, each alkyl, alkenyl, and alkynyl being unsubstituted or substituted with 1, 2, 3, 4, or 5 independently-selected R$^{21}$ groups; and each R$^{21}$ is independently selected from —OH, —Cl, —Br, —I, —NH$_2$, —CN, and phenyl.

4.17.1 Method for Making Compounds of Formula (41): 3-Ether Hydrolysis

In another embodiment, the present disclosure provides a method for making a compound of formula (41), in which moiety R$^{14}$ is —OH, thereby providing a compound of formula (44)

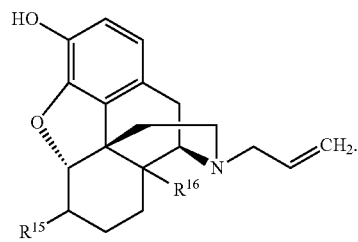

In this embodiment, the compound of formula (44) can be prepared by contacting a compound of formula (43)

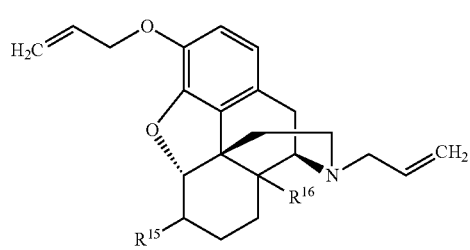

with base to provide the compound of formula (44), where R$^{16}$ is selected from —OH, —H, and —OR$^{17}$; R$^{15}$ is selected from —OH, —H, —OR$^{17}$, =O, and =CH$_2$; and R$^{17}$ is an oxygen protecting group. In certain embodiments, R$^{15}$ is =O and R$^{16}$ is —OH and, therefore, the compound of formula (44) is naloxone.

In particular embodiments, the base is selected from the group consisting of Na$_2$CO$_3$, NaHCO$_3$, KHCO$_3$, K$_2$CO$_3$, Cs$_2$CO$_3$, NaOH, KOH, LiOH, and combinations of two or more thereof.

In other embodiments, the allyl ether, e.g., of compound (143), can be cleaved (1) in the presence of Pd/C, para-toluene sulfonic acid in water or methanol at a temperature within the range of from about 60° C. to about 80° C. for about 6 hours (see, e.g., Boss et al. (1976) Angw. 24Chem., Int. Ed., Engl. 15:558); (2) in the presence of selenium dioxide/acetic acid in dioxane at reflux temperature for about one hour (see, e.g., Kariyone et al. (1970) Tetrahedron Lett. 11(33):2885-2888); (3) in the presence of NaAlH$_2$(OCH$_2$CH$_2$OCH$_3$), in toluene at reflux temperature for about ten hours (see, e.g., Kametani et al. (1976) J. Org. Chem. 41:2545); (4) in the presence of Ph$_3$P/Pd(OAc)$_2$ in formic acid at about 90° C. for one hour (see, e.g., Hey et al. (1973) Angew. Chem., Int. Ed., Engl. 12:928); (5) in the presence of a Pd[0] catalyst, Bu$_3$SnH, in acetic acid and para-nitrophenol (see, e.g., Four et al. (1982) Tetrahedron Lett. 23:1825); (6) in the presence of Pd(Ph$_3$P)$_4$ and LiBH$_4$ in THF (see, e.g., Bois-Choussey et al. (1996) J. Org. Chem. 61:9309); in this embodiment, NaBH$_4$ can also be used as an allyl scavenging agent (see, e.g., Beugelmans et al. (1994) Tetrahedron Lett. 35:4349); (7) in the presence of Pd(Ph$_3$P)$_4$ and PhSiH$_3$ for about 0.5 hours (see, e.g., Dessolin et al. (1995) Tetrahedron Lett. 36:5741); (8) in the presence of bis(benzonitrile)palladium (II) chloride, in benzene at reflux temperature for from about 16 hours to about 20 hours (see, e.g., Bruce et al., "Cleavage of Allyl Phenyl Ethers by Bis(benzonitrile)palladium (II) Chloride" (July 1981) J. Chem. Res. Synop. No. 7, p. 193); (9) in the presence of RhCl$_3$ in ethanol at reflux temperature (see, e.g., Martin et al. (1982) J. Org. Chem. 47:1513); (10) in the presence of LiPPh$_2$ in THF at reflux temperature for about four hours (see, e.g., Mann et al., "761. The Dealkylation of Alkyl Aryl Ethers and Sulphides by Diaryl-phosphide and -arsenide Ions" (1965) *J. Chem. Soc.* pp. 4120-4127); (11) in the presence of $SiCl_4$ and NaI, in $CH_2Cl_2$ and acetonitrile for about eight hours (see, e.g., Bhatt et al. (December 1982) *Synthesis* 12:1048-1050); and (12) in the presence of $NaBH_4$ and $I_2$ in THF at 0° C. (see, e.g., Thomas et al. (1997) *Tetrahedron Lett.* 38:4721). Each of the references cited is hereby incorporated by reference in its entirety.

4.17.2 Method for Making Compounds of Formula (41): Allyl Haloformate

In another embodiment, the present disclosure provides a method for making a compound of formula (41)

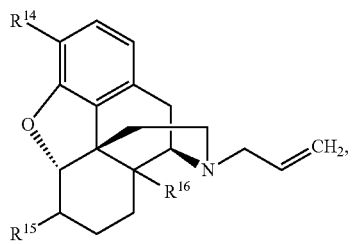

in which a compound of formula (45)

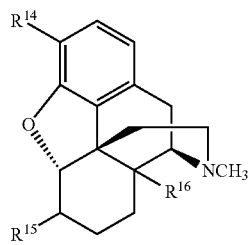

is contacted with a compound of formula (48)

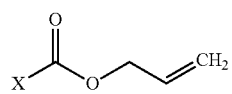

in a solvent comprising a base to provide a compound of formula (95)

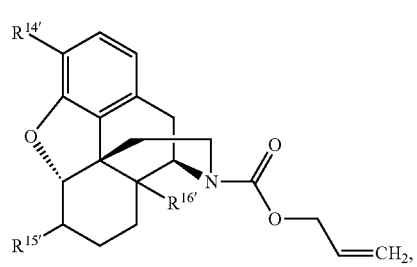

which can be decarboxylated in the transition metal-catalyzed reaction described in Section 4.3.1 to provide a compound of formula (41), where $R^{14}$, $R^{14'}$, $R^{15}$, $R^{15'}$, $R^{16}$, $R^{16'}$, and X are defined as above. As discussed above, for a carbonate-containing group present at $R^{14'}$, $R^{15'}$, and/or $R^{16'}$, formed from an $R^{14}$, $R^{15}$, and/or $R^{16}$ —OH group, respectively, that carbonate-containing group can be converted back to the —OH group.

In certain embodiments, the base is selected from the group consisting of $Na_2CO_3$, $NaHCO_3$, $KHCO_3$, $K_2CO_3$, $Cs_2CO_3$, NaOH, KOH, LiOH, and combinations of two or more thereof.

In certain embodiments, solvent is selected from the group consisting of $CHCl_3$, $CH_2Cl_2$, 1,2-dichloroethane, toluene, THF, ethyl acetate, acetone, tert-amyl alcohol, tert-butyl alcohol, 3-methyl-3-pentanol, 2,3-dimethyl-3-pentanol, 3-ethyl pentanol, 2-methyl-2-hexanol, acetonitrile, benzene, carbon tetrachloride, chlorobenzene, 1,2-dichlorobenzene, DMF, trifluorotoluene, 1,4-dioxane, 1,2-dimethoxyethane, xylene, and combinations of two or more thereof.

In particular embodiments, the solvent is selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a specific embodiment the solvent is tert-amyl alcohol.

In certain embodiments, the iodide salt is present in a sub-stoichiometric amount. In certain embodiments, the iodide salt is present in a catalytic amount. In another embodiment, the reaction is carried out in the presence of a catalytic amount of an iodide salt which can be selected from, e.g., NaI, KI, LH, CsI, RuI, $MgI_2$, $CaI_2$, $NH_4I$, tetrabutylammonium iodide, and combinations of two or more thereof. In certain embodiments, the iodide salt is NaI.

4.17.3 Method for Making Compounds of Formula (41): β-Carbon Elimination of a Leaving Group In another embodiment, the present disclosure provides a method for making a compound of formula (41), in which a compound of formula (45)

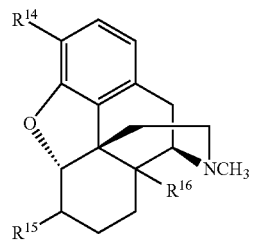

is contacted with a compound of formula (46)

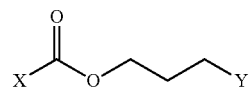

to provide a compound of formula (47)

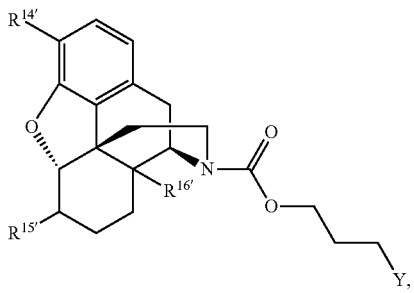

where $R^{14}$, $R^{14'}$, $R^{15}$, $R^{15'}$, $R^{16}$, $R^{16'}$, X, and Y are defined as above. In certain embodiments, the leaving group Y is selected from —Cl, —Br, —I, —OS(O)$_2$C$_4$F$_9$, —OS(O)$_2$CF$_3$, —OS(O)$_2$F, -para-toluene sulfonate, and —OS(O)$_2$CH$_3$. In a specific embodiment, Y is —Cl.

In certain embodiments, the compound of formula (47) is converted to a compound of formula (42) under conditions and/or in the presence of a reagent that promotes elimination of the leaving group, Y. In one aspect of this embodiment, elimination of the leaving group Y is promoted by heat. In another aspect, elimination of the leaving group Y is promoted by exposure to light of an appropriate wavelength. In a further aspect, elimination of the leaving group Y is promoted by including a reagent that is a base. Where the reagent is a base, it can, for example, be selected from the group consisting of NaOH, KOH, tert-BuONa, tert-BuOK, lithium di-iso-propylamide, sodium hydride, tert-butyl lithium, LiAlH$_4$, AlCl$_3$, triethylamine, sodium ethoxide, LiN(Et)$_2$, KOAc, and combinations of two or more thereof.

The compound of formula (42) can be decarboxylated in the transition metal-catalyzed reaction described in Section 4.3.1 to provide a compound of formula (41). In certain embodiments, the base is selected from the group consisting of NaOH, KOH, tert-BuONa, tert-BuOK, lithium di-iso-propylamide, sodium hydride, tert-butyl lithium, LiAlH$_4$, AlCl$_3$, triethylamine, sodium ethoxide, LiN(Et)$_2$, KOAc, and combinations of two or more thereof.

4.17.4 Method for Making Compounds of Formula (41): 3-Carbamate Hydrolysis

In another embodiment, the present disclosure provides a method for making a compound of formula (41) comprising the step of contacting a compound of formula (49)

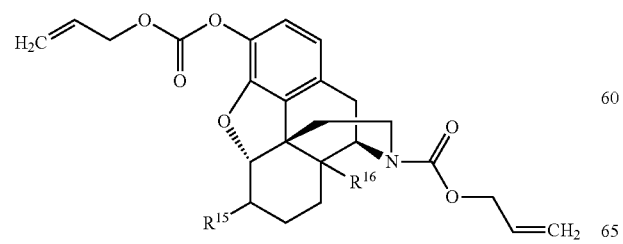

with base to provide a compound of formula (50)

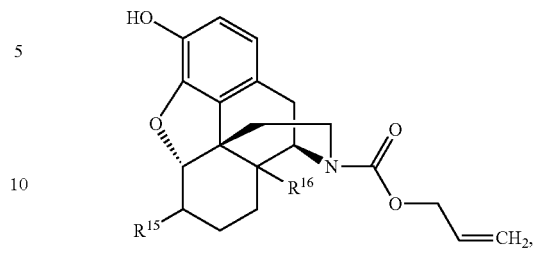

which is a compound of formula (42) in which $R^{14}$ is —OH. In a particular embodiment, $R^{15}$ is =O and $R^{16}$ is —OH.

4.17.5 Method for Making Compounds of Formula (41): Carbamate Exchange

In a further embodiment, the present disclosure also provides a method for making compounds of formula (41), which comprises contacting a compound of formula (45)

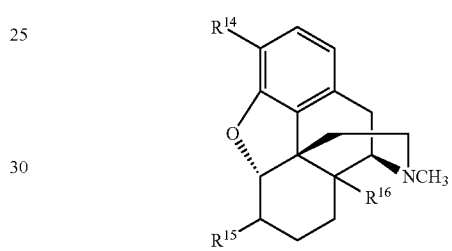

with a compound of formula (10)

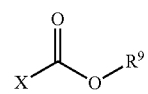

to provide a compound of formula (60)

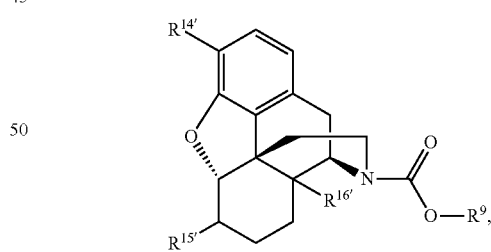

wherein $R^{14}$, $R^{14'}$, $R^{15}$, $R^{15'}$, $R^{16}$, $R^{16'}$, and X are defined as above.

The compound of formula (60) is contacted with an alkoxide derivative compound of formula (61)

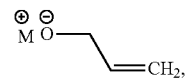

to provide the compound of formula (95)

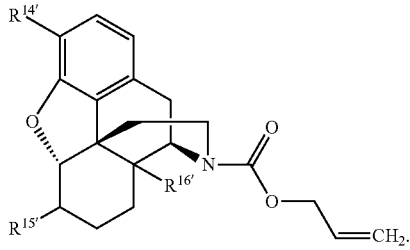

In this embodiment, $R^9$ is selected from phenyl and 4-nitrophenyl; $R^{14'}$, $R^{15'}$, and $R^{16'}$ are defined as above and M is selected from the group consisting of Na, K, and Li. The compound of formula (95) can be converted to the compound of formula (42)

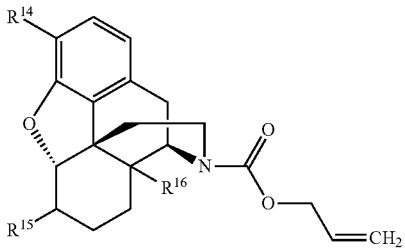

by basic hydrolysis. The compound of formula (42) can be decarboxylated in a transition metal-catalyzed reaction as described in Section 4.3.1 above, to provide a compound of formula (41).

Formation of the alkoxide derivative compound of formula (61) and conditions for the reaction of the alkoxide derivative compound of formula (61) with the compound of formula (60) to provide the compound of formula (42) can be carried out according to the methods disclosed by Villani et al. (1986) *Arzneim-Forsch./Drug Res.* 36(II), No. 9:1311-1314, which is hereby incorporated by reference in its entirety. Accordingly, in one embodiment, the alkoxide derivative is NaO—$CH_2CH$=$CH_2$ and it is prepared by reacting sodium with a 15-30 fold molar excess of HO—$CH_2CH$=$CH_2$ to provide an alkoxide solution which is contacted with a solution of a compound of formula (60), and the mixture is heated at 100° C. for four hours and then allowed to stand at a temperature of about 20° C. for about 16 hours, to provide as the desired product a compound of formula (42).

4.18 Method for Making Compounds of Formula (41): β-Carbon Elimination of a Leaving Group In another embodiment, the present disclosure provides a method for making compounds of formula (41), in which a compound of formula (47)

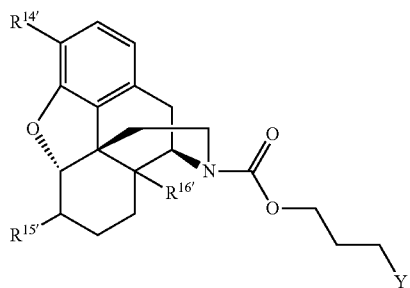

is contacted with a transition metal catalyst in a solvent to provide the compound of formula (41), where $R^{14}$, $R^{14'}$, $R^{15}$, $R^{15'}R^{16}$, $R^{16'}$, and Y are defined as above. The leaving group Y can be selected from —Cl, —Br, —I, —$OS(O)_2C_4F_9$, —$OS(O)_2CF_3$, —$OS(O)_2F$, -para-toluene sulfonate, and —$OS(O)_2CH_3$. In a specific embodiment, Y is —Cl. As discussed above, for a carbonate-containing group present at $R^{14'}$, $R^{15'}$, and/or $R^{16'}$, formed from an $R^{14}$, $R^{15}$, and/or $R^{16}$ —OH group, respectively, that carbonate-containing group can be converted back to the —OH group before the addition of the transition metal catalyst.

The oxygen protecting group, $R^{17}$, can be selected from the group consisting of consisting tert-butyl-diphenylsilyl, tert-butyl-dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, para-methoxybenzyl, methylthiomethyl, pivaloyl, methyl, ethoxyethyl, triphenylmethyl, —$C(O)(C_1-C_4)$ alkyl, —$C(O)OR^{24}$, and —$(C_1-C_6)$ alkyl, each alkyl being unsubstituted or substituted with 1, 2, 3, 4, or 5 independently-selected $R^{25}$ groups; $R^{24}$ is —$(C_1-C_6)$ alkyl, —$(C_2-C_6)$ alkenyl, or —$(C_2-C_6)$ alkynyl, each alkyl, alkenyl, and alkynyl being unsubstituted or substituted with 1, 2, 3, 4, or 5 independently-selected $R^{25}$ groups; and each $R^{25}$ is independently selected from —OH, —Cl, —Br, —I, —$NH_2$, —CN, and phenyl.

In certain embodiments of this method, the transition metal catalyst is selected from the group consisting of $Pd(PPh_3)_4$, $Pd(Ph_2P(CH_2)_4PPh_2)_2$, $Ni(PPh_3)_4$, $Ni(Ph_2P(CH_2)_4PPh_2)_2$, ((pentamethylcyclopentadienyl)$RuCl)_4$, [Pd(DBA)$_2$]/PPh$_3$, [Pd(OAc)$_2$]/PPh$_3$, [Ni(COD)$_2$]/PPh$_3$, $NiCl_2$/PPh$_3$, $Ni[P(OEt)_3]_4$, [Mo(CO)$_6$-DPPE], $RhH(PPh_3)_4$-P(n-Bu)$_3$, and combinations of two or more thereof. In another embodiment, the transition metal catalyst comprises 1, 2, 3, or 4 phosphine moieties. In another embodiment, the transition metal catalyst is tetrakis(triphenylphosphine)palladium[0].

In particular embodiments of this method, $R^{14'}$ and $R^{16'}$ are each independently selected from —OH and —$OC(O)O(CH_2)_3Y$, and $R^{15}$ is =O.

Further embodiments of this method comprise
(a) reacting a compound of formula (45)

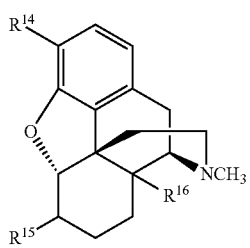

with a compound of formula (46)

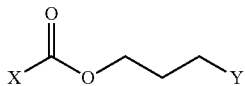

to provide a compound of formula (47)

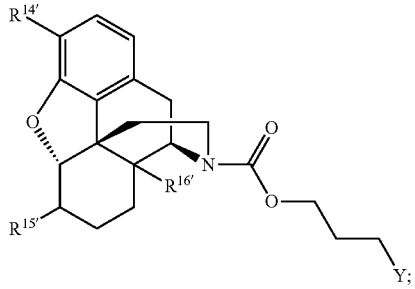

(b) optionally, converting the compound of formula (47) to the compound of formula (94)

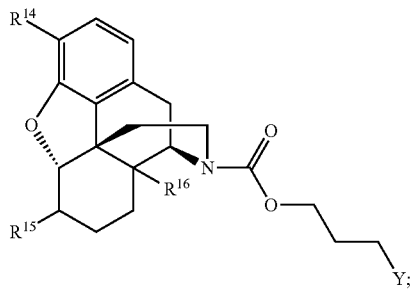

(c) converting the compound of formula (47) or the compound of formula

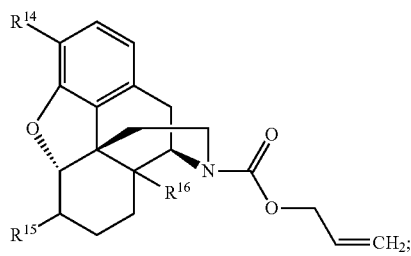

(94) to a compound of formula (42) and (d) converting the compound of formula (42) to the compound of formula (41), where $R^{14}$, $R^{14'}$, $R^{15}$, $R^{15'}$, $R^{16}$, $R^{16'}$, X, and Y are defined as above.

In alternative embodiments and as discussed above, for a carbonate-containing group present at $R^{14'}$, $R^{15'}$, and/or $R^{16'}$, formed from an $R^{14}$, $R^{15}$, and/or $R^{16}$ —OH group, respectively, that carbonate-containing group can be converted back to the —OH group after the decarboxylation step.

4.18.1 Method for Making Compounds of Formula (47)

In certain embodiments of this method, the compound of formula (47) is prepared by contacting a compound of formula (45)

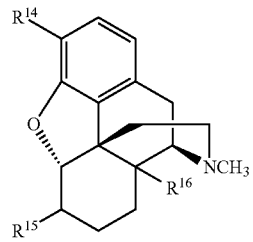

with a compound of formula (46)

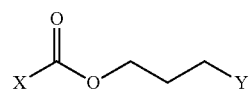

to provide the compound of formula (47)

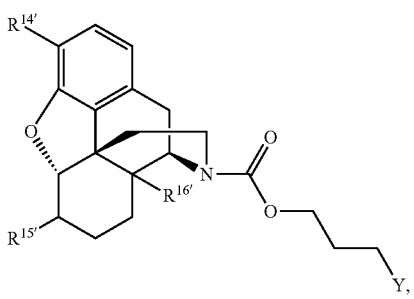

in which $R^{14}$, $R^{14'}$, $R^{15}$, $R^{15'}$, $R^{16}$, $R^{16'}$, X, and Y are defined as above.

In particular embodiments, the leaving group Y is selected from —Cl, —Br, —I, —OS(O)$_2$C$_4$F$_9$, —OS(O)$_2$CF$_3$, —OS(O)$_2$F, -para-toluene sulfonate, and —OS(O)$_2$CH$_3$. In a specific embodiment, Y is —Cl.

In other embodiments, $R^{17}$ is an oxygen protecting group selected from the group consisting of tert-butyl diphenylsilyl, tert-butyl dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, para-methoxybenzyl, methylthiomethyl, pivaloyl, methyl, ethoxyethyl, triphenylmethyl, —C(O)(C$_1$-C$_4$) alkyl, —C(O)OR$^{24}$, and —(C$_2$-C$_6$) alkyl, each alkyl being unsubstituted or substituted with 1, 2, 3, 4, or 5 independently-selected $R^{25}$ groups; $R^{24}$ is —(C$_1$-C$_6$) alkyl, —(C$_2$-C$_6$) alkenyl, or —C$_2$-C$_6$) alkynyl, each alkyl, alkenyl, and alkynyl being unsubstituted or substituted with 1, 2, 3, 4, or 5 independently-selected $R^{25}$ groups; and each $R^{25}$ is independently selected from —OH, —Cl, —Br, —I, —NH$_2$, —CN, and phenyl.

4.19 Method for Making Compounds of Formula (45)

In certain embodiments of the methods disclosed above, the compound of formula (45)

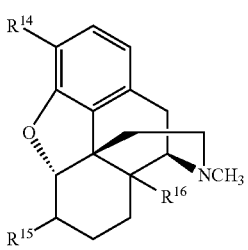

is a compound of formula (51)

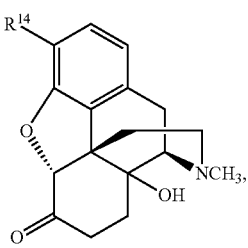

i.e., a compound of formula (45) in which $R^{15}$ is =O and $R^{16}$ is —OH.

In a further embodiment, the compound of formula (51), is prepared by oxidizing a compound of formula (52)

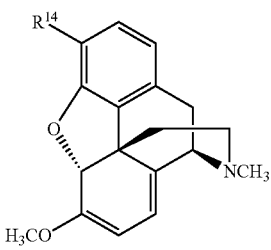

to provide a compound of formula (53)

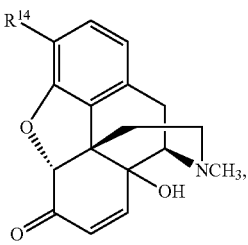

and hydrogenating the compound of formula (53) to provide the compound of formula (51).

In one aspect of this embodiment, $R^{14}$ is —OH. In another aspect of this embodiment, $R^{14}$ is —OCH$_3$.

In one embodiment, the compound of formula (52) is oxidized to the product of formula (53) with performic acid, which can be prepared in situ by mixing hydrogen peroxide and excess formic acid. The reaction is warmed to a temperature within the range of from about 20° C. to about 80° C., or within the range of from about 30° C. to about 70° C., or within the range of from about 40° C. to about 60° C., and maintained at that temperature for a time sufficient to allow the starting material to be consumed. In certain embodiments, the reaction is carried out at a temperature of about 50° C. for about two hours.

The oxidized product, a compound of formula (53), can be taken as the crude product of the oxidation reaction directly on to the next step (hydrogenation of the 7,8-double bond) without purification. In this embodiment, the crude compound of formula (53) is hydrogenated in the presence of a catalyst under a hydrogen atmosphere at a temperature within the range of from about 10° C. to about 75° C., or within the range of from about 25° C. to about 65° C., or within the range of from about 30° C. to about 55° C. In certain embodiments, the hydrogenation is carried out at a temperature within the range of from about 40° C. to about 45° C. The catalyst can be, e.g., a palladium or a platinum catalyst and can be dispersed on a solid support as, e.g., Pd/C or Pt/C. Once the reaction is deemed complete, the mixture is then cooled to a temperature within the range of from about 2° C. to about 10° C. and filtered to remove the catalyst. The pH of the filtrate is adjusted and the reaction mixture stirred to allow the resultant crude compound of formula (51) as the free base to form a precipitate that is filtered, washed, and dried.

4.20 Method for Making Compounds of Formula (54)

The present disclosure also provides methods for making compounds of formula (54)

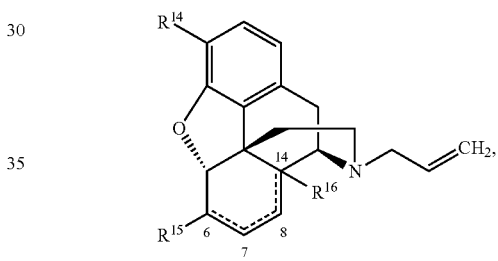

which comprise contacting a compound of formula (55)

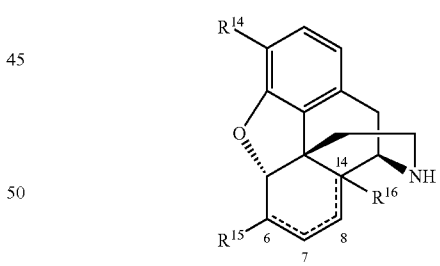

with a compound of formula (56)

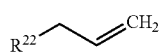

in a solvent comprising a base and a transition metal catalyst to provide the compound of formula (54).

In this embodiment, $R^{14}$ and $R^{16}$ are each independently selected from —OH, —H, and —OR$^{17}$; and the 6,7 ----- bond, the 7,8 ----- bond, and the 8,14 ----- bond are each independently a single bond or a double bond, with the provisos that (1) if the 6,7 ----- bond is a double bond, then the 7,8 ----- bond is a single bond, (2) if the 7,8 ----- bond is a double bond, then the 6,7 ----- and 8,14 ----- bonds are each a single bond, and (3) if the 8,14 ----- bond is a double bond, then the 7,8 ----- bond is a single bond and R[16] is not present.

In this embodiment, R[15] is selected from —OH, —H, —OR[17], =O, and =CH$_2$ with the proviso that if the 6,7 ----- bond is a double bond, then R[15] is selected from —OH, —H, and —OR[17]; and R[17] is an oxygen protecting group. In this embodiment, R[22] is selected from —N(CH$_3$)$_2$, —OC(O)CH$_3$, and —OC(O)X; and X is selected from —Cl, —Br, and —I. In another embodiment, R[22] is selected from —N(CH$_3$)$_2$ and —OC(O)CH$_3$. In another embodiment, R[22] is —OC(O)X.

In this embodiment, the transition metal catalyst is selected from the group consisting of Pd(PPh$_3$)$_4$, Pd(Ph$_2$P (CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd (OAc)$_2$]/PPh$_3$, [Ni(COD)$_2$]/PPh$_3$, NiCl$_2$/PPh$_3$, Ni[P (OEt)$_3$]$_4$, [Mo(CO)$_6$-DPPE], RhH(PPh$_3$)$_4$-P(n-Bu)$_3$, and combinations of two or more thereof. In another embodiment, the transition metal catalyst comprises 1, 2, 3, or 4 phosphine moieties. In another embodiment, the transition metal catalyst is tetrakis(triphenylphosphine)palladium[0].

In this embodiment, the base is selected from the group consisting of Na$_2$CO$_3$, NaHCO$_3$, KHCO$_3$, K$_2$CO$_3$, Cs$_2$CO$_3$, and combinations of two or more thereof.

In this embodiment, R[17] is an oxygen protecting group selected from the group consisting of tert-butyl-diphenylsilyl, tert-butyl-dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, para-methoxybenzyl, methylthiomethyl, pivaloyl, methyl, ethoxyethyl, triphenylmethyl, —C(O)(C$_1$-C$_4$) alkyl, —C(O)OR[24], and —(C$_2$-C$_6$) alkyl, each alkyl being unsubstituted or substituted with 1, 2, 3, 4, or 5 independently-selected R[25] groups; R[24] is —(C$_1$-C$_6$) alkyl, —(C$_2$-C$_6$) alkenyl, or —(C$_2$-C$_6$) alkynyl, each alkyl, alkenyl, and alkynyl being unsubstituted or substituted with 1, 2, 3, 4, or 5 independently-selected R[25] groups; and each R[25] is independently selected from —OH, —Cl, —Br, —I, —NH$_2$, —CN, and phenyl.

In one embodiment, the 6,7 ----- bond, the 7,8 ----- bond, and the 8,14 ----- bond is each a single bond. In another embodiment, the 7,8 ----- bond is a double bond; and the 6,7 ----- and 8,14 ----- bonds are each a single bond. In another embodiment, the 6,7 ----- and 8,14 ----- bonds are each a double bond; the 7,8 ----- bond is a single bond; R[16] is not present; and R[15] is selected from —OH, —H, and —OR[17].

In another embodiment, the 6,7 ----- bond, the 7,8 ----- bond, and the 8,14 ----- bond is each a single ----- bond; and R[15] is selected from —OH, —OR[17], and =O. In another embodiment, the 7,8 ----- bond is a double ----- bond; and the 6,7 ----- and 8,14 ----- bonds are each a single ----- bond; R[15] is selected from —OH, —OR[17], and =O; and R[14] and R[16] are each independently selected from —OH and —H. In another embodiment, the 6,7 ----- and 8,14 ----- bonds are each a double ----- bond, the 7,8 ----- bond is a single bond, R[16] is not present, and R[15] is —OR[17].

In one embodiment of this method, the 6,7 ----- and 8,14 ----- bonds are each a double bond and R[15] is —OCH$_3$.

In one embodiment, R[22] is selected from —N(CH$_3$)$_2$, and —OC(O)CH$_3$. In another embodiment R[22] is —OC(O)X; and X is —Br, —Cl, or —I.

In one aspect of this embodiment, R[14] is —OH. In another aspect of this embodiment, R[14] is —OCH$_3$.

4.21 Method for Making Compounds of Formula (57)

The present disclosure also provides a method for making compounds of formula (57)

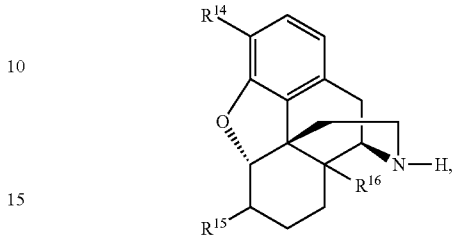

which comprises contacting a compound of formula (42)

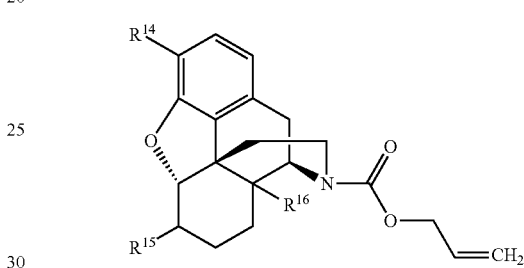

with a transition metal catalyst in the presence of an allyl scavenger to provide the compound of formula (57). In this embodiment, R[14] and R[16] are each independently selected from —OH, —H, and —OR[17]; R[15] is selected from —OH, —H, —OR[17], =O, and =CH$_2$; and R[17] is an oxygen protecting group. The allyl scavenger is selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof.

In another embodiment, the compound of formula (57) is prepared by contacting a compound of formula (41)

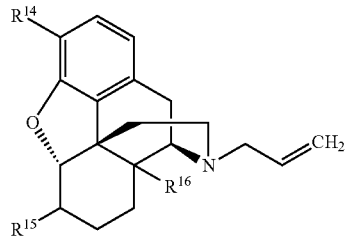

with a transition metal catalyst in the presence of an allyl scavenger to provide the compound of formula (57), where R[14] and R[16] are each independently selected from —OH and —H; R[15] is selected from —OH, —H, —OR[17], =O, and =CH$_2$; and R[17] is an oxygen protecting group. The allyl scavenger can be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof.

In one embodiment, the compound of formula (41) is taken up in dichloromethane and N,N-dimethyl barbituric acid (0.5 to 1.0 equivalents) and tetrakis(triphenylphosphine)palladium[0] (0.05 equivalents), and the reaction mixture is stirred at about 20° C. and then at about 40° C. for 16 hours. Once the reaction is deemed complete, the mixture is cooled to a temperature of about 20° C. and the solids filtered under reduced pressure. The solids can be washed with dichloromethane and then with water before being taken up in a 10:1 mixture of water:concentrated sulfuric acid at 40° C. The warmed aqueous solution is washed with dichloromethane and then basified to a pH of 9.05 with 28% ammonium hydroxide. The resulting solids are filtered and dried under reduced pressure at 100° C. for 20 hours to yield the product, a compound of formula (57).

4.22 Method for Making Compounds of Formula (58)

The present disclosure also provides a method for making compounds of formula (58)

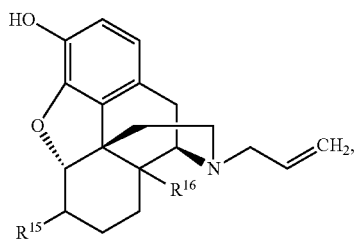

in which a compound of formula (59)

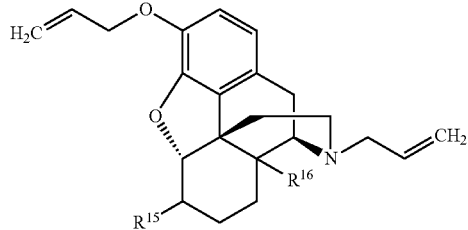

is contacted with a transition metal catalyst in a solvent in the presence of an allyl scavenging reagent ("allyl scavenger") to provide the compound of formula (58), where $R^{16}$ is selected from —OH, —H, and —OC(O)CH$_2$CH=CH$_2$; $R^{15}$ is selected from —OH, —H, —OR$^{17}$, =O, and =CH$_2$; and $R^{17}$ is an oxygen protecting group.

In one embodiment, the allyl scavenger can be selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof. In another embodiment, the allyl scavenger is compound (146)

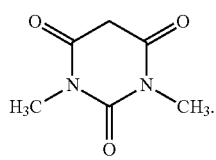

4.23 Method for Making Compounds of Formula (42)

In a further embodiment, the present disclosure also provides a method for making compounds of formula (42), which comprises contacting a compound of formula (45)

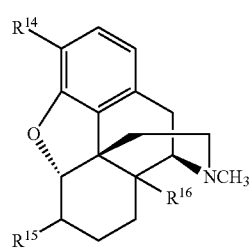

with a compound of formula (10)

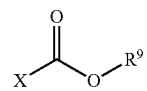

to provide a compound of formula (60)

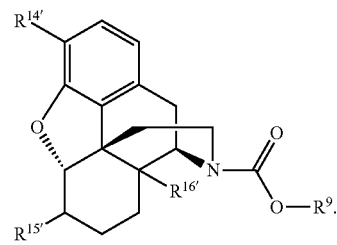

The compound of formula (60) is contacted with an alkoxide derivative compound of formula (61)

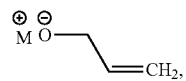

to provide a compound of formula (95). In this embodiment, $R^9$ is selected from phenyl and 4-nitro-phenyl; $R^{14}$, $R^{14'}$, $R^{15}$, $R^{15'}$, $R^{16}$, $R^{16'}$, X, and M are defined as above. The compound of formula (60) can then be converted to the compound of formula (42) by converting any carbonate groups present to —OH groups.

In one embodiment, the alkoxide derivative is NaO—CH$_2$CH=CH$_2$ which is prepared by reacting sodium with a 15-30 fold molar excess of HO—CH$_2$CH=CH$_2$ to provide an alkoxide solution which is contacted with a solution of a compound of formula (60), and the mixture is heated at 100° C. for four hours and then allowed to stand at a temperature of about 20° C. for about 16 hours to provide the compound of formula (42). The compound of formula (42) can be then be decarboxylated in a transition metal-catalyzed reaction as described in Section 4.3.1 above to provide a compound of formula (41).

4.24 Method for Making Compounds of Formula (62)

The present disclosure further provides a method for making compounds of formula (62)

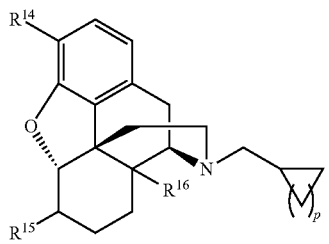

comprising (a) contacting a compound of formula (45)

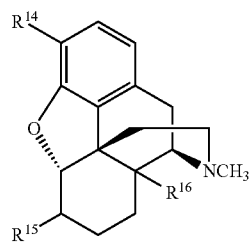

with a compound of formula (63)

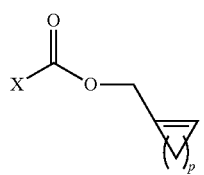

in a solvent comprising a base to provide a compound of formula (64)

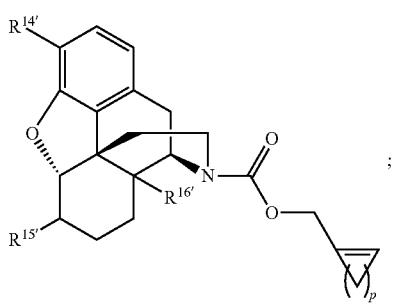

(b) optionally, converting any carbonate group at $R^{14'}$, $R^{15'}$, or $R^{16'}$ to an —OH group to provide a compound of formula (96)

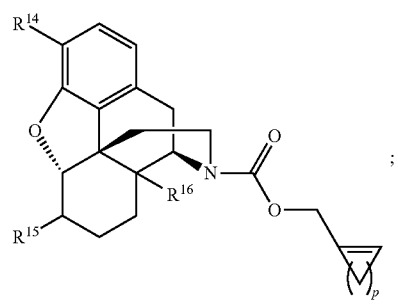

(c) contacting the compound of formula (64) or the compound of formula (96) with a transition metal catalyst to provide a compound of formula (65)

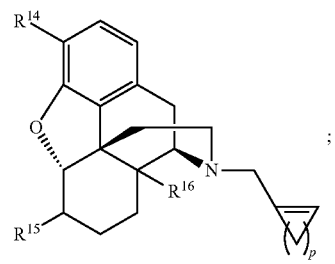

and (d) hydrogenating the compound of formula (65) to provide a compound of formula (62). In this embodiment, $R^{14}$, $R^{14'}$, $R^{15}$, $R^{15'}$, $R^{16}$, $R^{16'}$, and X are defined as above. The compound of formula (65) can be hydrogenated, e.g., by contact with a hydrogen atmosphere in the presence of an appropriate catalyst, e.g., Pd/C or Pt/C.

In one aspect of this embodiment, p is 1. In another aspect of this embodiment, p is 2.

In certain embodiments, the compound of formula (63) is prepared in two steps. In the first, an alkene containing-1-methanol derivative of the following formula

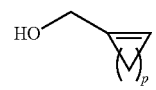

is synthesized from a tribromocyclic-2-methanol compound in a manner analogous that described for use of the corresponding 1,1,2-tribromocyclopropane-2-methanol of Dulayymi et al. (1996) *Tetrahedron* 52(10):3409-3424, which is hereby incorporated by reference in its entirety. The alcohol is then reacted with phosgene to provide the corresponding chloroformate reagent compound of formula (73)

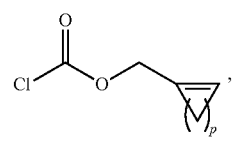

i.e., the compound of formula (63) where X is Cl.

4.25 Method for Making Compounds of Formula (66)

The present disclosure also provides a method for making a compound of formula (66)

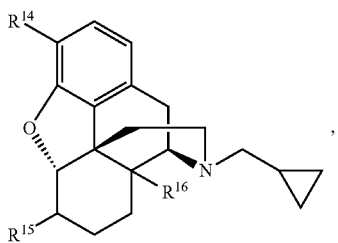

which comprises (a) contacting a compound of formula (45)

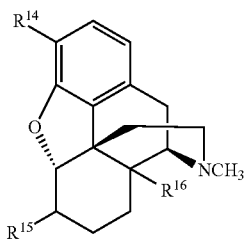

with a compound of formula (67)

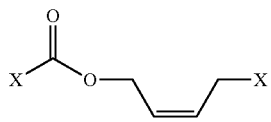

to provide a compound of formula (68)

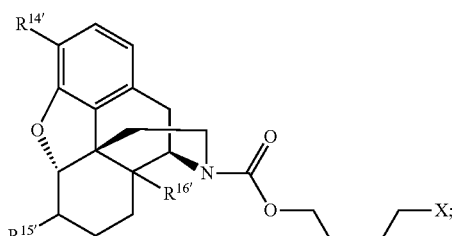

(b) optionally, converting the carbonate groups present at $R^{14'}$, $R^{15'}$, and $R^{16'}$ to —OH groups to provide the compound of formula (97)

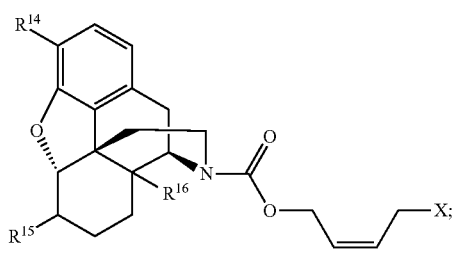

(c) contacting the compound of formula (68) or the compound of formula (97) with a transition metal catalyst to provide a compound of formula (69)

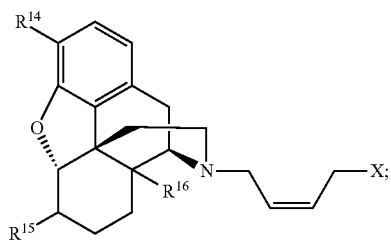

and (d) contacting the compound of formula (69) with a zinc-containing reagent, e.g., zinc[0], to provide the compound of formula (66). In these embodiments, $R^{14}$, $R^{14'}$, $R^{15}$, $R^{15'}$, $R^{16}$, $R^{16'}$, and X, are defined as above. In certain embodiments, the compound of formula (68) is one in which X is —I.

In alternative embodiments, any carbonate groups present at $R^{14'}$, $R^{15'}$, and/or $R^{16'}$ can be converted to —OH groups after the decarboxylation step.

In certain embodiments, the contacting is carried out in the presence of an iodide salt. The iodide salt can be selected from, e.g., NaI, KI, LiI, CsI, RuI, $MgI_2$, $CaI_2$, $NH_4I$, tetrabutylammonium iodide, and combinations of two or more thereof. In certain embodiments, the iodide salt is NaI. In certain embodiments, the iodide salt is present in a sub-stoichiometric amount. In certain embodiments, the iodide salt is present in a catalytic amount.

In certain embodiments, the compound of formula (67) has the following chemical structure

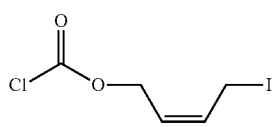

(compound (142)) and is prepared by reacting an alcohol of the following formula

(compound (143)) with phosgene to provide the depicted chloroformate: (Z)-4-iodobut-2-enyl carbonochloridate. The alcohol (Z)-4-iodobut-2-en-1-ol can be prepared as described by Balas et al. (2009) *J. Med. Chem.* 52:1005-1017, which is hereby incorporated by reference in its entirety.

4.26 Processes for the Preparation of Compounds of Formulae (74), (75), (88), and (89)

In other illustrative embodiments, the present disclosure provides methods for the synthesis of compounds of formula (74) and formula (75). More specifically, the present disclosure provides a method for making a compound of formula (74)

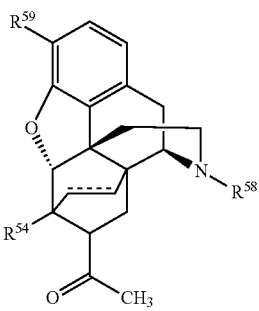

comprising (a) contacting a compound of formula (76)

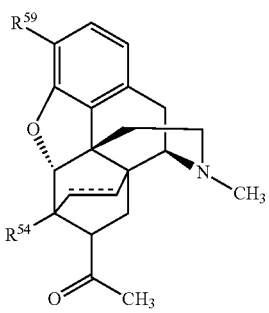

with a compound of formula (93)

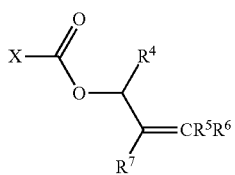

in a solvent to provide a compound of formula (77)

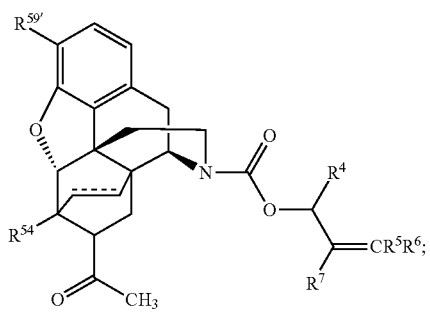

(b) optionally, converting a carbonate group at $R^{59'}$ to an —OH group to provide a compound of formula (99)

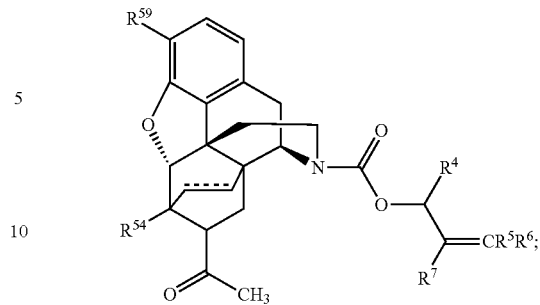

(c) converting the compound of formula (77) or the compound of formula (99) to a compound of formula (78)

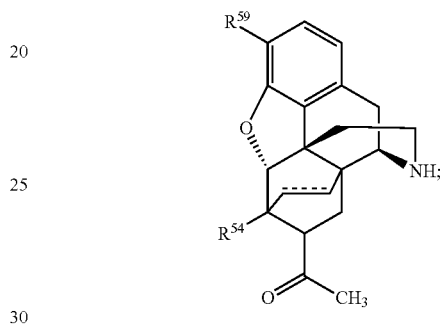

and (d) contacting the compound of formula (78) with a compound of formula (79) X—$R^{58}$ to provide the compound of formula (74), where the ----- bond is a single bond or a double bond. In certain embodiments, the solvent comprises a tertiary alcohol while, in other embodiments, the solvent consists essentially of a tertiary alcohol.

In this embodiment, $R^{59}$ is selected from —OH, —H, and —$OR^{17}$; $R^{54}$ is selected from —H, —$CH_3$, —OH, and —$OR^{17}$; $R^{17}$ is an oxygen protecting group; and $R^{58}$ is selected from allyl, methyl cyclopropyl, methyl cyclobutyl, and propargyl.

As used throughout herein, it is to be understood that $R^{59'}$ includes not only $R^{59}$ but also, when an $R^{59}$ group is present as an —OH group, the reaction product of a compound of formula (48) or its equivalent, e.g., an "allyl haloformate equivalent," with that —OH group to form a group comprising a carbonate. Thus, $R^{59'}$ groups include, in addition to the respective $R^{59}$ groups, such carbonate-containing reaction products. Even further, certain reaction pathways described herein convert the carbonate portion of the carbonate-containing reaction product into an ether group. Thus, $R^{59'}$ further includes such ether-containing reaction products.

It is also to be understood that when $R^{59}$ is selected to be a particular moiety that is not an —OH group, then $R^{59'}$ is also that particular $R^{59}$ moiety.

In embodiments where an $R^{59'}$ group is a carbonate-containing group formed from an —OH group, that carbonate-containing group can be converted back to the —OH group. Conversion of the carbonate-containing group to the —OH group can be carried out in the presence of a suitable base. Alternatively, when an $R^{59'}$ group is an allyl carbonate, that allyl carbonate can first be converted into an —O-allyl group through a transition metal catalyzed decarboxylation reaction, in accordance with the present disclosure. Thereafter, the —O-allyl group can be converted into an —OH group in the presence of a suitable allyl scavenger, as described herein.

$R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

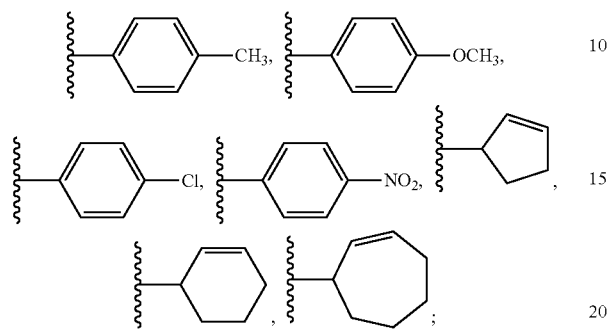

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group. Each X is independently selected from —Cl, —Br, and —I. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In certain embodiments, the tertiary alcohol is selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In a particular embodiment, the tertiary alcohol is tert-amyl alcohol.

In certain embodiments, conversion of the compound of formula (77) to the compound of formula (78) comprises contacting the compound of formula (77) with a transition metal catalyst in the presence of an allyl scavenger to provide the compound of formula (78). Suitable reaction conditions for this conversion are analogous to or readily adapted from those of Example 7 and correspond to the reactions depicted in Schemes 24 through 28.

In certain embodiments, the allyl scavenger is selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof.

The present disclosure also provides a method for making a compound of formula (75)

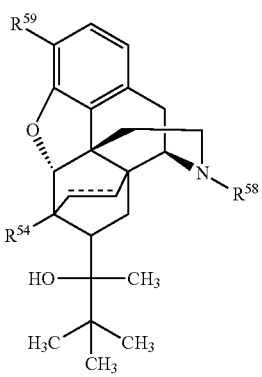

comprising
(a) contacting a compound of formula (80)

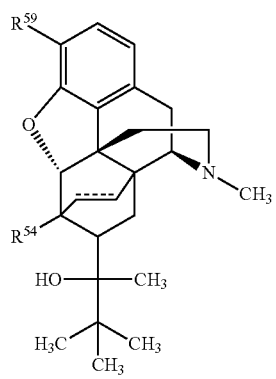

with a compound of formula (93)

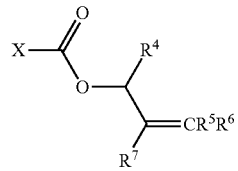

in a solvent to provide a compound of formula (81)

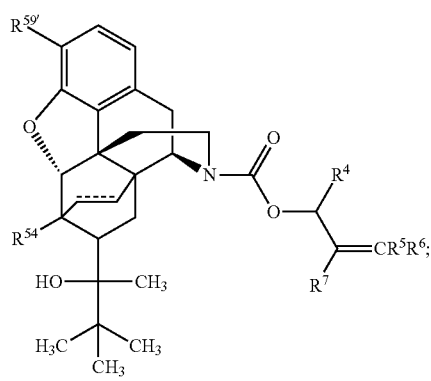

(b) optionally, converting a carbonate group at $R^{59'}$ to an —OH group to provide a compound of formula (100)

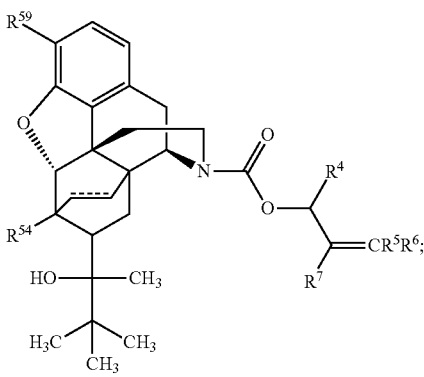

(c) converting the compound of formula (81) or the compound of formula (100) to a compound of formula (82)

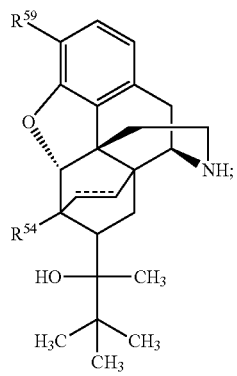

and (d) contacting the compound of formula (82) with a compound of formula (79) X—$R^{58}$ to provide the compound of formula (75), where the ----- bond is a single bond or a double bond. In certain embodiments, the solvent comprises a tertiary alcohol while, in other embodiments, the solvent consists essentially of a tertiary alcohol. $R^{59}$, $R^{59'}$, $R^4$, $R^5$, $R^6$, $R^7$, and X are defined as above.

In certain embodiments, conversion of the compound of formula (81) or the compound of formula (100) to the compound of formula (82) comprises contacting the compound of formula (81) or the compound of formula (100) with a transition metal catalyst in the presence of an allyl scavenger to provide the compound of formula (82). Suitable reaction conditions for this conversion are analogous to or readily adapted from those of Example 7 and correspond to the reactions depicted in Schemes 24 through 28.

In certain embodiments, the allyl scavenger is selected from the group consisting of sodium 2-ethylhexonate, morpholine, dimedone, 4-methylbenzensulfinic acid, sodium hydroxymethyl sulfinate, benzenesulfinic acid, sodium toluene sulfinate, sodium 2-thiophene sulfinate, tetrabutylammonium toluene sulfinate, N,N-dimethyl barbituric acid, sodium 4-chloro-3-nitrobenzene sulfinate, formic acid, diethyl amine, methanol, ethanol, and combinations of two or more thereof.

The tertiary alcohol can be selected from the group consisting of tert-amyl alcohol, tert-butyl alcohol, 3-methyl-3-pentanol, 2,3-dimethyl-3-pentanol, 3-ethyl pentanol, 2-methyl-2-hexanol, and combinations of two or more thereof. In certain embodiments, the tertiary alcohol is tert-amyl alcohol.

In certain embodiments of these methods for making compounds of formula (74) and formula (75), $R^{58}$ is methyl cyclopropyl, the ----- bond is a single bond, $R^{59}$ is —OH, and $R^{54}$ is —$OCH_3$.

In certain embodiments of these methods for making compounds of formula (74) and formula (75), each oxygen protecting group, $R^{17}$, can be independently selected from the group consisting of tert-butyl-diphenylsilyl, tert-butyl-dimethylsilyl, trimethylsilyl, tri-iso-propylsilyl, tert-butyldimethylsilyloxymethyl, β-methoxyethoxymethyl, [bis-(4-methoxyphenyl)phenylmethyl)], methoxymethyl, para-methoxybenzyl, methylthiomethyl, pivaloyl, ethoxyethyl, triphenylmethyl, —$C(O)R^{56}$, —$C(O)OR^{57}$, —($C_1$-$C_6$) alkyl, —($C_2$-$C_6$) alkenyl, —($C_2$-$C_6$) alkynyl, aryl, and heteroaryl, each alkyl, alkynyl, alkenyl, aryl, and heteroaryl being unsubstituted or substituted with 1, 2, 3, 4, or 5 independently-selected $R^8$ groups. Each $R^{56}$ and each $R^{57}$ can be independently selected from —($C_1$-$C_6$) alkyl, —($C_2$-$C_6$) alkenyl, —($C_2$-$C_6$) alkynyl, aryl, and heteroaryl, each being unsubstituted or substituted with 1, 2, 3, 4, or 5 independently-selected $R^8$ groups.

$R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group. In certain embodiments, $R^{17}$ is selected from the group consisting of methyl, ethyl, iso-butyl, acetyl, benzyl, benzoyl, allyl, allyloxycarbonyl, phenyl, phenyloxycarbonyl, and alkyloxycarbonyl.

In certain embodiments of these methods for making compounds of formula (74) and formula (75), $R^{59'}$ is —$OR^{17}$ and $R^{17}$ is —$C(O)OR^{57}$. In particular embodiments of these methods, $R^{57}$ is iso-butyl. In another particular embodiment, $R^{57}$ is ethyl. In a specific embodiment, $R^{57}$ is allyl. In another embodiment, $R^{54}$ is —$OCH_3$.

In certain embodiments of these methods for making compounds of formula (74) and formula (75), step (a) in each instance can be carried out in the presence of an iodide salt. In certain embodiments, the iodide salt is present in a sub-stoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof. In particular embodiments, the iodide salt is NaI.

In certain embodiments of these methods for making compounds of formula (74) and formula (75), step (c) in each instance can be carried out in the presence of an iodide salt. In certain embodiments, the iodide salt is present in a sub-stoichiometric amount. In certain embodiments, the iodide salt is present in a catalytic amount. The iodide salt can be selected from the group consisting of NaI, KI, LiI, CsI, RuI, $MgI_2$, $CaI_2$, $NH_4I$, tetrabutylammonium iodide, and combinations of two or more thereof. In particular embodiments, the iodide salt is NaI.

In another embodiment, the compound of formula (77)

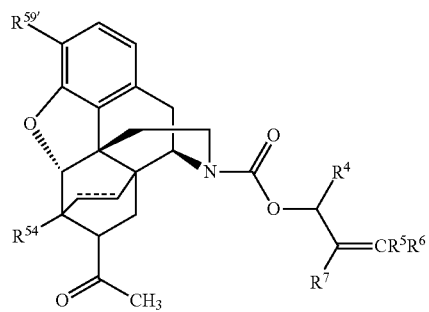

is converted to a compound of formula (83)

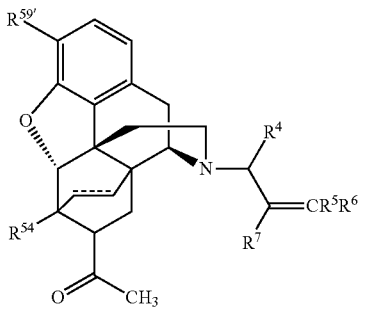

by contacting the compound of formula (77) with a transition metal catalyst. This decarboxylation reaction corresponds to that depicted in Step 2 of Scheme 1, as well as the reaction depicted in Schemes 3, 7, and 9 above, and suitable conditions for this reaction are analogous to or readily adapted from those of Example 4 and Example 5.

In another embodiment, the compound of formula (81)

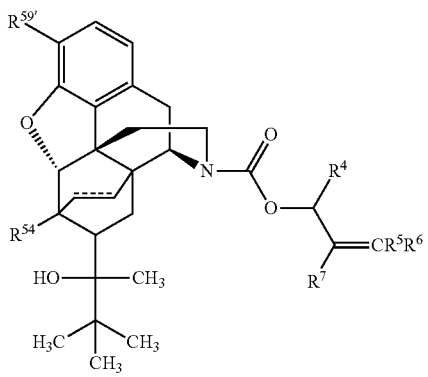

is converted to a compound of formula (84)

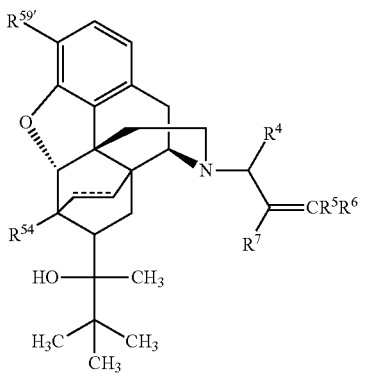

by contacting the compound of formula (81) with a transition metal catalyst. This decarboxylation reaction corresponds to that depicted in Step 2 of Scheme 1, as well as the reaction depicted in Schemes 3, 7, and 9 above, and suitable conditions for this reaction are analogous to or readily adapted from those of Example 4 and Example 5.

In another embodiment, the present disclosure provides a method for making a compound of formula (88)

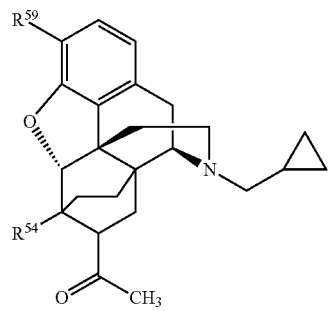

comprising (a) contacting a compound of formula (76)

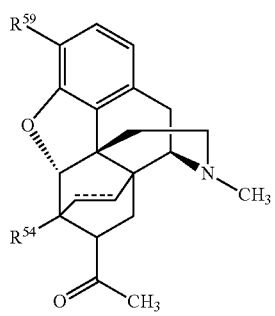

with a compound of formula (85)

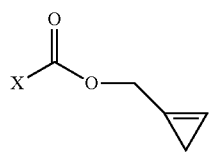

in a solvent to provide a compound of formula (86)

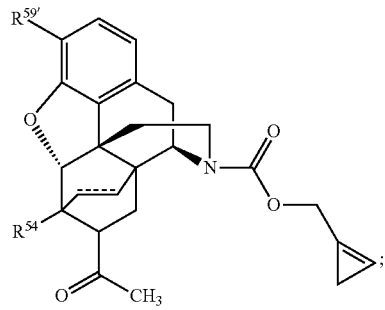

(b) optionally, converting a carbonate group at $R^{59'}$ to an —OH group to provide a compound of formula (100)

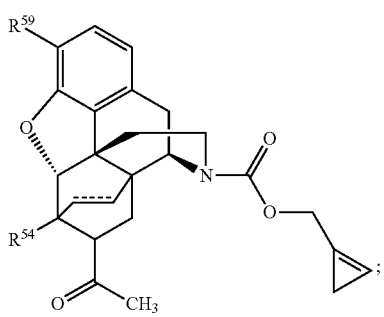

(c) decarboxylating the compound of formula (86) or the compound of formula (100) to provide a compound of formula (87)

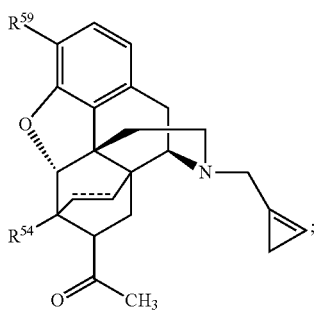

(d) hydrogenating the compound of formula (87) to provide the compound of formula (88).

In a further embodiment, the present disclosure provides a method for making a compound of formula (89)

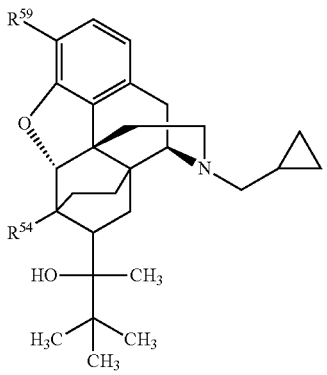

comprising
(a) contacting a compound of formula (80)

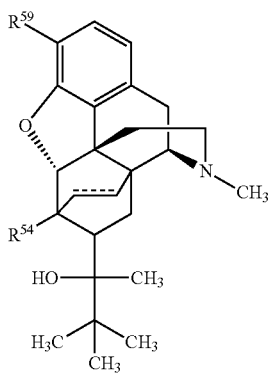

with a compound of formula (85)

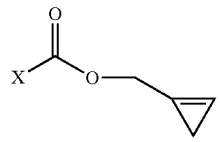

in a solvent to provide a compound of formula (90)

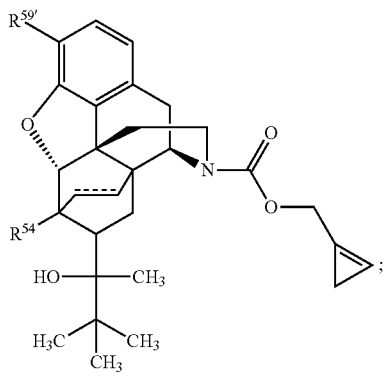

(b) optionally, converting a carbonate group at $R^{59'}$ to an —OH group to provide a compound of formula (101)

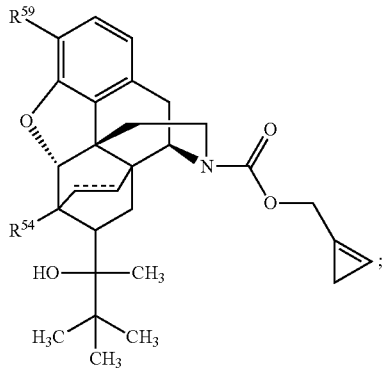

(c) decarboxylating the compound of formula (90) or a compound of formula (101) to provide a compound of formula (91)

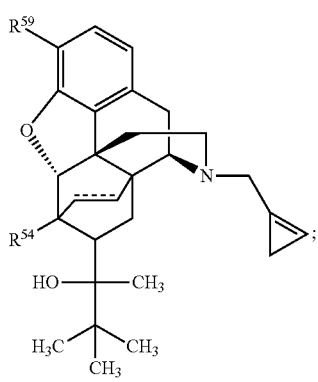

and
(d) hydrogenating the compound of formula (91) to provide the compound of formula (89).

The methods disclosed above for conversion of compounds of formula (76) to compounds of formula (88) (via intermediates of formula (86) and formula (87)) and for conversion of compounds of formula (80) to compounds of formula (89) (via intermediates of formula (90) and formula (91)) are analogous to Steps 3-5 of Scheme 16.

In another embodiment, the compounds of formula (88) are prepared by contacting a compound of formula (76) with a compound selected from the group consisting of compound (119), a compound of formula (19), a compound of formula (29), and a compound of formula (67), to provide a carbamate intermediate that can be decarboxylated and then hydrogenated to provide the compound of formula (88), using methods and reagents disclosed herein.

In a further embodiment, the compounds of formula (89) are prepared by contacting a compound of formula (80) with a compound selected from the group consisting of compound (119), a compound of formula (19), a compound of formula (29), and a compound of formula (67), to provide a carbamate intermediate that can be decarboxylated and then hydrogenated to provide the compound of formula (89), using methods and reagents disclosed herein.

4.27 Processes Comprising Transition Metal-catalyzed Decarboxylation of Compounds Derived from Thebaine, Morphine, and Codeine The present disclosure provides illustrative processes comprising transition metal-catalyzed reactions that are useful for the conversion of oripavine to naloxone (Schemes 6 and 10), to noroxymorphone (Schemes 6 and 10 combined with Scheme 14), and to naltrexone (Scheme 16). In other embodiments, the reactions, processes, and reagents disclosed herein can also be used for the synthesis of clinically and commercially important derivatives of thebaine, morphine, and codeine. The following sections disclose the preparation of an illustrative compound, naltrexone, from morphine, codeine, and thebaine, using processes that incorporate N-allyl decarboxylation reactions disclosed herein. Known processes for the preparation of, e.g., buprenorphine, naloxone, nalorphine, nalmefene, nalbuphine, noroxymorphone, and noroxycodone from morphine, codeine, and thebaine, can be adapted in a similar manner to incorporate N-allyl decarboxylation reactions disclosed herein to provide improved methods for the production of those compounds.

4.27.1 Preparation of Naltrexone from Morphine

U.S. Pat. No. 5,952,495 provides two alternate methods that could be used for the preparation of naltrexone. In the first morphine is converted, in two steps, to 6-acetyl-3-benzylmorphine which is N-demethylated by reaction with either 1-chloroethyl chloroformate or cyanogen bromide followed by acid hydrolysis to 3-benzylnormorphine. Reaction of 3-benzylnormorphine with a benzyl halide provides 3,17-dibenzylnormorphine, which is oxidized to 3,17-dibenzylnormorphinone by Swern oxidation. The 3,17-dibenzylnormorphinone, in turn, is oxidized to 3,17-dibenzyl-14-hydroxynormorphinone by either (1) directly reacting with hydrogen peroxide in formic acid or (2) first converting to 3,17-dibenzylnormorphinone dienol acylate and then reacting the latter with hydrogen peroxide in formic acid or a peroxyacid. The oxidized product is then hydrogenated to produce noroxymorphone. Reaction of noroxymorphone with, e.g., cyclopropyl methyl bromide, would provide naltrexone. This process therefore includes either eight or nine steps depending on the route taken for introduction of the 14-hydroxyl group.

In the second approach, morphine is converted to 3-benzylnormorphine, which is reacted with cyclopropylmethyl halide to produce 3-benzyl-17-cyclopropylmethylnormorphine which, in turn, is oxidized to 3-benzyl-17-cyclopropylmethyl-normorphinone by Swern oxidation. This compound is oxidized to 3-benzyl-17-cyclopropylmethyl-14-hydroxynormorphinone by either (1) directly reacting with hydrogen peroxide in formic acid or (2) first converting to 3-benzyl-17-cyclopropylmethylnormorphinone dienol acylate and then reacting the latter with hydrogen peroxide in formic acid or a peroxyacid. The oxidized product, 3-benzyl-17-cyclopropylmethyl-14-hydroxynormorphinone, is hydrogenated to remove the benzyl group and reduce the 7,8-double bond simultaneously to provide naltrexone.

Both of the processes of U.S. Pat. No. 5,952,495 describing the preparation of naltrexone from morphine include either eight or nine steps depending on the route taken for introduction of the 14-hydroxyl group.

In contrast, naltrexone can be prepared from morphine in five or fewer steps according to methods disclosed herein, e.g., as depicted in Scheme 31.

Scheme 31

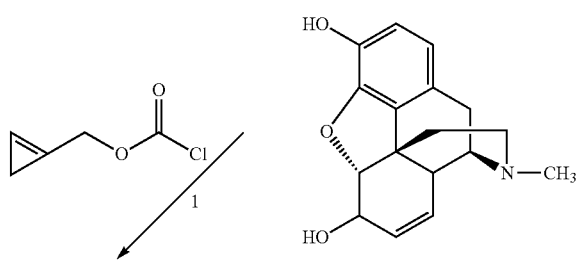

133 134

-continued

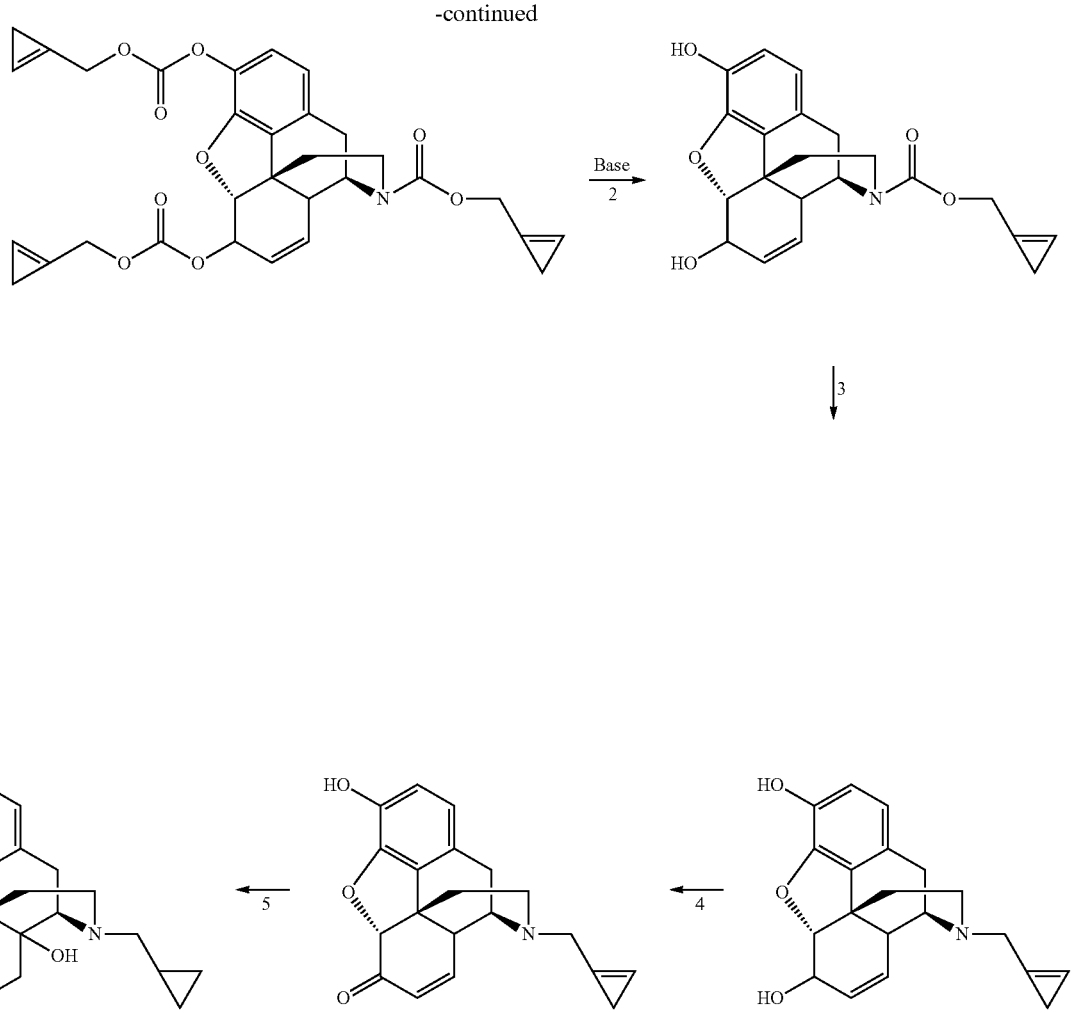

As indicated in Scheme 31, the 3- and 6-hydroxyl of morphine can be converted to the bis-cycloprop-1-en-1-ylmethyl carbonate derivative during the depicted N-demethylation reaction with cycloprop-1-en-1-ylmethyl chloroformate. In Step 2, the carbonate groups can be removed while the carbamate can be converted to the N-cyclopropenylmethyl derivative in Step 3 using the transition metal-catalyzed decarboxylation reactions disclosed herein. Conversion of the 6-hydroxyl group to a keto moiety (Step 4) and introduction of the 14-hydroxyl group and hydrogenation of the indicated double bonds (Step 5) can be carried out using methods disclosed herein or using those disclosed, e.g., in U.S. Pat. No. 5,952,495. Alternatively, the process of Scheme 31 could further modified by utilizing protecting groups for the 3- and 6-hydroxyl groups and, subsequently, hydrolyzing those protecting groups either before or after the transition metal-catalyzed decarboxylation reactions, as depicted in Scheme 32.

Scheme 32

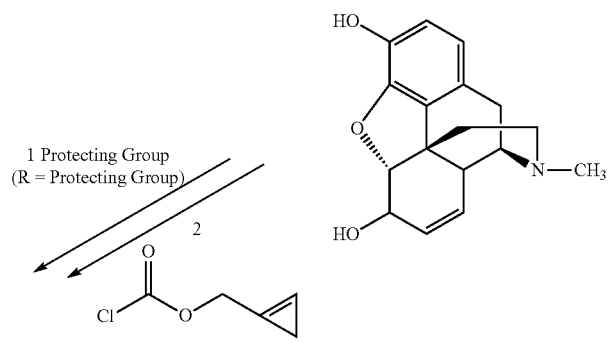

135

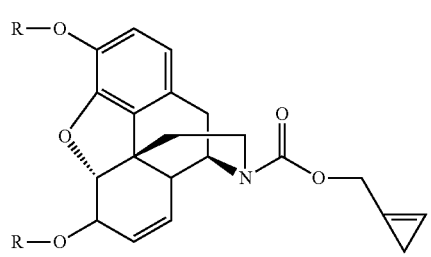

-continued

Alcohol deprotection
3A →

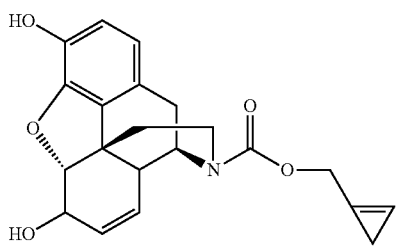

3B | Transition Metal Decarbonylation

4A | Transition Metal Decarbonylation

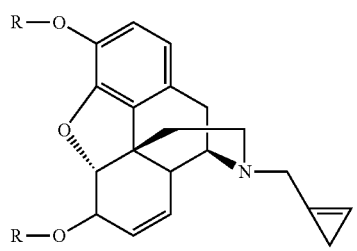

Alcohol deprotection
4B →

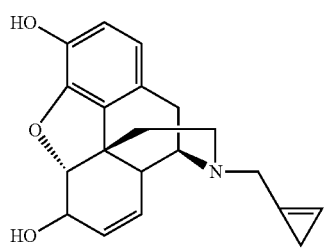

5 ↓

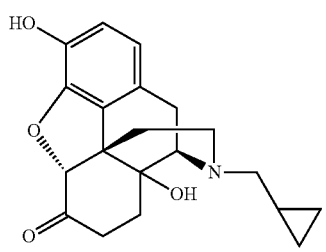

← 6

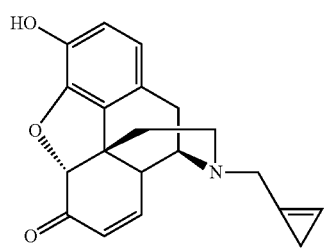

As indicated in Scheme 32, the 3- and 6-hydroxyl of morphine can be protected with a suitable oxygen protecting group (Step 1) before N-demethylation with cycloprop-1-en-1-ylmethyl chloroformate (Step 2). In one route, the protecting groups are removed (Step 3A) before conversion of the carbamate to the N-cyclopropenylmethyl derivative (Step 4A) using the transition metal-catalyzed decarboxylation reactions disclosed herein. Alternatively, the transition metal decarboxylation (Step 3B) can be carried out before removal of the protecting groups (Step 4B). Conversion of the 6-hydroxyl group to a keto moiety, introduction of the 14-hydroxyl group, and hydrogenation of the indicated double bonds can be carried out using methods disclosed herein or using those disclosed, e.g., in U.S. Pat. No. 5,952,495. In another alternative embodiment, the oxygen protecting group is selected from among those removed during the hydrogenation reaction (e.g., R is benzyl), thereby obviating the need for Step 4B.

4.27.2 Preparation of Naltrexone from Codeine

Schwartz (Schwartz et al. (1981) J. Med. Chem. (1981) 24:1525-1528) describe a set of reactions that could be used to convert codeine to naltrexone in eight steps. According to this method, codeine is N-demethylated with ethyl chloroformate and then oxidized with manganese dioxide to provide N-(ethoxycarbonyl)norcodeinone which, upon treatment with sodium acetate in acetic anhydride, provides a dienol acetate derivative. Oxidation of that compound with singlet oxygen provided the corresponding 14-hydroxy product. Hydrogenation of the 7,8-double bond, hydrolysis of the N-ethyloxycarbonyl moiety followed by alkylation with cyclopropyl methyl bromide, and conversion of the 3-methoxy group to a hydroxyl group with boron tribromide would complete the conversion of codeine to naltrexone.

Scheme 33

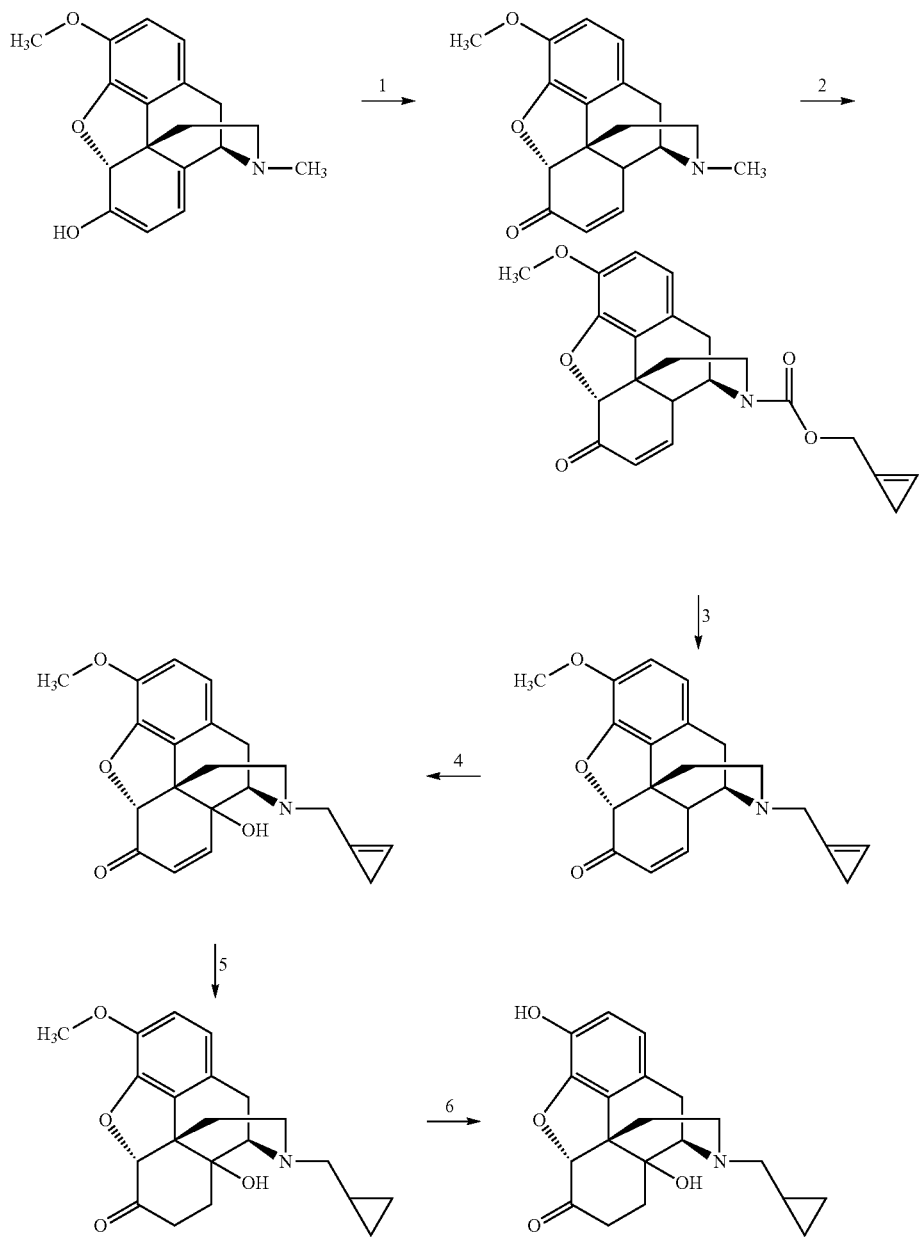

As indicated in Step 1 in Scheme 33, codeine is oxidized to provide the 6-keto derivative, which is converted to the corresponding N-cyclopropylmethyl compound in Steps 2 and 3 using the transition metal-catalyzed decarboxylation reactions disclosed herein. The N-cyclopropylmethyl is oxidized to include the 14-hydroxyl group (e.g., by reaction with hydrogen peroxide in formic acid as disclosed in U.S. Pat. No. 5,952,495). Hydrogenation of the double bonds and conversion of the 3-methoxy group to a 3-hydroxyl by known methods completes the process of Scheme 33, providing naltrexone from codeine in six steps.

4.27.3 Preparation of Naltrexone from Thebaine

The disclosure of GB 939287 can be used to provide a seven step process for conversion of thebaine to naltrexone. In this process, thebaine is oxidized to 14-hydroxycodeinone, which is hydrogenated to oxycodone. The 14-hydroxyl group of oxycodone is first acetylated and the thus-protected compound first reacted with cyanogen bromide and then hydrolyzed to noroxycodone. Alkylation with cyclopropylmethyl bromide and conversion of the methoxy group to a hydroxyl moiety provides the final product, naltrexone. U.S. Pat. Nos. 4,639,520 and 4,472,253 and WO 98/02033 A1 also can be used to provide a seven step process for conversion of thebaine to naltrexone that differs from that of the GB 939287 patent with respect to the order in which the reactions are carried out.

In contrast, naltrexone can be prepared from thebaine in five steps according to methods disclosed herein, e.g., as depicted in Scheme 34.

Scheme 34

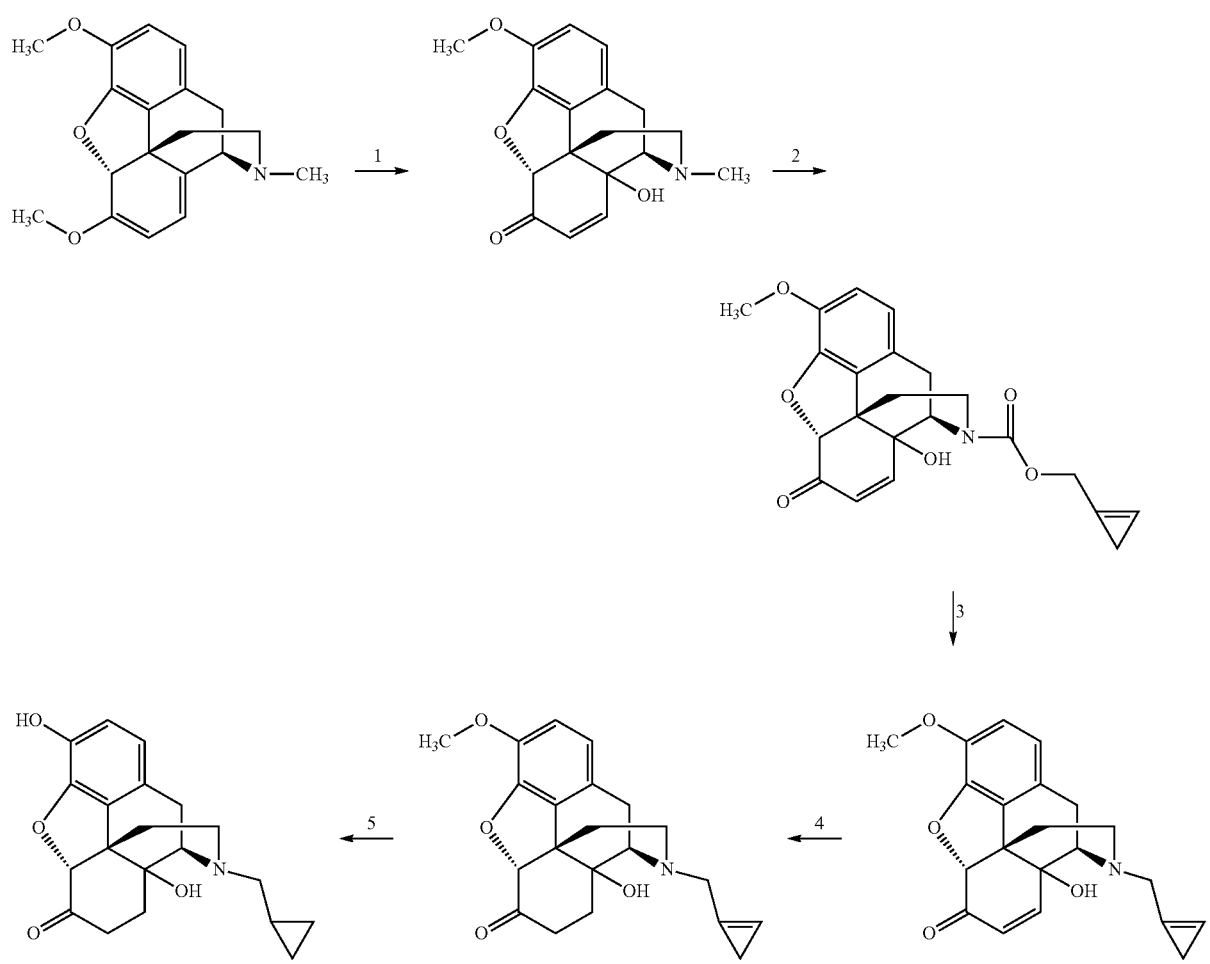

As indicated in Scheme 34, thebaine can be oxidized to introduce the 14-hydroxyl moiety (Step 1), and the N-methyl group replaced with a cyclopropyl methyl in Steps 2-4, including the transition metal-catalyzed decarboxylation reaction of Step 3 according to the methods disclosed herein. Conversion of the 3-methoxy group to a 3-hydroxyl by known methods completes the process of Scheme 34, providing naltrexone from thebaine in five steps.

4.28 Compositions

The present disclosure also provides a composition comprising a compound of formula (42)

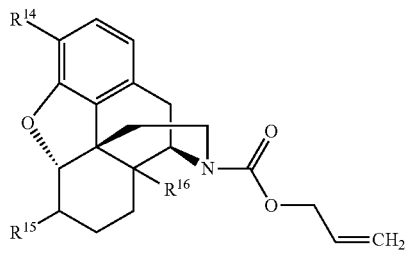

and a transition metal catalyst, where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In another embodiment, the present disclosure provides a composition prepared by admixing a compound of formula (42)

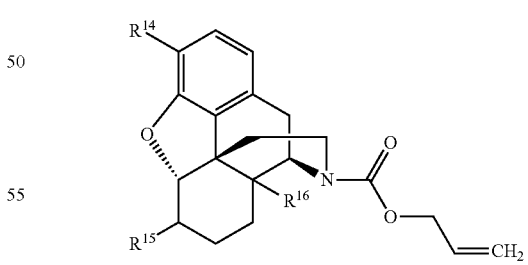

and a transition metal catalyst, where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In another embodiment, the present disclosure provides a method for preparing a composition containing a compound of formula (42) comprising admixing the compound of formula (42)

141

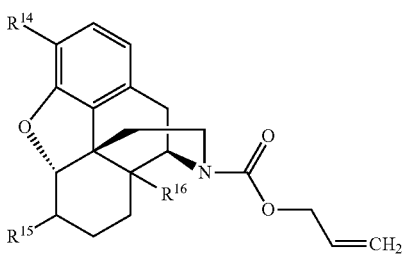

and a transition metal catalyst, where $R^{14}$ and $R^{16}$ are each independently selected from —OH, —H, and —OR$^{17}$; $R^{15}$ is selected from —OH, —H, —OR$^{17}$, =O, and =CH$_2$; and $R^{17}$ is an oxygen protecting group.

In another embodiment, the present disclosure provides a composition comprising a tertiary alcohol and a compound of formula (93)

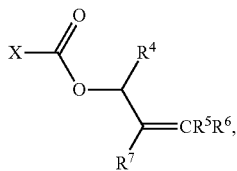

where $R^4$ is selected from the group consisting of —H, —(C$_1$-C$_6$) alkyl, phenyl, allyl, -2-butenyl, -3-butenyl, -4-pentenyl, -2-propynyl, -2-butynyl, -3-butynyl, -2-pentynyl,

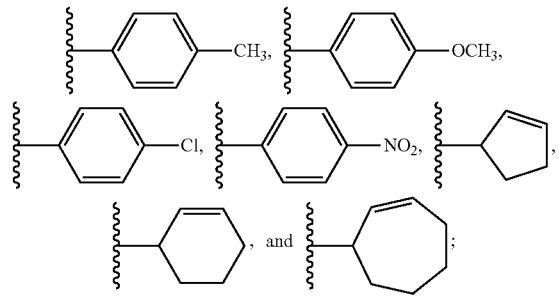

$R^5$, $R^6$, and $R^7$ are each independently selected from —H, —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; each $R^8$ is independently selected from —OR$^{51}$, —F, —Cl, —Br, —I, phenyl, and —(C$_1$-C$_6$) alkyl; each $R^{51}$ is independently selected from —(C$_1$-C$_6$) alkyl and an oxygen protecting group; and X is selected from —Cl, —Br, and —I. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —OR$^{51}$, —F, —Cl, —Br, —I, phenyl, or —(C$_1$-C$_6$) alkyl; and $R^{51}$ is —(C$_1$-C$_6$) alkyl or an oxygen protecting group.

142

In another embodiment, the present disclosure provides a composition comprising a tertiary alcohol and a compound of formula (6)

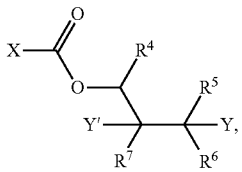

where one of Y and Y' is a leaving group and the other is —H; $R^4$ is selected from the group consisting of —H, —(C$_1$-C$_6$) alkyl, phenyl, allyl, -2-butenyl, -3-butenyl, -4-pentenyl, -2-propynyl, -2-butynyl, -3-butynyl, -2-pentynyl,

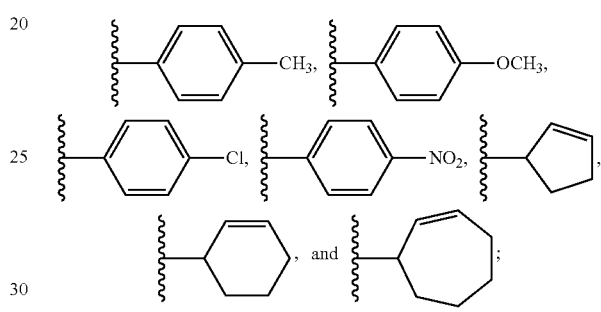

$R^5$, $R^6$, and $R^7$ are each independently selected from —H, —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; each $R^8$ is independently selected from —OR$^{51}$, —F, —Cl, —Br, —I, phenyl, and —(C$_1$-C$_6$) alkyl; each $R^{51}$ is independently selected from —(C$_1$-C$_6$) alkyl and an oxygen protecting group; and X is selected from —Cl, —Br, and —I. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —OR$^{51}$, —F, —Cl, —Br, —I, phenyl, or —(C$_1$-C$_6$) alkyl; and $R^{51}$ is —(C$_1$-C$_6$) alkyl or an oxygen protecting group.

In another embodiment, the present disclosure provides a composition comprising a tertiary alcohol and a compound of formula (8)

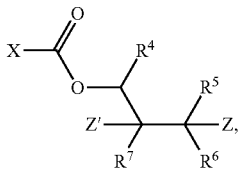

where $R^4$ is selected from the group consisting of —H, —(C$_1$-C$_6$) alkyl, phenyl, allyl, -2-butenyl, -3-butenyl, -4-pentenyl, -2-propynyl, -2-butynyl, -3-butynyl, -2-pentynyl,

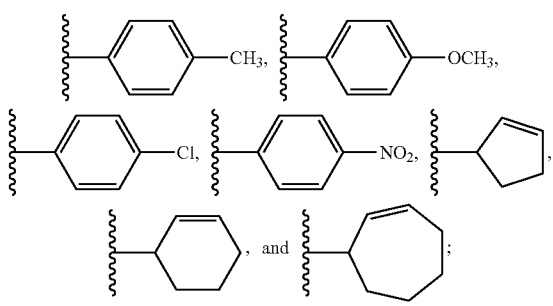

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; each $R^8$ is independently selected from —$OR^{51}$, —F, —Cl, —Br, —I, phenyl, and —($C_1$-$C_6$) alkyl; each $R^{51}$ is independently selected from —($C_1$-$C_6$) alkyl and an oxygen protecting group; and X, Z, and Z' are each independently selected from —Cl, —Br, and —I. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In another embodiment, the present disclosure provides a composition comprising a tertiary alcohol and a compound of formula (13)

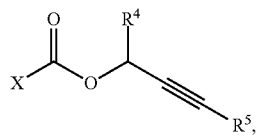

where $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

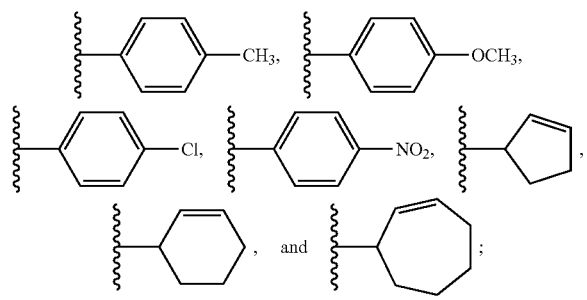

$R^5$ is selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups; each $R^8$ is independently selected from —$OR^{51}$, —F, —Cl, —Br, —I, phenyl, and —($C_1$-$C_6$) alkyl; each $R^{51}$ is independently selected from —($C_1$-$C_6$) alkyl and an oxygen protecting group; and X is selected from —Cl, —Br, and —I.

In another embodiment, the present disclosure provides a composition comprising a tertiary alcohol and a compound of formula (19)

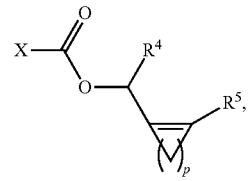

where $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

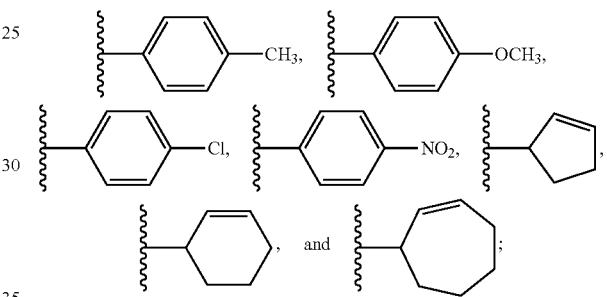

$R^5$ is selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups; each $R^8$ is independently selected from —$OR^{51}$, —F, —Cl, —Br, —I, phenyl, and —($C_1$-$C_6$) alkyl; each $R^{51}$ is independently selected from —($C_1$-$C_6$) alkyl and an oxygen protecting group; p is an integer selected from 1, 2, 3, and 4; and X is selected from —Cl, —Br, and —I.

In another embodiment, the present disclosure provides a composition comprising a tertiary alcohol and a compound of formula (23)

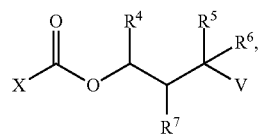

where $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

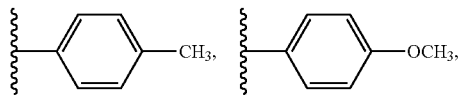

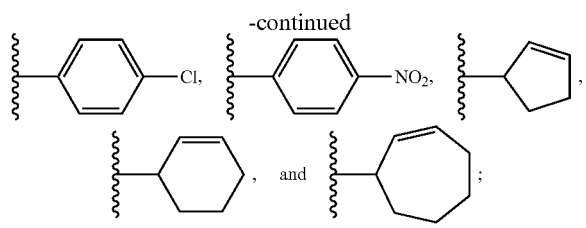

$R^5$, $R^6$, and $R^7$ are each independently selected from —H, —($C_1$-$C_6$) alkyl, —($C_2$-$C_6$) alkenyl, and —($C_2$-$C_6$) alkynyl, each alkyl, alkenyl, and alkynyl being unsubstituted or substituted with 1, 2, 3, 4, or 5 independently-selected $R^8$ groups, or $R^6$ and $R^7$ are taken together with the carbon atoms to which each is bound to form a carbocyclic ring of 3, 4, 5, 6, 7, 8, or 9 carbon atoms, the carbocyclic ring being unsubstituted or substituted with 1, 2, 3, 4, or 5 independently-selected $R^8$ groups; each $R^8$ is independently selected from —$OR^{51}$, —F, —Cl, —Br, —I, phenyl, and —($C_1$-$C_6$) alkyl; each $R^{51}$ is independently selected from —($C_1$-$C_6$) alkyl and an oxygen protecting group; V is a leaving group; and X is selected from —Cl, —Br, and —I. In certain embodiments, $R^6$ and $R^7$ are taken together with the carbon atoms to which each is bound to form a carbocyclic ring of 3, 4, 5, or 6 carbon atoms, the carbocyclic ring being unsubstituted or substituted with 1, 2, 3, 4, or 5 independently-selected $R^8$ groups; $R^8$ is —$OR^{51}$, —F, —Cl, —Br, —I, phenyl, or —($C_1$-$C_6$) alkyl; and $R^{51}$ is —($C_1$-$C_6$) alkyl or an oxygen protecting group.

In another embodiment, the present disclosure provides a composition comprising a tertiary alcohol and a compound of formula (29)

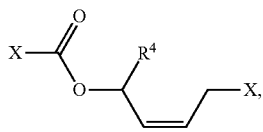

where $R^4$ is selected from the group consisting of —H, —($C_1$-$C_6$) alkyl, phenyl, allyl, -2-butenyl, -3-butenyl, -4-pentenyl, -2-propynyl, -2-butynyl, -3-butynyl, -2-pentynyl,

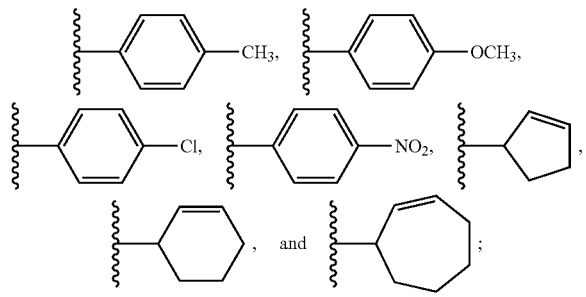

and each X is independently selected from —Cl, —Br, and —I.

In another embodiment, the present disclosure provides a composition comprising a tertiary alcohol and a compound of formula (46)

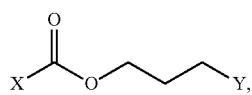

where Y is a leaving group; and X is selected from —Cl, —Br, and —I.

In each of the compositions in Section 4.28 containing a tertiary alcohol, in one embodiment the tertiary alcohol is a compound of formula (4)

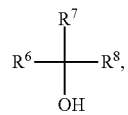

where $R^6$, $R^7$, and $R^8$ are each independently —($C_1$-$C_6$) alkyl. In another embodiment, the tertiary alcohol is selected from the group consisting of tert-amyl alcohol, tert-butyl alcohol, 3-methyl-3-pentanol, 2,3-dimethyl-3-pentanol, 3-ethyl-3-pentanol, 2-methyl-2-hexanol, and combinations of two or more thereof. In another embodiment, the tertiary alcohol is tert-amyl alcohol.

In each of the compositions in Section 4.28 containing a tertiary alcohol, in one embodiment the composition can further comprise an iodide salt. In certain embodiments, the iodide salt is present in a sub-stoichiometric amount. In certain embodiments, the iodide salt is present in a catalytic amount. In another embodiment, the iodide salt is selected from the group consisting of NaI, KI, LH, CsI, RuI, $MgI_2$, $CaI_2$, $NH_4I$, tetrabutylammonium iodide, and combinations of two or more thereof. In another embodiment, the iodide salt is NaI.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

The reactions and processes of the present disclosure are described in more detail below.

Example 1

N-Demethylation of Oxycodone

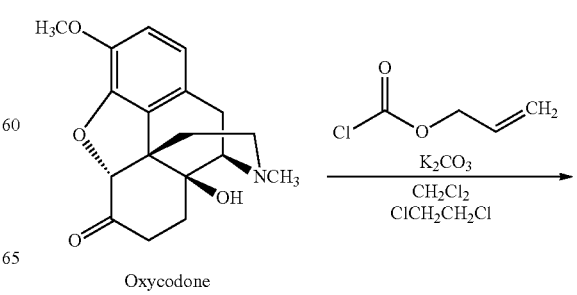

Oxycodone

-continued

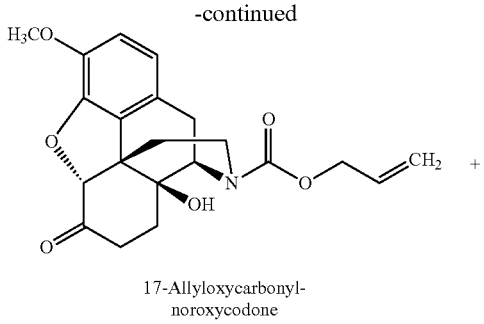

17-Allyloxycarbonyl-
noroxycodone

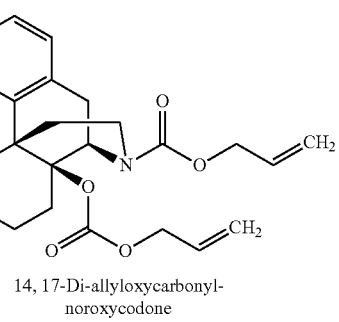

14,17-Di-allyloxycarbonyl-
noroxycodone

Into a round bottom flask equipped with a stir bar was charged oxycodone (3.15 g, 9.99 mmol), potassium carbonate (2.07 g, 15.0 mmol), dichloromethane (31.5 mL), and 1,2-dichloroethane (15 mL). The flask was equipped with a reflux condenser and the mixture was allowed to stir at a temperature of about 20° C. under an atmosphere of nitrogen. Into the mixture was added a first portion of allyl chloroformate (6.35 mL, 59.95 mmol) drop-wise over 5 minutes. The resulting reaction mixture was heated to reflux at 52.5° C. and allowed to stir at that temperature for 16 hours. Thereafter, the reaction mixture was sampled and analyzed by HPLC; approximately 32% of the starting oxycodone was determined to remain.

Into the mixture was added a second and final portion (3.2 mL, 30.21 mmol) of allyl chloroformate and an additional 16.5 mL of 1,2-dichloroethane. The resulting reaction mixture was heated to reflux at 57.5° C. and allowed to stir for an additional 24 hours. Thereafter, the reaction mixture was sampled and analyzed by HPLC; approximately 22% of oxycodone was determined to remain.

The mixture was cooled to a temperature of about 20° C. and filtered through a pad of CELITE to remove residual solids. The filtrate was concentrated under reduced pressure. The resulting material was dissolved in a mixture of ethyl acetate (150 mL) and 0.5N aqueous hydrochloric acid (120 mL). The layers were separated and the organic layer was washed with water (100 mL). The organic layer was concentrated under reduced pressure to provide a 2:1 mixture of 17-allyloxycarbonyl-noroxycodone:14,17-di-allyloxycarbonyl-noroxycodone as a yellow oil (1.98 g, 4.79 mmol).

Example 2

N-Demethylation of Oxymorphone

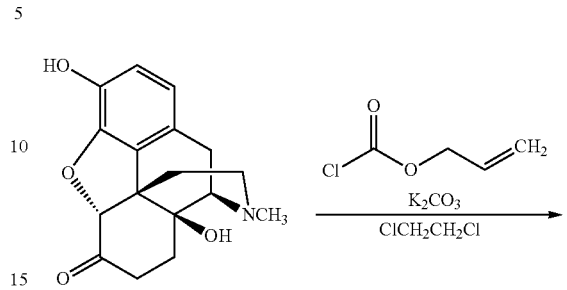

Oxymorphone

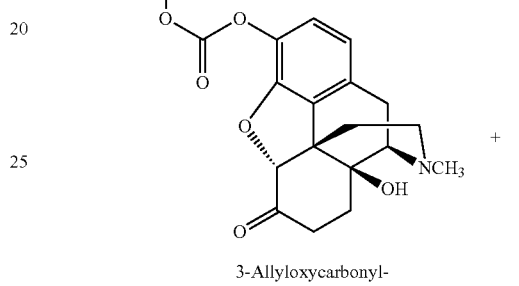

3-Allyloxycarbonyl-
oxymorphone

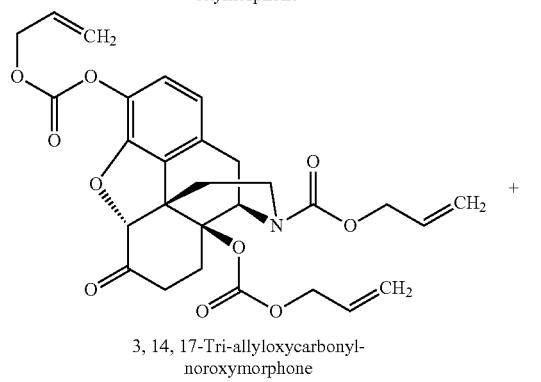

3,14,17-Tri-allyloxycarbonyl-
noroxymorphone

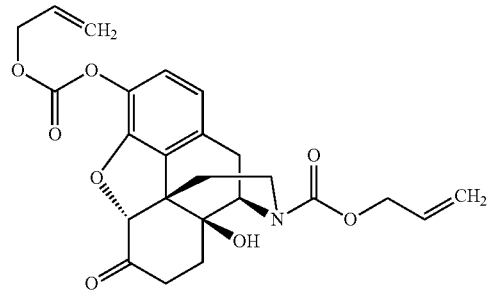

3,17-Di-allyloxycarbonyl-
noroxymorphone

Into a round bottom flask equipped with a stir bar was charged oxymorphone (6.02 g, 19.96 mmol), potassium carbonate (4.15 g, 30.03 mmol), and 1,2-dichloroethane (60 mL). The flask was equipped with a reflux condenser and the mixture was allowed to stir at a temperature of about 20° C. under an atmosphere of nitrogen. Into the mixture was added a first portion of allyl chloroformate (12.7 mL, 119.91 mmol) drop-wise over 10 minutes. The resulting reaction mixture was heated to reflux at 81.5° C. and allowed to stir at that temperature for 18 hours. Thereafter, the reaction mixture was sampled and analyzed by HPLC; approximately 24% of 3-allyloxycarbonyl oxymorphone was determined to be present. As noted above, at initial time points the major product observed was 3-allyloxycarbonyl-oxymorphone.

Into the mixture was added a second and final portion (4.2 mL, 39.65 mmol) of allyl chloroformate and an additional 2.07 g (14.98 mmol) of potassium carbonate. The resulting reaction mixture was allowed to stir for an additional 24 hours at reflux. Thereafter, the reaction mixture was sampled and analyzed by HPLC; approximately 18% of 3-allyloxycarbonyl oxymorphone was determined to be present.

The mixture was cooled to a temperature of about 20° C. and filtered through a pad of CELITE to remove residual solids. The filtrate was concentrated under reduced pressure. The resulting material was dissolved in a mixture of ethyl acetate (200 mL) and 0.5N aqueous hydrochloric acid (150 mL). The organic layer was dried with sodium sulfate, filtered, and concentrated under reduced pressure to provide a 3:1 mixture of 3,17-di-allyloxycarbonyl-noroxymorphone: 3,14,17-tri-allyloxycarbonyl-noroxymorphone as a yellow oil (5.64 g, 12.38 mmol).

Example 3

N-Demethylation of Oxymorphone bonate (8.46 g, 100.70 mmol), and tert-amyl alcohol (70 mL). The flask was equipped with a Dean-Stark trap and condenser. The mixture was allowed to stir at a temperature of about 20° C. for 5 minutes. Into the mixture was added a first portion of allyl chloroformate (3.90 mL, 36.69 mmol) drop-wise over 5 minutes. The resulting reaction mixture was heated to 55° C. and allowed to stir at that temperature for 1 hour. Thereafter, the reaction mixture was sampled and analyzed by HPLC; the conversion to 3-allyloxycarbonyl-oxymorphone was determined to be greater than 99%. The reaction mixture was heated to 105° C. and 25 mL of reaction solvent was removed from the round bottom flask by distillation into the Dean-Stark trap.

The mixture was cooled to 85° C. Into the mixture was added a second portion of allyl chloroformate (8.90 mL, 83.73 mmol). The resulting reaction mixture was allowed to stir at 85° C. for 6 hours and then cooled to a temperature of about 20° C. and stirred at that temperature for 16 hours. Thereafter, the reaction mixture was sampled and analyzed by HPLC; approximately 42% of 3-allyloxycarbonyl-oxymorphone was determined to remain. The 25 mL of liquid in the Dean-Stark trap was emptied and an additional 30 mL of tert-amyl alcohol was added to the mixture. The resulting reaction mixture was heated to 105° C. and 25 mL of reaction solvent was removed from the round bottom flask by distillation into the Dean-Stark trap.

The mixture was cooled to 85° C. and a third portion of allyl chloroformate (3.90 mL, 36.69 mmol) was added. The

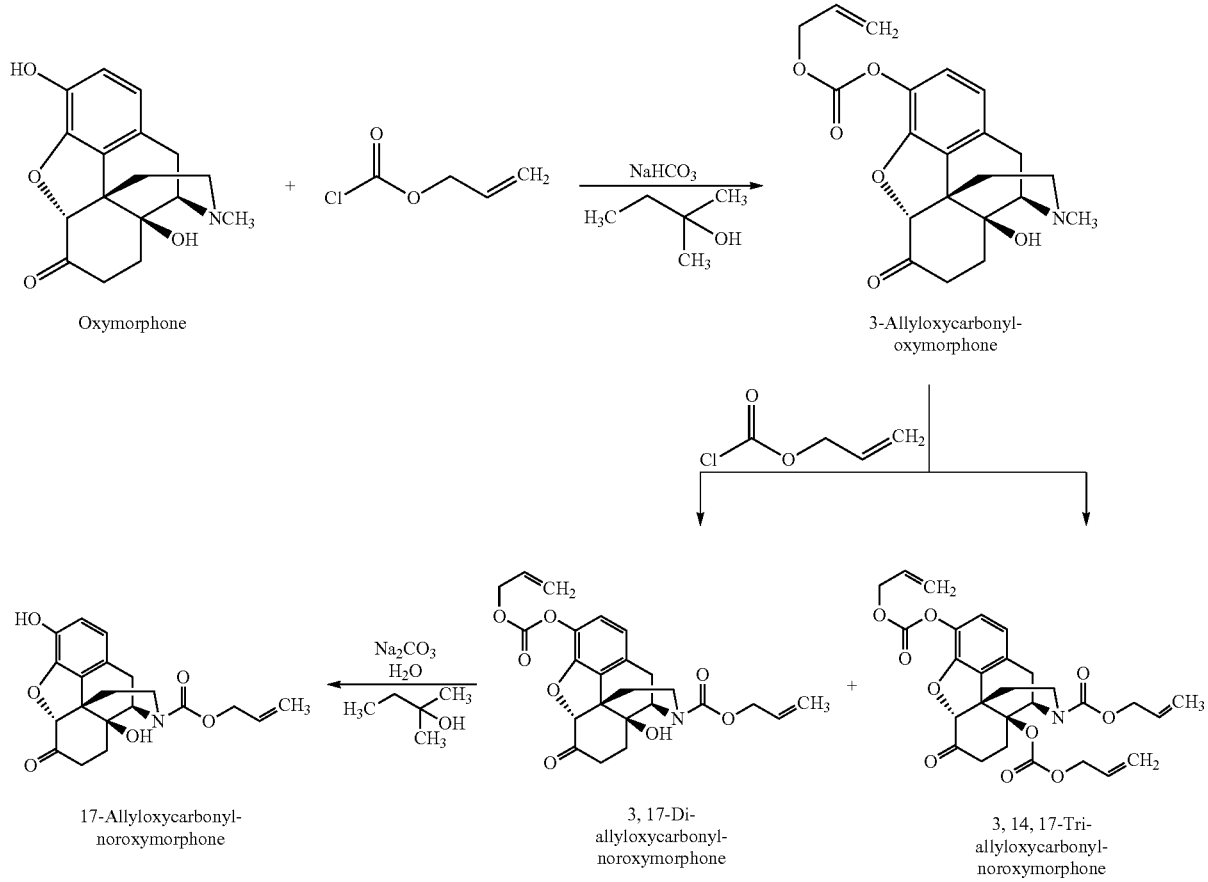

Into a round bottom flask equipped with a stir bar was charged oxymorphone (10.06 g, 33.38 mmol), sodium bicarresulting reaction mixture was allowed to stir at 85° C. for 6 hours and then cooled to a temperature of about 20° C. and stirred at that temperature for 16 hours. Thereafter, the reaction mixture was sampled and analyzed by HPLC; approximately 28% of 3-allyloxycarbonyl-oxymorphone was determined to remain. The 25 mL of liquid in the Dean-Stark trap was emptied and an additional 20 mL of tert-amyl alcohol was added to the mixture. The resulting reaction mixture was heated to 105° C. and 25 mL of reaction solvent was removed from the round bottom flask by distillation into the Dean-Stark trap.

The mixture was cooled to 85° C. and a fourth portion of allyl chloroformate (3.90 mL, 36.69 mmol) was added. The resulting reaction mixture was allowed to stir at 85° C. for 6 hours and then cooled to a temperature of about 20° C. and stirred at that temperature for 16 hours. Thereafter, the reaction mixture was sampled and analyzed by HPLC; approximately 7% of 3-allyloxycarbonyl-oxymorphone was determined to remain. The 25 mL of liquid in the Dean-Stark trap was emptied and an additional 25 mL of tert-amyl alcohol was added to the mixture. The resulting reaction mixture was heated to 105° C. and 25 mL of reaction solvent was removed from the round bottom flask by distillation into the Dean-Stark trap.

The mixture was cooled to 85° C. and a fifth and final portion of allyl chloroformate (3.90 mL, 36.69 mmol) was added. The resulting reaction mixture was allowed to stir at 85° C. for 6 hours and then cooled to a temperature of about 20° C. and stirred at that temperature for 16 hours. Thereafter, the reaction mixture was sampled and analyzed by HPLC; approximately 0.6% of 3-allyloxycarbonyl-oxymorphone was determined to remain. HPLC analysis also demonstrated that a 6.3:1 mixture of 3,17-di-allyloxycarbonyl-noroxymorphone:3,14,17-tri-allyloxycarbonyl-noroxymorphone was prepared.

To the reaction mixture was added sodium carbonate (4.74 g, 44.72 mmol) and water (35 mL). The reaction mixture was heated to 90° C. and allowed to stir at that temperature for 17 hours. The reaction mixture was cooled to a temperature of about 20° C. and sampled for HPLC analysis; the results demonstrated that greater than 99% conversion to 17-allyloxycarbonyl-noroxymorphone was achieved. The reaction mixture was acidified to a pH of 1.5 with concentrated hydrochloric acid (10 mL) and the mixture was allowed to stir for 10 minutes. Mixing was stopped and the layers were allowed to separate. The organic layer was separated and washed twice with 10% aqueous sodium hydrogen sulfate (50 mL for each wash). The organic layer was concentrated under reduced pressure to provide crude 17-allyloxycarbonyl-noroxymorphone as a yellow foam (8.85 g, 23.83 mmol).

Example 4

Decarboxylative Allylation of 17-Allyloxycarbonyl-Noroxycodone and 14,17-Di-Allyloxycarboynly-Noroxycodone

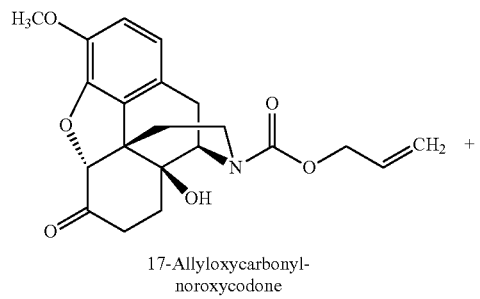

17-Allyloxycarbonyl-noroxycodone +

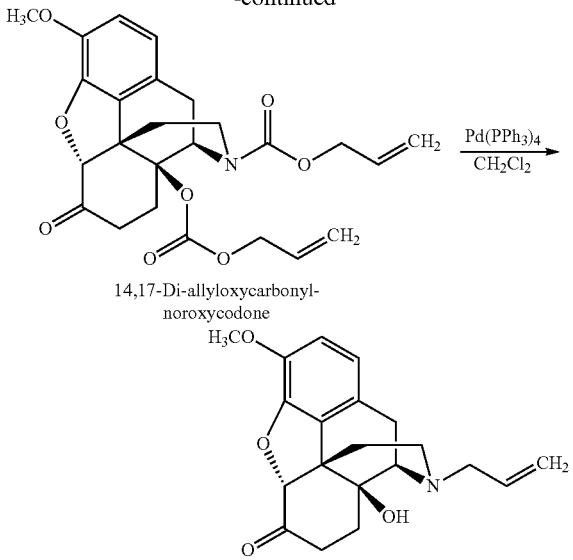

14,17-Di-allyloxycarbonyl-noroxycodone

Into a round bottom flask equipped with a stir bar was dissolved a 2:1 mixture of 17-allyloxycarbonyl-noroxycodone:14,17-di-allyloxycarbonyl-noroxycodone (264 mg, 0.67 mmol) in dichloromethane (5 mL). The mixture was allowed to stir at a temperature of about 20° C. for 10 minutes. To the mixture was added tetrakis(triphenylphosphine)palladium[0] (40 mg, 0.035 mmol). The resulting reaction mixture was allowed to stir at a temperature of about 20° C. for 3 hours before being filtered through a pad of CELITE. The filtrate was concentrated under reduced pressure. The resulting oil was dissolved in ethyl acetate (20 mL) and the product was extracted with 0.5N aqueous hydrochloric acid (100 mL). The aqueous layer was basified to a pH of 10.2 with 50% sodium hydroxide and extracted three times with dichloromethane (150 mL for each extraction). The combined organic portions were dried with sodium sulfate, filtered, and concentrated under reduced pressure to provide N-allyl-oxycodone as a yellow oil (183 mg, 0.54 mmol).

Example 5

Decarboxylative Allylation of 3,17-Di-Allyloxycarbonyl-Noroxymorpone:3,14,17-Tri-Allyloxycarbonyl-Noroxymorphone 3,17-Di-allyloxycarbonyl-noroxymorphone +

-continued

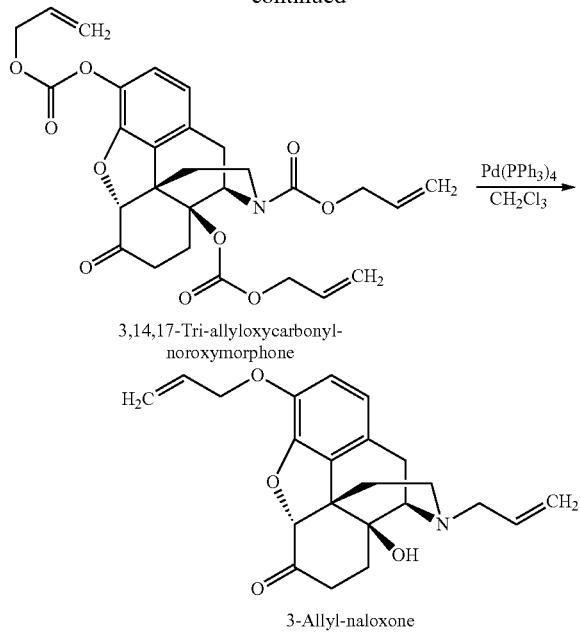

3,14,17-Tri-allyloxycarbonyl-noroxymorphone

3-Allyl-naloxone

Into a round bottom flask equipped with a stir bar was dissolved a 3:1 mixture of 3,17-di-allyloxycarbonyl-noroxymorphone:3,14,17-tri-allyloxycarbonyl-noroxymorphone (1.41 g, 2.98 mmol) in chloroform (10 mL). The mixture was allowed to stir at a temperature of about 20° C. for 10 minutes. To the mixture was added tetrakis(triphenylphosphine)palladium[0] (180 mg, 0.155 mmol). The resulting reaction mixture was allowed to stir at a temperature of about 20° C. for 4 hours before being filtered through a pad of CELITE. The filtrate was concentrated under reduced pressure. The resulting oil was dissolved in ethyl acetate (100 mL) and the product was extracted with 0.5N aqueous hydrochloric acid (100 mL). The aqueous layer was washed twice with ethyl acetate (100 mL for each wash). The aqueous layer was basified to a pH of 9.5 with 50% sodium hydroxide and extracted three times with chloroform (100 mL for each extraction). The organic portions were combined, dried with sodium sulfate, filtered, and concentrated under reduced pressure to provide 3-allyl-naloxone as a yellow oil, contaminated with approximately 25% of triphenylphosphine (1.41 g of oil containing about 1.05 g of 3-allyl-naloxone (about 2.88 mmol)).

Example 6

O-De-Allylation of 3-Allyl-Naloxone

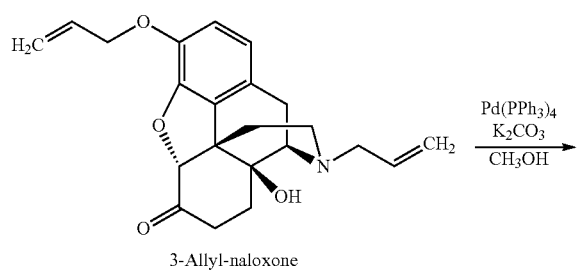

3-Allyl-naloxone

-continued

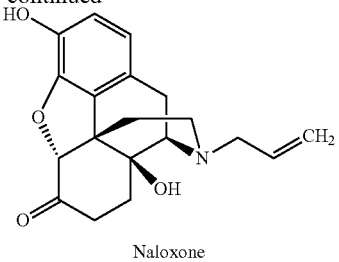

Naloxone

Into a round bottom flask equipped with a stir bar was dissolved 3-allyl-naloxone (0.28 g, 0.76 mmol) in methanol (10 mL). To the mixture was added potassium carbonate (0.40 g, 2.89 mmol) and tetrakis(triphenylphosphine)palladium[0] (0.0215 g, 0.019 mmol). The resulting reaction mixture was allowed to stir at a temperature of about 20° C. for 4 hours. Thereafter, the reaction mixture was sampled and analyzed by HPLC; the results demonstrated that greater than 99% conversion to naloxone was achieved. The mixture was filtered through a pad of CELITE and the filtrate was concentrated under reduced pressure. The resulting oil was dissolved in ethyl acetate (50 mL) and extracted with 0.5N aqueous hydrochloric acid (75 mL). The aqueous layer was washed twice with ethyl acetate (50 mL for each wash). The aqueous layer was basified to a pH of 9.0 with 50% sodium hydroxide and extracted three times with chloroform (50 mL for each extraction). The organic portions were combined, dried with sodium sulfate, filtered, and concentrated under reduced pressure to provide naloxone as a yellow oil (0.23 g, 0.70 mmol).

Example 7

N-De-Allylation of Naloxone

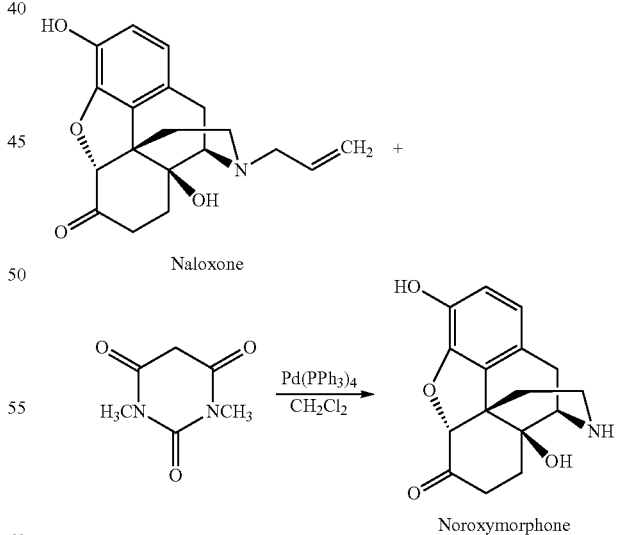

Into a 5 L reactor equipped with an overhead stirrer and reflux condenser was dissolved N,N-dimethyl barbituric acid (32.56 g, 208.5 mmol) and tetrakis(triphenylphosphine) palladium[0] (20.36 g, 17.6 mmol) in dichloromethane (1.5 L). The mixture was stirred at a temperature of about 20° C. Into the mixture was charged naloxone (110.90 g, 338.8 mmol) as a suspension in dichloromethane (1 L). The resulting reaction mixture was stirred at 38° C. for 16 hours. The mixture was cooled to a temperature of about 20° C. and the solids were filtered off under reduced pressure. The solids were washed with dichloromethane (5 L) followed by washing with water (2.5 L). The solids were dissolved into a 10:1 mixture of water:concentrated sulfuric acid at 40° C. The heated aqueous solution was washed with dichloromethane (0.5 L) and then basified to a pH of 9.05 with 28% ammonium hydroxide. The resulting solids were filtered and dried under reduced pressure at 100° C. for 20 hours to provide noroxymorphone as a white solid (87.12 g, 303.2 mmol).

Example 8

Allylation of Noroxymorphone with Allyl Acetate

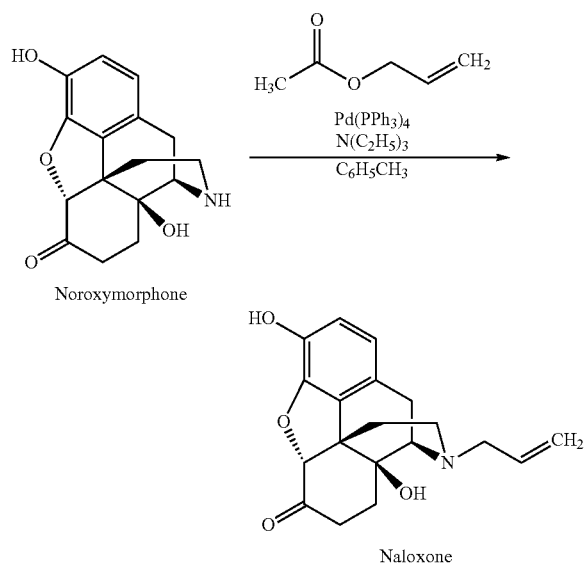

Into a round bottom flask equipped with a stir bar was charged noroxymorphone (2.89 g, 10.1 mmol), triethylamine (4.20 mL, 30.1 mmol), toluene (50 mL), tetrakis(triphenylphosphine)palladium[0] (1.15 g, 1.00 mmol), and allyl acetate (1.40 mL, 12.9 mmol). The flask was equipped with a reflux condenser and the resulting reaction mixture was stirred and heated at 80° C. for 64 hours. The mixture was cooled to a temperature of about 20° C. and filtered through a plug of CELITE. The filtrate was concentrated under reduced pressure. The concentrated material was dissolved in a mixture of ethyl acetate (150 mL) and 0.75N aqueous hydrochloric acid (100 mL) and allowed to stir at a temperature of about 20° C. for 20 minutes. The layers were separated and the aqueous layer was washed with an additional 150 mL of ethyl acetate. The aqueous layer was basified to a pH of 9.05 with 28% ammonium hydroxide and extracted twice with dichloromethane (100 mL for each extraction). The organic portions were combined and concentrated under reduced pressure. Naloxone (HPLC purity of 76%) was isolated as an oil, contaminated with triphenylphosphine and 3-allyl-naloxone (isolated 2.78 g crude of 76% purity containing about 6.37 mmol of naloxone)).

Example 9

Allylation of Noroxymorphone with N-Allyl-dimethylamine

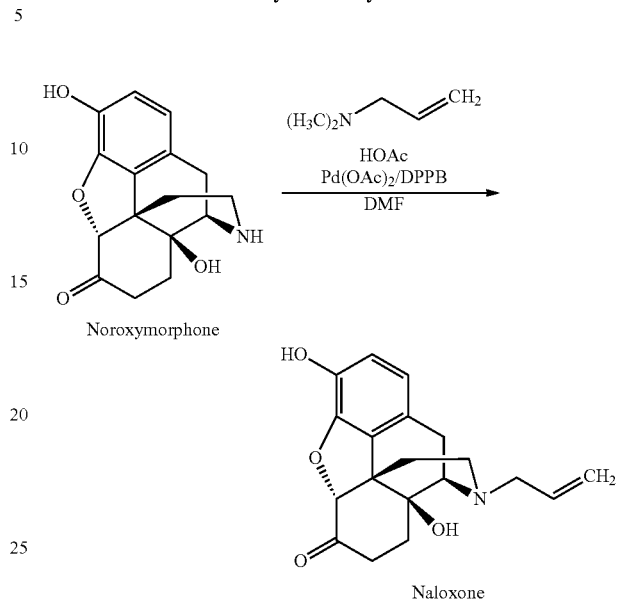

Into a round bottom flask equipped with a stir bar was charged 1,4-bis(diphenylphosphino)-butane (0.352 g, 0.82 mmol), palladium(II) acetate (0.10 g, 0.44 mmol), and DMF (10 mL). The flask was sealed and stirred at a temperature of about 20° C. for 15 minutes. Thereafter, into the flask was added N-allyl-dimethylamine (1.45 mL, 12.2 mmol), followed by noroxymorphone (2.85 g, 9.92 mmol) as a slurry in DMF (30 mL) and acetic acid (1.20 mL, 21.0 mmol). The flask was equipped with a reflux condenser and the resulting reaction mixture was stirred and heated at 50° C. for 16 hours. Thereafter, the reaction mixture was sampled and analyzed by HPLC; conversion to naloxone was determined to be low, no more than approximately 1-2%.

Example 10

N-Demethylation of N-Methylmorpholine

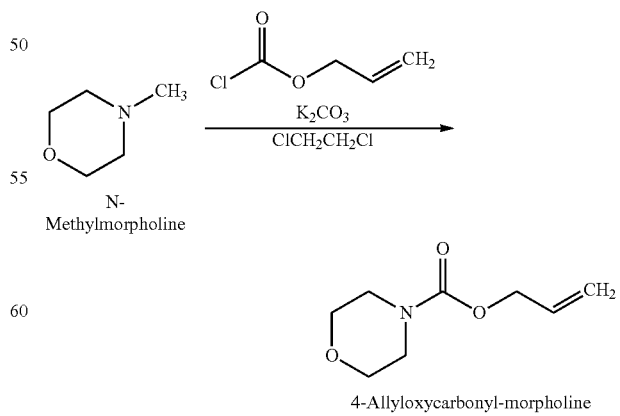

Into a round bottom flask equipped with a stir bar was charged N-methylmorpholine (2.50 mL, 22.7 mmol), 1,2- dichloroethane (35 mL), and potassium carbonate (4.75 g, 34.4 mmol). The flask was equipped with a reflux condenser and the mixture was allowed to stir at a temperature of about 20° C. under an atmosphere of nitrogen. Into the mixture was added a first portion of allyl chloroformate (5.00 mL, 47.2 mmol) drop-wise over 5 minutes. The resulting reaction mixture was heated to 85° C. and allowed to stir at that temperature for 16 hours. Thereafter, a sample of the reaction material was removed, concentrated under reduced pressure, and analyzed by $^1$H NMR; conversion to the carbamate was determined to be 55%.

Into the mixture was added a second and final portion of (5.00 mL, 47.2 mmol) of allyl chloroformate and the resulting reaction mixture was allowed to stir at 85° C. for an additional 6 hours. The reaction mixture was cooled to a temperature of about 20° C. and filtered through a plug of CELITE. The filtrate was concentrated under reduced pressure and analyzed by $^1$H NMR; greater than 95% conversion to 4-allyloxycarbonyl-morpholine was achieved.

Example 11

Decarboxylative Allylation of 4-Allyloxycarbonyl-Morpholine

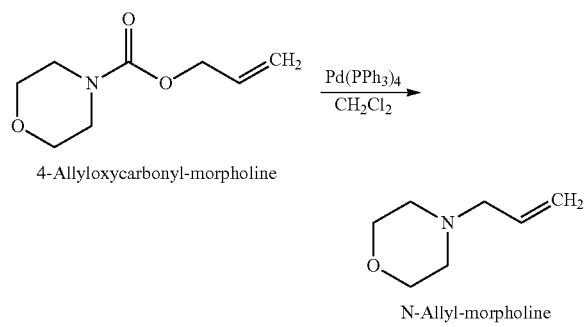

Into a round bottom flask equipped with a stir bar was charged 4-allyloxycarbonyl-morpholine (373 mg, 2.18 mmol) and dichloromethane (3.7 mL). The mixture was allowed to stir at a temperature of about 20° C. for 5 minutes. To the mixture was added tetrakis(triphenylphosphine)palladium[0] (50 mg, 0.043 mmol). The resulting reaction mixture was allowed to stir at a temperature of about 20° C. for 3 hours before being filtered through a pad of CELITE. The filtrate was concentrated under reduced pressure. The resulting oil was analyzed by $^1$H NMR; greater than 95% conversion to N-allyl-morpholine was achieved.

Example 12

Dehalogenation of 3-Chloropropyl Morpholine-4-carboxylate

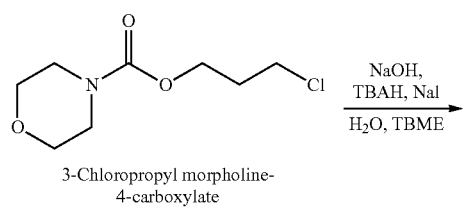

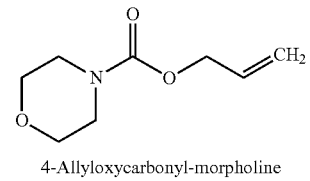

4-Allyloxycarbonyl-morpholine

Into a round bottom flask equipped with a stir bar was charged 3-chloropropyl morpholine-4-carboxylate (2.06 g, 9.92 mmol), 50% sodium hydroxide (5.5 mL), 40% tetrabutyl ammonium hydroxide (2.5 mL, 3.75 mmol), sodium iodide (0.18 g, 1.20 mmol), tert-butyl methyl ether (12.5 mL), and water (4.5 mL). The resulting reaction mixture was allowed to stir at a temperature of about 20° C. for 24 hours. The mixture was diluted with ethyl acetate (50 mL) and water (50 mL). The organic layer was separated and concentrated under reduced pressure. The resulting oil was analyzed by $^1$H NMR; greater than 95% conversion to 4-allyloxycarbonyl-morpholine was achieved.

Example 13

N-De-Ethylation of N,N-Di-iso-Propylethylamine

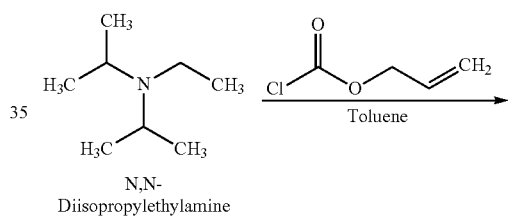

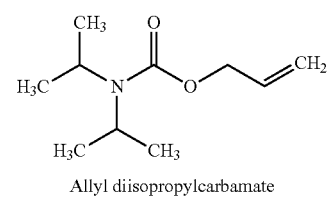

Allyl diisopropylcarbamate

Into a round bottom flask equipped with a stir bar and reflux condenser was charged N,N-di-iso-propylethylamine (3.75 mL, 21.5 mmol), a first portion of allyl chloroformate (3.30 mL, 31.2 mmol), and toluene (15.0 mL). The resulting reaction mixture was heated to 110° C. and allowed to stir at that temperature for 20 hours. Thereafter, the reaction mixture was sampled and analyzed by HPLC; the results demonstrated that greater than 70% conversion to allyl di-iso-propylcarbamate was achieved.

Into the mixture was added a second and final portion of allyl chloroformate (1.75 mL, 16.5 mmol) and the resulting reaction mixture was heated and stirred at 110° C. for an additional 24 hours. The mixture was concentrated under reduced pressure. The resulting oil was analyzed by $^1$H NMR; greater than 95% conversion to allyl di-iso-propylcarbamate was achieved.

Example 14

Decarboxylative Allylation of Allyl Di-iso-Propylcarbamate

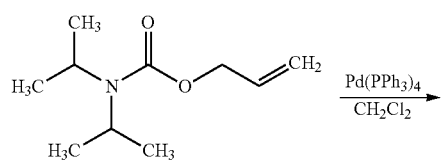

Allyl diisopropylcarbamate

N,N-Diisopropylallylamine

Into a round bottom flask equipped with a stir bar was charged allyl di-iso-propylcarbamate (500 mg, 2.70 mmol) and dichloromethane (2.5 mL). The mixture was allowed to stir at a temperature of about 20° C. for 5 minutes. To the mixture was added tetrakis(triphenylphosphine)palladium [0] (62 mg, 0.054 mmol). The resulting reaction mixture was allowed to stir at a temperature of about 20° C. for 16 hours. The mixture was filtered through a pad of CELITE and the filtrate was concentrated under reduced pressure. The resulting oil was analyzed by HPLC and $^1$H NMR; the results demonstrated that greater than 95% conversion to N,N-di-iso-propylallylamine was achieved.

Example 15

Alkylation of Noroxymorphone with Allyl Chloroformate

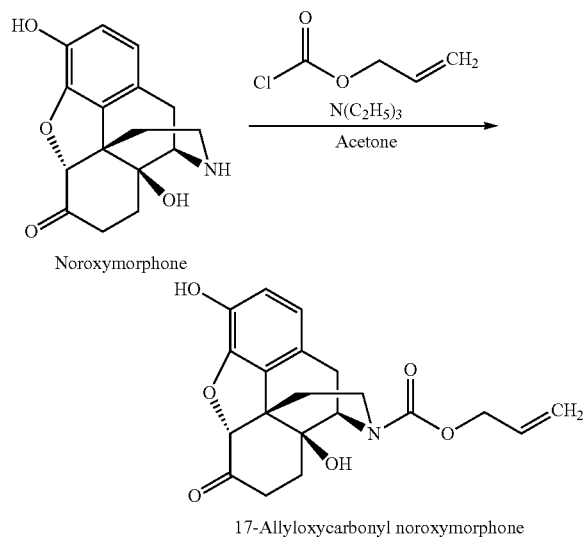

Noroxymorphone

17-Allyloxycarbonyl noroxymorphone

Into a round bottom flask equipped with a stir bar was charged noroxymorphone (0.99 g, 3.45 mmol), acetone (5.0 mL), and allyl chloroformate (0.35 mL, 3.29 mmol). The mixture was stirred at a temperature of about 20° C. To the stirred mixture was added triethylamine (0.05 mL, 0.36 mmol) and the resulting reaction mixture was allowed to stir at a temperature of about 20° C. for 16 hours. The mixture was acidified to a pH of 1.0 with 0.75N aqueous hydrochloric acid (100 mL). The aqueous layer was extracted twice with dichloromethane (100 mL for each extraction). The organic portions were combined and concentrated under reduced pressure. The resulting oil was analyzed by $^1$H NMR; the NMR spectrum was consistent with the 17-allyloxycarbonyl noroxymorphone product.

Example 16

Alkylation of Noroxymorphone with 3-Chloropropyl Chloroformate

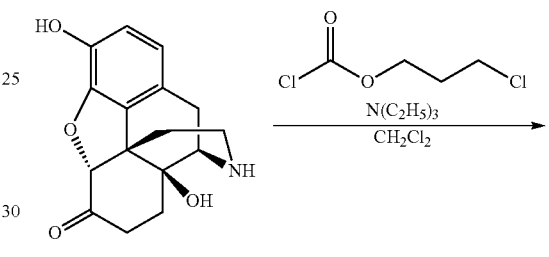

Noroxymorphone

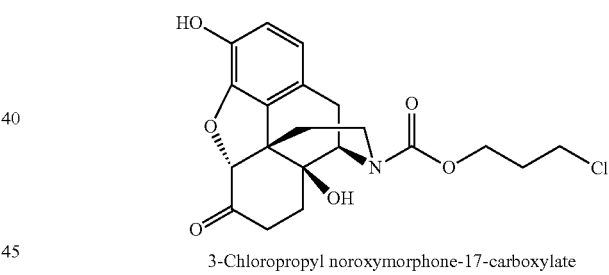

3-Chloropropyl noroxymorphone-17-carboxylate

Into a round bottom flask equipped with a stir bar was charged noroxymorphone (1.00 g, 3.48 mmol), dichloromethane (5.0 mL), and 3-chloropropyl chloroformate (0.40 mL, 3.32 mmol). The mixture was stirred at a temperature of about 20° C. To the stirred mixture was added triethylamine (0.40 mL, 2.87 mmol) and the mixture was allowed to stir for 2 hours. To the mixture was added potassium carbonate (1.00 g, 7.24 mmol) and ethanol (15 mL). The resulting reaction mixture was heated to 60° C. and stirred at that temperature for 16 hours. To the mixture was added water (15 mL) and the mixture was cooled to a temperature of about 20° C. The mixture was acidified to a pH of 1.0 with 0.75N aqueous hydrochloric acid (100 mL). The aqueous layer was extracted twice with dichloromethane (20 mL for each extraction). The organic portions were combined and concentrated under reduced pressure. The resulting oil was analyzed by $^1$H NMR; the NMR spectrum was consistent with the 3-chloropropyl noroxymorphone-17-carboxylate product.

Example 17

N-Demethylation of Oxymorphone with 3-Chloropropyl Chloroformate

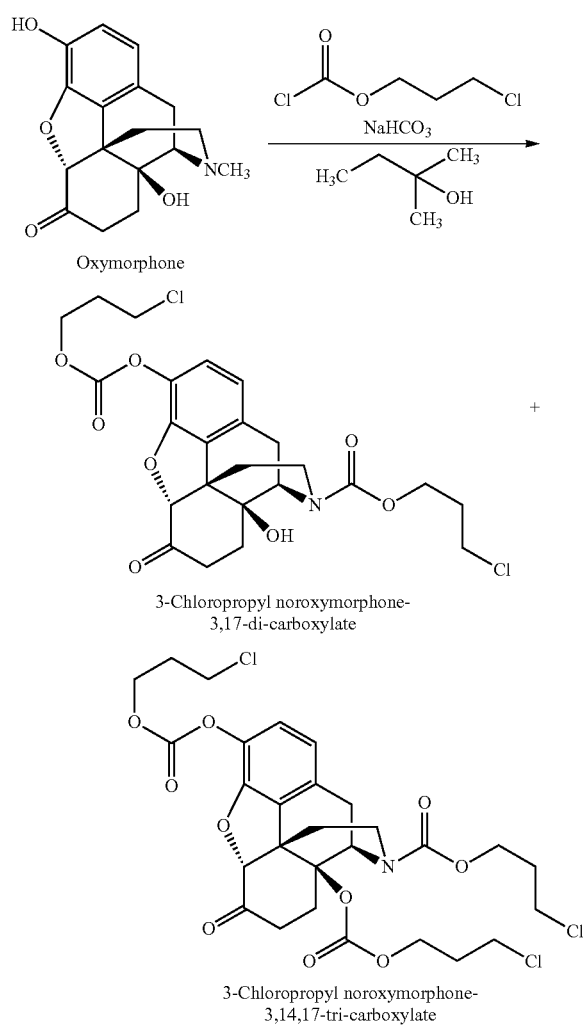

Into a round bottom flask equipped with a stir bar and reflux condenser was charged oxymorphone (10.02 g, 33.3 mmol), sodium bicarbonate (6.96 g, 82.9 mmol), and tert-amyl alcohol (75 mL). The mixture was allowed to stir at a temperature of about 20° C. for 5 minutes. Into the mixture was added 3-chloropropyl chloroformate (12.0 mL, 99.5 mmol) drop-wise over 5 minutes. The resulting reaction mixture was heated to 80° C. and allowed to stir at that temperature for 16 hours. The mixture was cooled to a temperature of about 20° C. and treated with 1N aqueous hydrochloric acid (125 mL). The mixture was stirred at a temperature of about 20° C. for 15 minutes. The stirring was stopped and the organic and aqueous layers were allowed to separate. The organic layer was concentrated under reduced pressure. The resulting oil was analyzed by HPLC and $^1$H NMR; the results were consistent with a 95:5 product ratio of 3-chloropropyl noroxymorphone-3,17-di-carboxylate:3-chloropropyl noroxymorphone-3,14,17-tri-carboxylate.

Example 18

Alternate Procedure for N-Demethylation of Oxycodone

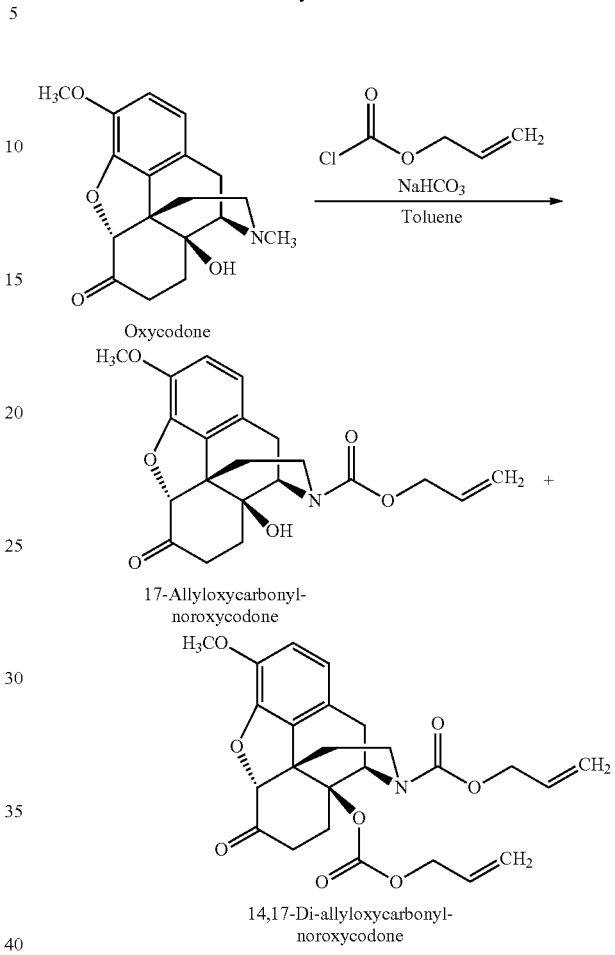

Into a round bottom flask equipped with a distillation head, reflux condenser, and stir bar was charged oxycodone (6.11 g, 19.37 mmol) and toluene (50 mL). The mixture was stirred and heated to reflux under an atmosphere of nitrogen for 1.5 hours. The mixture was cooled to 84° C. and sodium bicarbonate (3.27 g, 38.92 mmol) was charged to the mixture. Into the mixture was added a first portion of allyl chloroformate (1.00 mL, 9.44 mmol). The resulting reaction mixture was allowed to stir at 84° C. until the conversion to the 17-allyloxycarbonyl-products did not increase by HPLC analysis, approximately 16 hours.

Into the mixture was added a second portion of allyl chloroformate (1.00 mL, 9.44 mmol). The resulting reaction mixture was allowed to stir at 84° C. until the conversion to the 17-allyloxycarbonyl-products did not increase by HPLC analysis, approximately 16 hours.

Into the mixture was added a third portion of allyl chloroformate (1.00 mL, 9.44 mmol). The resulting reaction mixture was allowed to stir at 84° C. until the conversion to the 17-allyloxycarbonyl-products did not increase by HPLC analysis, approximately 16 hours.

Into the mixture was added a fourth and final portion of allyl chloroformate (1.00 mL, 9.44 mmol). The resulting reaction mixture was allowed to stir at 84° C. until the conversion to the 17-allyloxycarbonyl-products did not increase by HPLC analysis, approximately 16 hours. The mixture was cooled to a temperature of about 20° C. and washed twice with water (100 mL for each wash). HPLC analysis of the product demonstrated that a three component mixture of oxycodone:17-allyloxycarbonyl-noroxycodone: 14,17-di-allyloxycarbonyl-noroxycodone was prepared, with an HPLC area % ratio of 19.3:28.8:51.9 (80.7% conversion to products comprising 17-allyloxycarbonyl).

All publications, patents, patent applications, and other documents cited in this application are hereby incorporated by reference in their entireties for all purposes to the same extent as if each individual publication, patent, patent application, or other document were individually indicated to be incorporated by reference for all purposes.

While various specific embodiments have been illustrated and described, it will be appreciated that various changes can be made without departing from the spirit and scope of the invention(s).

What is claimed is:

1. A method for making a compound of Formula (41):

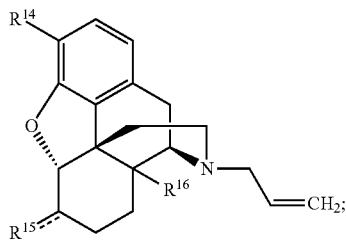
(41)

comprising:

(a) contacting a compound of Formula (45):

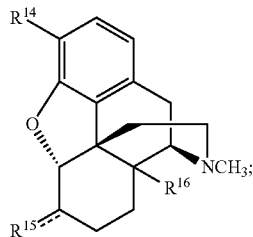
(45)

with a compound of Formula (10):

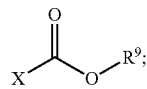
(10)

to provide a compound of Formula (60):

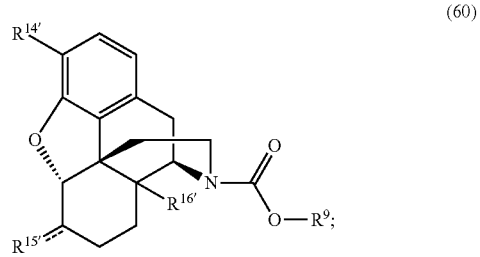
(60)

(b) contacting the compound of Formula (60) with an alkoxide of Formula (61):

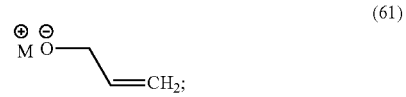
(61)

to provide the compound of Formula (95):

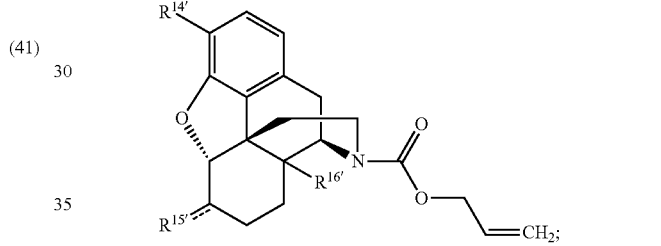
(95)

and (c) contacting the compound of Formula (95) with a transition metal catalyst to provide the compound of Formula (41), wherein:
X is selected from —Cl, —Br, and —I;
$R^9$ is selected from phenyl and 4-nitro-phenyl;
$R^{14}$ and $R^{16}$ are each independently selected from —OH, —H, and —OR$^{17}$;
$R^{15}$ is selected from —OH, —H, —OR$^{17}$, =O, and =CH$_2$;
$R^{17}$ is an oxygen protecting group;
$R^{14'}$ and $R^{16'}$ are each independently selected from —OH, —H, —OR$^{17}$, and —OC(O)OR$_9$;
$R^{15'}$ is selected from —OH, —H, —OR$^{17}$, =O, =CH$_2$, and —OC(O)OR$^9$;
and
M is selected from the group consisting of Na, K, and Li.

2. The method of claim 1, wherein $R^{14}$ and $R^{16}$ are each independently selected from —H and —OR$^{17}$ and $R^{15}$ is selected from —H, —OR$^{17}$, =O, and =CH$_2$.

3. The method of claim 1, wherein:
the oxygen protecting group is selected from the group consisting of allyl, benzoyl, benzyl, β-methoxyethoxymethyl, dimethoxytrityl, methoxymethyl, para-methoxybenzyl, methylthiomethyl, pivaloyl, tetrahydropyranyl, trityl, trimethylsilyl, tert-butyldimethylsilyl, tert-butyldimethylsilyloxymethyl, tri-iso-propylsilyl, methyl, ethoxyethyl, —C(O)O—CH$_2$—CH=CH$_2$, tert-butyl-diphenylsilyl, [bis-(4- methoxyphenyl)phenylmethyl)], triphenylmethyl, —C(O)(C$_1$-C$_4$) alkyl, —C(O)OR$^{18}$, and —(C$_1$-C$_6$) alkyl, each alkyl being unsubstituted or substituted with 1, 2, 3, 4, or 5 independently-selected R$^{21}$ groups;

each R$^{18}$ is independently selected from —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected R$^{21}$ groups; and each R$^{21}$ is independently selected from —Cl, —Br, —I, —NH$_2$, —CN, and phenyl.

4. The method of claim 3, wherein the oxygen protecting group is allyl, benzoyl, benzyl, β-methoxyethoxymethyl, dimethoxytrityl, methoxymethyl, para-methoxybenzyl, methylthiomethyl, pivaloyl, tetrahydropyranyl, trityl, trimethylsilyl, tert-butyldimethylsilyl, tert-butyldimethylsilyloxymethyl, tri-iso-propylsilyl, methyl, ethoxyethyl, or —C(O)O—CH$_2$—CH═CH$_2$.

5. The method of claim 2, wherein:
the oxygen protecting group is selected from the group consisting of allyl, benzoyl, benzyl, β-methoxyethoxymethyl, dimethoxytrityl, methoxymethyl, para-methoxybenzyl, methylthiomethyl, pivaloyl, tetrahydropyranyl, trityl, trimethylsilyl, tert-butyldimethylsilyl, tert-butyldimethylsilyloxymethyl, tri-iso-propylsilyl, methyl, ethoxyethyl, —C(O)O—CH$_2$—CH═CH$_2$, tert-butyl-diphenylsilyl, [bis-(4-methoxyphenyl)phenylmethyl)], triphenylmethyl, —C(O)(C$_1$-C$_4$) alkyl, —C(O)OR$^{18}$, and —(C$_1$-C$_6$) alkyl, each alkyl being unsubstituted or substituted with 1, 2, 3, 4, or 5 independently-selected R$^{21}$ groups;

each R$^{18}$ is independently selected from —(C$_1$-C$_6$) alkyl, —(C$_2$-C$_6$) alkenyl, and —(C$_2$-C$_6$) alkynyl, each alkyl, alkenyl, and alkynyl being unsubstituted or substituted with 1, 2, 3, 4, or 5 independently-selected R$^{21}$ groups; and each R$^{21}$ is independently selected from —Cl, —Br, —I, —NH$_2$, —CN, and phenyl.

6. The method of claim 5, wherein the oxygen protecting group is allyl, benzoyl, benzyl,β-methoxyethoxymethyl, dimethoxytrityl, methoxymethyl, para-methoxybenzyl, methylthiomethyl, pivaloyl, tetrahydropyranyl, trityl, trimethylsilyl, tert-butyldimethylsilyl, tert-butyldimethylsilyloxymethyl, tri-iso-propylsilyl, methyl, ethoxyethyl, or —C(O)O—CH$_2$—CH═CH$_2$.

7. The method of claim 1, wherein the contacting in step (a) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

8. The method of claim 7, wherein the solvent comprises tert-amyl alcohol, dichloromethane, tetrahydrofuran, or combinations of two or more thereof.

9. The method of claim 1, wherein the contacting in step (b) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

10. The method of claim 9, wherein the solvent comprises tert-amyl alcohol, dichloromethane, tetrahydrofuran, or combinations of two or more thereof.

11. The method of claim 1, wherein the transition metal catalyst comprises a transition metal selected from the group consisting of Pd[0], Pd[II], Ni[0], Ni[II], Mo[0], Ru[II], Rh[I], and combinations of two or more thereof.

12. The method of claim 11, wherein the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, [Mo(CO)$_6$-DPPE], RhH(PPh$_3$)$_4$—P(n-Bu)$_3$, and combinations of two or more thereof.

13. The method of claim 2, wherein the transition metal catalyst comprises a transition metal selected from the group consisting of Pd[0], Pd[II], Ni[0], Ni[II], Ru[II], and combinations of two or more thereof.

14. The method of claim 13, wherein the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, and combinations of two or more thereof.

15. The method of claim 4, wherein the transition metal catalyst comprises a transition metal selected from the group consisting of Pd[0], Pd[II], Ni[0], Ni[II], Ru[II], and combinations of two or more thereof.

16. The method of claim 15, wherein the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, and combinations of two or more thereof.

17. The method of claim 6, wherein the transition metal catalyst comprises a transition metal selected from the group consisting of Pd[0], Pd[II], Ni[0], Ni[II], Ru[II], and combinations of two or more thereof.

18. The method of claim 17, wherein the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$, [Pd(OAc)$_2$]/PPh$_3$, [Ni(COD)$_2$]/PPh$_3$, NiCl$_2$/PPh$_3$, Ni[P(OEt)$_3$]$_4$, and combinations of two or more thereof.

19. The method of claim 1, wherein the contacting in step (c) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

20. The method of claim 19, wherein the solvent comprises tert-amyl alcohol, dichloromethane, tetrahydrofuran, or combinations of two or more thereof.

21. The method of claim 19, wherein the transition metal catalyst comprises a transition metal selected from the group consisting of Pd[0], Pd[II], Ni[0], Ni[II], Ru[II], and combinations of two or more thereof.

22. The method of claim 21, wherein the transition metal catalyst is selected from the group consisting of Pd(PPh$_3$)$_4$, Pd(Ph$_2$P(CH$_2$)$_4$PPh$_2$)$_2$, Ni(PPh$_3$)$_4$, Ni(Ph$_2$P(CH$_2$)$_4$PPh$_2$)$_2$, ((pentamethylcyclopentadienyl)RuCl)$_4$, [Pd(DBA)$_2$]/PPh$_3$,

[Pd(OAc)$_2$]/PPh$_3$, [Ni(COD)$_2$]/PPh$_3$, NiCl$_2$/PPh$_3$, Ni[P(OEt)$_3$]$_4$, and combinations of two or more thereof.

23. The method of claim 2, wherein the contacting in step (a) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

24. The method of claim 23, wherein the solvent comprises tert-amyl alcohol, dichloromethane, tetrahydrofuran, or combinations of two or more thereof.

25. The method of claim 2, wherein the contacting in step (b) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

26. The method of claim 25, wherein the solvent comprises tert-amyl alcohol, dichloromethane, tetrahydrofuran, or combinations of two or more thereof.

27. The method of claim 2, wherein the contacting in step (c) occurs in a solvent, wherein the solvent is selected from the group consisting of chloroform, dichloromethane, 1,2-dichloroethane, toluene, tetrahydrofuran, ethyl acetate, acetone, tert-amyl alcohol, tert-butyl alcohol, 3-methyl-3-pentanol, 2,3-dimethyl-3-pentanol, 3-ethyl-pentanol, 2-methyl-2-hexanol, acetonitrile, benzene, carbon tetrachloride, chlorobenzene, 1,2-dichlorobenzene, N,N-dimethylformamide, trifluorotoluene, 1,4-dioxane, 1,2-dimethoxyethane, xylene, and combinations of two or more thereof.

28. The method of claim 27, wherein the solvent comprises tert-amyl alcohol, dichloromethane, tetrahydrofuran, or combinations of two or more thereof.

29. The method of claim 1, wherein $R^{15'}$ is selected from —OH, —H, —OR$^{17}$, =CH$_2$, and —OC(O)OR$^9$.

* * * * *